US010421947B2

(12) United States Patent
Ferro

(10) Patent No.: US 10,421,947 B2
(45) Date of Patent: Sep. 24, 2019

(54) DENTAL PULP MARROW SIMILAR CELLS (DPMSC) AND METHODS OF ISOLATING AND USING

(71) Applicant: FOUNDATION FOR TRANSLATIONAL SCIENCE, Culver City, CA (US)

(72) Inventor: Federico Ferro, Campoformido Ud (IT)

(73) Assignee: Foundation for Translational Science, Culver City, CA (US)

( * ) Notice: Subject to any disclaimer, the term of this patent is extended or adjusted under 35 U.S.C. 154(b) by 0 days.

(21) Appl. No.: 15/046,306

(22) Filed: Feb. 17, 2016

(65) Prior Publication Data

US 2016/0244724 A1 Aug. 25, 2016

Related U.S. Application Data

(62) Division of application No. 13/000,344, filed as application No. PCT/EP2009/058015 on Jun. 26, 2009, now abandoned.

(30) Foreign Application Priority Data

Jun. 26, 2008 (IT) .............................. RM2008A0342

(51) Int. Cl.
*C12N 5/0775* (2010.01)
(52) U.S. Cl.
CPC ........ *C12N 5/0664* (2013.01); *C12N 2500/05* (2013.01); *C12N 2500/36* (2013.01); *C12N 2500/38* (2013.01); *C12N 2501/105* (2013.01); *C12N 2501/11* (2013.01); *C12N 2501/115* (2013.01); *C12N 2501/119* (2013.01); *C12N 2501/135* (2013.01); *C12N 2501/33* (2013.01); *C12N 2501/39* (2013.01); *C12N 2501/999* (2013.01)

(58) Field of Classification Search
CPC ............ C12N 5/0664; C12N 2501/135; C12N 2501/33; C12N 2501/11; C12N 2501/105; C12N 2501/999; C12N 2500/05; C12N 2500/36; C12N 2500/38
See application file for complete search history.

(56) References Cited

U.S. PATENT DOCUMENTS

| | | | |
|---|---|---|---|
| 2005/0106724 A1 | 5/2005 | Schierholz et al. | |
| 2007/0009492 A1 | 1/2007 | Shi et al. | |
| 2007/0258957 A1 | 11/2007 | Bowermaster et al. | |
| 2007/0280907 A1* | 12/2007 | Lue ................... | A01K 67/0271 424/93.3 |
| 2011/0158962 A1 | 6/2011 | Ferro | |

FOREIGN PATENT DOCUMENTS

| | | |
|---|---|---|
| EP | 1748066 A1 | 1/2007 |
| JP | 2009-539378 A | 11/2009 |
| WO | 2003/066840 A2 | 8/2003 |
| WO | 2004/094588 A2 | 11/2004 |
| WO | 2006/010600 A2 | 2/2006 |
| WO | 2006/100088 A1 | 9/2006 |
| WO | WO-2007/146123 A2 | 12/2007 |
| WO | 2009/156495 A1 | 12/2009 |

OTHER PUBLICATIONS

Le Blanc et al. Generation of Immunosuppressive Mesenchymal Stem Cells in Allogeneic Human Serum. Transplantation 2007;84:1055-1059. (Year: 2007).*
Roche et al. Oct-4, Rex-1, and Gata-4 Expression in Human MSC Increase the Differentiation Efficiency But Not hTERT Expression. Journal of Cellular Biochemistry 101:271-280 (2007). (Year: 2007).*
Office Action Received for European Patent Application No. 09769343.6, dated Oct. 25, 2012, 3 pages.
Final Office Action received for U.S. Appl. No. 13/000,344 dated Sep. 30, 2013, 17 pages.
Non Final Office Action received for U.S. Appl. No. 13/000,344, dated Aug. 19, 2015, 18 pages.
Non Final Office Action received for U.S. Appl. No. 13/000,344, dated Mar. 5, 2013, 15 pages.
Restriction Requirement received for U.S. Appl. No. 13/000,344 dated Nov. 30, 2012, 10 pages.
Ben-Shushan et al., "Rex-1, a Gene Encoding a Transcription Factor Expressed in the Early Embryo, Is Regulated via Oct-3/4 and Oct-6 Binding to an Octamer Site and a Novel Protein, Rox-1, Binding to an Adjacent Site", Molecular and Cellular Biology, vol. 18, No. 4, Apr. 1998, pp. 1866-1878.
Benson et al., "Identification of a Homeodomain Binding Element in the Bone Sialoprotein Gene Promoter That Is Required for Its Osteoblast-selective Expression", The Journal of Biological Chemistry, vol. 275, No. 18, 2000, pp. 13907-13917.
Bissell et al., "Context, Tissue Plasticity, and Cancer: Are Tumor Stem Cells also Regulated by the Microenvironment?", Cancer Cell, vol. 7, Jan. 2005, pp. 17-23.
Brüstle et al., "Embryonic Stem Cell-Derived dial Precursors: A Source of Myelinating Transplants", Science, vol. 285, Jul. 30, 1999, pp. 754-756.
Chambers et al., "Functional Expression Cloning of Nanog, a Pluripotency Sustaining Factor in Embryonic Stem Cells", Cell, vol. 113, May 30, 2003, pp. 643-655.
Collins et al., "A DNA Polymorphism Discovery Resource for Research on Human Genetic Variation", Genome Research, vol. 8, 1998, pp. 1229-1231.
Constantinescu, S., "Stemness, Fusion and Renewal of Hematopoietic and Embryonic Stem Cells", J. Cell. Mol. Med., vol. 7, No. 2, 2003, pp. 103-112.
Delorme et al., "Specific Plasma Membrane Protein Phenotype of Culture-Amplified and Native Human Bone Marrow Mesenchymal Stem Cells", Blood, vol. 111, 2008, pp. 2631-2635.

(Continued)

Primary Examiner — Sean C. Barron
(74) Attorney, Agent, or Firm — Lucas & Mercanti, LLP

(57) ABSTRACT

The invention provides for isolated population of pulp marrow similar cells (DPMSCs) and methods for isolating and using these cells. The population of DPMSCs are highly homogenous for CD10, CD29, CD13, CD44, CD49a, CD49d, CD59, CD73, CDw90, CD105, Oct-4 Isoform A and B, Nanog, Sox-2, and SSEA-4.

9 Claims, No Drawings

(56) References Cited

OTHER PUBLICATIONS

Ferro et al., "Dental Pulp Marrow Similar Cells: A New Source of Stem Cells for Clinical Applications", The American Journal of Pathology, vol. 173, Sep. 2008, 1 page.
Ferro et al., "Isolation and Characterization of Human Dental Pulp Derived Stem Cells by Using Media Containing Low Human Serum Percentage as Clinical Grade Substitutes for Bovine Serum", PLOS One, vol. 7, No. 11, Nov. 2012, 9 pages.
Grossi et al., "Differentiation and Immunoregulatory Activity of Dental Pulp-Derived Mesenchymal Cells", Blood, vol. 104, No. 11, Nov. 2004, 2 pages.
Jiang et al., "Pluripotency of Mesenchymal Stem Cells Derived from Adult Marrow", Nature, vol. 418, Jul. 4, 2002, pp. 41-49.
Jo et al., "Isolation and characterization of postnatal stem cells from human dental tissues", Tissue Eng, vol. 13, 2007, pp. 767-773.
Kannagi et al., "Stage-Specific Embryonic Antigens (SSEA-3 and -4) are Epitopes of a Unique Globo-Series Ganglioside Isolated from Human Teratocarcinoma Cells", The EMBO Journal, vol. 2, No. 12, 1983, pp. 2355-2361.
Kerkis et al., "Isolation and Characterization of a Population of Immature Dental Pulp Stem Cells Expressing OCT-4 and other Embryonic Stem Cell Markers", vol. 184, No. 3-4, Jan. 2006, pp. 105-116.
Laino et al., "An Approachable Human Adult Stem Cell Source for Hard-Tissue Engineering", Journal of Cellular Physiology, vol. 206, 2006, pp. 693-701.
Laslett et al., "Characterization and Culture of Human Embryonic Stem Cells", Trends in Cardiovascular Medicine, vol. 13, No. 7, 2003, pp. 295-301.
Liu et al., "Dental Pulp Stem Cells", Meth Enzymol, vol. 419, 2006, pp. 99-113.
Mann et al., "Cultured Rat Pulp Cells have the Potential to Form Bone, Cartilage, and Dentin in Vivo", Biological Mechanisms of Tooth Movement and Craniofacial Adaptation, 1996, pp. 7-16.
Mitsui et al., "The Homeoprotein Nanog Is Required for Maintenance of Pluripotency in Mouse Epiblast and ES Cells", Cell, vol. 113, May 30, 2003, pp. 631-642.
Miura et al., "SHED: Stem Cells From Human Exfoliated Deciduous Teeth", Proceedings of the National Academy of Sciences of USA, vol. 100, No. 10, May 13, 2003, pp. 5807-5812.
Nichols et al., "Formation of Pluripotent Stem Cells in the Mammalian Embryo Depends on the POU Transcription Factor Oct4", Cell, vol. 95, Oct. 30, 1998, pp. 379-391.
International Preliminary Report on Patentability received for PCT Patent Application No. PCT/EP2009/058015, dated Jan. 13, 2011, 9 pages.
International Search Report and Written Opinion received for PCT Patent Application No. PCT/EP2009/058015, dated Nov. 3, 2009, 11 pages.
Pierdomenico et al., "Multipotent Mesenchymal Stem Cells with Immunosuppressive Activity Can Be Easily Isolated from Dental Pulp", Transplantation, vol. 80, No. 6, Sep. 27, 2005, pp. 836-842.
Pittenger et al., "Multilineage Potential of Adult Human Mesenchymal Stem Cells", Science, vol. 243, 1999, pp. 143-137.
Rosfjord et al., "The Octamer Motif Present in the Rex-1 Promoter Binds Oct-1 and Oct-3 Expressed by EC Cells and ES Cells", Biochemical and Biophysical Research Communications, vol. 203, No. 3, Sep. 30, 1994, pp. 1795-1802.
Schwatrz et al., "Adult Stem Cell Plasticity", Chapter 3, Human Embryonic Stem Cell edited by Odorico et al., First Edition, 2005, pp. 45-59.
Suchanek et al., "Dental Pulp Stem Cells and Their Characterization", Biomed Pap Med Fac Univ Palacky Olomouc Czech Repub, vol. 153, No. 1, Mar. 2009, pp. 31-35.
Uwanogho et al., "Embryonic Expression of the Chicken Sox2, Sox3 and Sox11 Genes Suggests an Interactive Role in Neuronal Development", Mechanisms of Development, vol. 49, 1995, pp. 23-36.
Yamamoto et al., "Progressive Development of the Osteoblast Phenotype during Differentiation of Osteoprogenitor Cells Derived from Fetal Rat Calvaria: Model for in Vitro Bone Formation", Biol. Pharm. Bull., vol. 25, No. 4, 2002, pp. 509-515.
Zhang et al., "Induction of Specific T-Cell Tolerance by Adenovirus-Transfected, Fas Ligand-Producing Antigen-Presenting Cells", Nature Biotechnology, vol. 16, Nov. 1998, pp. 1045-1049.
Non Final Office Action dated Aug. 19, 2015, for U.S. Appl. No. 13/000,344, filed Mar. 11, 2011, 17 pages.

* cited by examiner

DENTAL PULP MARROW SIMILAR CELLS (DPMSC) AND METHODS OF ISOLATING AND USING

CROSS-REFERENCES TO RELATED APPLICATIONS

This application is a divisional application of U.S. patent application Ser. No. 13/000,344, having a 371(c) filing date of Mar. 11, 2011, now abandoned, which is a national stage application of International Patent Application No. PCT/EP2009/058015, filed on Jun. 26, 2009, which application is related to and claims the priority benefit of Italian patent application RM2008A000342, filed on Jun. 26, 2008, the entire contents each of which is hereby incorporated by reference in its entirety.

FIELD OF THE INVENTION

The invention relates generally to compositions and methods for isolating and using dental pulp marrow similar cells (DPMSCs).

BACKGROUND OF THE INVENTION

Organ and tissue generation from stem cells and their successive transplantation provide possible treatments for a number of pathologies, making stem cells a central focus of research in many fields. Using stem cells for generation of organs and tissues for transplantation provides a possible therapy for diabetes, Parkinson's disease, liver disease, heart disease, and autoimmune disorders, to name a few. However, there are at least two major problems associated with organ and tissue transplantation. First, there is a shortage of donor organs and tissues. As few as 10 percent of the organs needed for transplant in Italy along ever become available to a recipient. See, e.g., Nord Italian Transplant program report 2007. According to the Nord Italian Transplant program report, only about 1,200 of the 9,000 Italians who needed a new kidney in 2006 received one, and that in 2006 an average of 12% of the patients in the waiting list for a liver transplant dic while waiting to receive the suitable organ. The second major problem is the potential incompatibility of the transplanted tissue with the immune system of the recipient. Because the donated organ or tissue is recognized by the host immune system as foreign, anti-rejection medications must be provided to the patient at a significant cost, both financially and physically.

Xenotransplantation, or transplantation of tissue or organs from another species, could provide an alternative possibility to overcome the shortage of human organs and tissues. Xenotransplantation would offer the advantage of advanced planning of the transplant, allowing the organ to be harvested while still healthy and allowing the patient to undergo any possible pre-treatment prior to transplant surgery. Unfortunately, xenotransplantation does not overcome the problem of tissue incompatibility, but even exacerbates it. Furthermore, according to the Centers for Disease Control, there is evidence that damaging viruses cross species barriers. Pigs have become likely candidates as organ and tissue donors, yet cross-species transmission of more than one virus from pigs to humans has been documented. For example, over a million pigs were reported slaughtered in Malaysia in an effort to contain an outbreak of Hendra virus, a disease that was transmitted to more than 70 humans with deadly results. See, e.g., Butler, D., *Nature* (1999) 398: 549.

A promising source of organs and tissues for transplantation therefore lies in the development of stem cell technology. Theoretically, stem cells can undergo self-renewing cell division to give rise to phenotypically and genotypically identical daughters for an indefinite time and ultimately can differentiate into at least one final cell type. By generating tissues or organs from a patient's own stem cells, or by genetically altering heterologous cells so that the recipient immune system does not recognize them as foreign, transplant tissues can be generated to provide the advantages associated with xenotransplantation without the associated risk of infection or tissue rejection.

Stem cells also provide promise for improving the results of gene therapy. A patient's own stem cells could be genetically altered in vitro, then reintroduced in vivo to produce a desired gene product. These genetically altered stem cells would have the potential to be induced to differentiate to form a multitude of cell types for implantation at specific sites in the body, or for systemic application. Alternatively, heterologous stem cells could be genetically altered to express the recipient's major histocompatibility complex (MHC) antigen, or no MHC, to allow transplant of those cells from donor to recipient without the associated risk of rejection.

Stem cells are cells that have extensive, possibly indefinite, proliferation potential to differentiate into several cell lineages and can repopulate tissues upon transplantation. The quintessential stem cell is the embryonic stem (ES) cell, as it has unlimited self-renewal and multipotent differentiation potential. These cells are derived from the inner cell mass of the blastocyst, or can be derived from the primordial germ cells from a post-implantation embryo (embryonal germ cells or EG cells). ES and EG cells have been derived from mouse, and more recently also from non-human primates and humans. When introduced into mouse blastocysts or blastocysts of other animals, ES cells can contribute to all tissues of the mouse (animal). When transplanted in postnatal animals, ES and EG cells generate teratomas, which again demonstrates their multipotency. ES (and EG) cells can be identified by positive staining with the antibodies SSEA-1 and SSEA-4.

At the molecular level, ES and EG cells express a number of transcription factors highly specific for these undifferentiated cells. These include Oct-4 and Nanog. Also found are the LIF-R and the transcription factors Sox-2 and Rox-1, even though the latter two are also expressed in non-ES cells. Oct-4 is a transcription factor expressed in the pre-gastrulation embryo, early cleavage stage embryo, cells of the inner cell mass of the blastocyst, and in embryonic carcinoma (EC) cells. Oct-4 is down-regulated when cells are induced to differentiate in vitro and in the adult animal. Oct-4 is only found in germ cells. Several studies have shown that Oct-4 is required for maintaining the undifferentiated phenotype of ES cells and plays a major role in determining early steps in embryogenesis and differentiation. Oct-4, in combination with Rox-1, causes transcriptional activation of the Zn-finger protein Rex-1 and is also required for maintaining ES in an undifferentiated state. Human or murine primordial germ cells require presence of LIF. Another hallmark of ES cells is presence of telomerase, which provides these cells with an unlimited self-renewal potential in vitro.

Stem cells have been identified in most organ tissues. The best characterized is the hematopoietic stem cell. This is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages (see Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827; Hill, B., et al., *Exp. Hematol.* (1996) 24(8): 936-943). When transplanted into lethally irradiated animals or humans, hematopoietic stem cells can repopulate the erythroid, neutrophil-macrophage, megakaryocyte and lymphoid hemopoietic cell pool. In vitro, hemopoietic stem cells can be induced to undergo at least some self-renewing cell divisions and can be induced to differentiate to the same lineages as is seen in vivo. Therefore, this cell fulfills the criteria of a stein cell. Stem cells which differentiate only to form cells of hematopoietic lineage, however, are unable to provide a source of cells for repair of other damaged tissues, for example, heart or lung tissue damaged by high-dose chemotherapeutic agents.

A second stem cell that has been studied extensively is the neural stem cell (Gage F. H., *Science* 287:1433-1438, 2000); Svendsen C. N., et al, *Brain Path.* 9:499-513, 1999; Okabe S., et al, *Mech. Dev.* 59:89-102, 1996). Neural stem cells were initially identified in the subventricular zone and the olfactory bulb of fetal brain. Until recently, it was believed that the adult brain no longer contained cells with stem cell potential. However, several studies in rodents, and more recently also non-human primates and humans, have shown that stem cells continue to be present in adult brain. These stem cells can proliferate in vivo and continuously regenerate at least some neuronal cells in vivo. When cultured ex vivo, neural stem cells can be induced to proliferate, as well as to differentiate into different types of neurons and glial cells. When transplanted into the brain, neural stem cells can engraft and generate neural cells and glial cells. Therefore, this cell falls within the scope of a stem cell.

Mesenchymal stem cells (MSC), originally derived from the embryonal mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A third tissue specific cell that has been named a stem cell is the mesenchymal stem cell, initially described by Fridenshtein (Fridenshtein, *Arkh. Patol.*, 44:3-11, 1982). A number of mesenchymal stem cells have been isolated (see, for example, Caplan, A., et al., U.S. Pat. No. 5,486,359; Young. H., et al., U.S. Pat. No. 5,827,735; Caplan, A., et al., U.S. Pat. No. 5,811,094; Bruder, S., et al., U.S. Pat. No. 5,736,396; Caplan, A., et al., U.S. Pat. No. 5,837,539; Masinovsky, B., U.S. Pat. No. 5,837,670; Pittenger, M., U.S. Pat. No. 5,827,740; Jaiswal, N., et al., *J. Cell Biochem.* (1997) 64(2): 295-312; Cassiede P., et al., *J. Bone Miner. Res.* (1996) 11(9): 1264-1273; Johnstone, B., et al., *Exp. Cell Res.* (1998) 238(1): 265-272; Yoo, et al., *J. Bone Joint Sure. Am.* (1998) 80(12): 1745-1757; Gronthos, S., *Blood* (1994) 84(12): 4164-4173; Makino, S., et al., *J. Clin. Invest.* (1999) 103(5): 697-705). Of the many mesenchymal stem cells that have been described, all have demonstrated limited differentiation to form only those differentiated cells generally considered to be of mesenchymal origin. To date, the most multipotent mesenchymal stem cell reported is the cell isolated by Pittenger, et al., which expresses the $SH2^+$ $SH4^+$ $CD29^+$ $CD44^+$ $CD71^+$ $CD90^+$ $CD106^+$ $CD120a^+CD124^+CD14^-$ $CD34^-$ $CD45^-$ phenotype. This cell is capable of differentiating to form a number of cell types of mesenchymal origin, but has been reported by the team who isolated it to be apparently limited in differentiation potential to cells of the mesenchymal lineage since hematopoietic cells were never identified in the expanded cultures. (Pittenger, et al., *Science* (1999) 284: 143-147.)

Other stem cells have been identified, including gastrointestinal stem cells, epidermal stem cells, and hepatic stem cells, also termed oval cells (Potten C., *Philos Trans R Soc Lond B Biol Sci* 353:821-30, 1998; Watt F., *Philos. Trans R Soc Lond B Biol Sci* 353:831, 1997; Alison M., et al, *Hepatol* 29:678-83, 1998).

Compared with ES cells, tissue specific stem cells have less self-renewal ability and, although they differentiate into multiple lineages, they are not as pluripotent. In addition, the degree of telomerase activity in tissue specific stem cells has not been fully explored, in part because large numbers of highly enriched populations of these cells are difficult to obtain.

Until recently, it was thought that organ specific stem cells could only differentiate into cells of the same tissue. A number of recent publications have suggested that adult organ specific stem cells may be capable of differentiating into cells of different tissues. A number of studies have shown that cells transplanted at the time of a bone marrow transplant can differentiate into skeletal muscle (Ferrari, *Science* 279:528-30, 1998; Gussoni, *Nature* 401:390-4, 1999). This could be considered within the realm of possible differentiation potential of mesenchymal cells that are present in marrow. Jackson reported that muscle satellite cells can differentiate into hemopoietic cells, again a switch in phenotype within the splanchnic mesoderm (Jackson, PNAS USA, 96:14482-6, 1999). Other studies have shown that stem cells from one embryonal layer (e.g., splanchnic mesoderm) can differentiate into tissues thought to be derived during embryogenesis from a different embryonal layer. For example, endothelial cells or their precursors detected in humans or animals that underwent marrow transplantation are at least in part derived from the marrow donor (Takahashi, *Nat Med* 5:434-8, 1999; Lin, *Clin Invest* 105:71-7, 2000). Thus, visceral mesoderm and not splanchnic mesoderm, such as MSC, derived progeny are transferred with the infused marrow. Even more surprising are the reports demonstrating both in rodents and humans that hepatic epithelial cells and biliary duct epithelial cells are derived from the donor marrow (Petersen, *Science* 284:1168-1170, 1999; Theise, *Hepatology* 31:235-40, 2000; Theise, *Hepatology* 32:11-6, 2000). Likewise, three groups have shown that neural stem cells can differentiate into hemopoietic cells. Finally, Clarke et al. reported that neural stem cells injected into blastocysts can contribute to all tissues of the chimeric mouse (Clarke, *Science* 288:1660-3, 2000).

Many of these studies have not conclusively demonstrated that a single cell can differentiate into tissues of different organs. Many investigators did not identify the phenotype of the initiating cell. An exception is the study by Weissman and Grompe, who showed that cells that repopulated the liver were present in $Lin^-Thy_{tLow}Sca_{1+}$ marrow cells, which are highly enriched in hematopoietic stem cells. Likewise, the Mulligan group showed that marrow Sp cells, highly enriched for HSC, can differentiate into muscle and endothelium, and Jackson et al. showed that muscle Sp cells are responsible for hemopoietic reconstitution (Gussoni et al., *Nature* 401:390-4, 1999).

Transplantation of tissues and organs generated from heterologous embryonic stem cells requires either that the cells be further genetically modified to inhibit expression of certain cell surface markers, or that the use of chemotherapeutic immune suppressors continue in order to protect against transplant rejection. Thus, although embryonic stem cell research provides a promising alternative solution to the problem of a limited supply of organs for transplantation, the problems and risks associated with the need for immunosuppression to sustain transplantation of heterologous cells or tissue would remain. An estimated 20 immunologically different lines of embryonic stem cells would need to be established in order to provide immunocompatible cells for therapies directed to the majority of the population (Wadman, M., *Nature* (1999) 398: 551).

Using cells from the developed individual, rather than an embryo, as a source of autologous or allogeneic stem cells would overcome the problem of tissue incompatibility associated with the use of transplanted embryonic stem cells, as well as solve the ethical dilemma associated with embryonic stem cell research. The greatest disadvantage associated with the use of autologous stem cells for tissue transplant thus far lies in their limited differentiation potential. A number of stem cells have been isolated from fully-developed organisms, particularly humans, but these cells, although reported to be pluripotent, have demonstrated limited potential to differentiate to multiple cell types.

Thus, even though stem cells with multiple differentiation potential have been isolated previously by others and by the present inventors, a progenitor cell with the potential to differentiate into a wide variety of cell types of different lineages, including fibroblasts, osteoblasts, chondrocytes, adipocytes, skeletal muscle, endothelium, stroma, smooth muscle, cardiac muscle and hemapoietic cells, has not been described. If cell and tissue transplant and gene therapy are to provide the therapeutic advances expected, a stem cell or progenitor cell with the greatest or most extensive differentiation potential is needed. What is needed is the adult equivalent of an embryonic stem cell.

As an alternative to embryonic stem cell therapy, adult stem cells have shown promise (Caplan, 1991, 2000, 2003, 2004, 2005; Caplan and Bruder, 2001; Kuehle and Goodell, 2002; Pittenger, 2004). For example, multipotent adult progenitor cells from mouse bone marrow (mMAPC) were shown to express several embryonic stem (ES) cell markers, such as Oct-4 (POU transcription factor), Rex-1 (transcription factor) and SSEA-1 (stage-specific embryonic antigen), and to contribute to all embryonic cell lineages when a single cell is injected into the blastocyst (Jiang et al., 2002). While bone marrow is an excellent source of stem cells with proven therapeutic value, the process of collecting bone marrow is invasive, and, moreover, recent data implicate bone marrow stem cells in cancer development (Houghton et al., 2004). The expansion of the list of the potential sources of pluripotent adult stem cells beyond a small group consisting of cord blood, bone marrow, adipose tissue, and amniotic stem cells (Jiang et al., 2002; Zuk et al., 2002; Miki et al., 2005) would be of value. Extending earlier findings in rodents (Mann et al., 1996), the recent discovery of relatively immature stem cells in the dental pulp of human exfoliated deciduous teeth (SHED) has offered a potentially non-invasive source of stem cells (Miura et al., 2003). SHED showed rapid expansion and proliferation in vitro while expressing several mesenchymal stem cell markers, such as STRO-1 and CD146. Stem cells from dental pulp (Miura et al., 2003) appeared to be inferior in their potential therapeutic value compared to ES cells or mMAPCs, since they were not shown to express Oct-4, SSEAs, Nanog, or any other hallmarks of totipotent stem cells, while their multilineage terminal differentiation was only marginally successful (Jiang et al., 2002; Chambers et al., 2003; Constantinescu, 2003; Laslett et al., 2003; Mitsui et al., 2003; Pierdomenico et al., 2005; Laino et al., 2006). SHED have been shown to be highly heterogeneous, because only 9% of SHED express markers of undifferentiated cells, and it is not clear if clones obtained from SHED maintain expression of these markers (Miura et al., 2003). Previously, it has been reported that removal of stem cells from their natural milieu may change their differentiation properties (Bissell and Lafarge, 2005; Schwartz and Verfaillie, 2005). Additional publications that described stem cells obtained from dental pulp include: WO 03/066840, WO 04/094588, US 2005/0106724, US 2007/0009492, US 2007/0258957, WO 03/066840, EP 1748066 A1, WO 2006/010600, and WO 2006/100088. However, none of these references describe a homogeneous population of purified stem cells which can differentiate into cells of different lineages.

Accordingly, what is needed is a population of stem cells which show the plasticity of ES cells in their ability to become a multitude of cells but derived from non-embryonic sources and non-invasive sources. The present invention fulfils these needs and provides additional benefits as well.

The specification is most thoroughly understood in light of the references cited herein. Some of the references have their full bibliographic information after the Examples section. The disclosures of all publications, patents, patent applications, and published patent applications referred to herein are each hereby incorporated by reference herein in their entireties.

SUMMARY OF THE INVENTION

The invention provides for compositions of isolated dental pulp marrow similar cells (DPMSC) and methods of isolating, culturing, and differentiating these cells as well as methods for using these cells. The isolated populations of DPMSCs display particular marker phenotype, which can be measured by protein analysis or nucleic acid analysis (e.g., rt-PCR). Accordingly, in one aspect, the invention provides for an isolated population of DPMSCs wherein at least about 90% of the cells in the population co-express each of the following markers: CD10, CD13, CD29, CD44, CD49a, CD49d, CD59, CD73, CD90, CD105, Oct-4 Isoform A and B, Nanog, Sox-2, and SSEA-4. In another aspect, the invention provides for an isolated population of DPMSCs wherein at least about 95% of the cells in the population co-express each of the following markers: CD10, CD13, CD29, CD44, CD49a, CD49d, CD59, CD73, CD90, CD105, Oct-4 Isoform A and B, Nanog, Sox-2, and SSEA-4. In another aspect, the invention provides for an isolated population of DPMSCs wherein about 90-99% of the cell population expresses each of the following markers: CD10, CD13, CD29, CD44, CD49a, CD49d, CD59, CD73, CD90, CD105, Oct-4 Isoform A and B. Nanog, Sox-2, and SSEA-4.

In another aspect, any of the populations of DPMSCs can exhibit the phenotype wherein 0.25-1% of the cells in the population express CD34 and CD45. In another aspect, any of the populations of DPMSCs can exhibit the phenotype wherein less than 1% of the cells in the population express CD34 and CD45. In another aspect, any of the populations of DPMSCs can exhibit the phenotype wherein the cells of the population co-express mRNA of each of the following: Oct-4 Isoforms A and B, Nanog, Sox-2, SSEA-4, c-Myc, Klf-4, and Rex-1. In another aspect, any of the populations of DPMSCs can exhibit the phenotype wherein the population has an average doubling rate of about 28-30 hours. In another aspect, any of the populations of DPMSCs can exhibit the phenotype wherein the DPMSCs have the capacity to differentiate into one, two or all three of the cell types of ectodermal, endodermal, or mesodermal lineages. In another aspect, any of the populations of DPMSCs can be human DPMSCs.

The invention also provides for isolated populations of DPMSCs derived from human dental pulp, wherein at least about 90% of the cells in the population co-express each of the following markers: CD10, CD29, CD13, CD44, CD49a, CD49d, CD59, CD73, CDw90, CD105, Oct-4, Nanog, Sox-2, and SSEA-4; wherein 0.25-1% of the cells in the population express CD34 and CD45; wherein the cells have normal karyotype; and wherein the cells of the population have the capacity to differentiate into cell types of at least two of ectodermal, endodermal, or mesodermal lineages.

In another aspect, any of the population of DPMSCs can exhibit the phenotype wherein the cells have the capacity to differentiate into any one or more of the following: osteoblast, skeletal muscle cell, smooth muscle cell, cardiac muscle cell, glial cell, and neuronal cell.

In some aspects, the DPMSCs are derived from a tooth organ. In one aspect, the tooth organ is from a child. In another aspect, the tooth organ is from an adult.

In some aspects, the population of DPMSCs is contained in a vessel, such as tissue culture plates, bottles and matrices.

The invention also provides for isolated populations of DPMSCs which have been cultured to induce differentiation wherein the starting population is DPMSCs described above, wherein the differentiation results in the DPMSC becoming a differentiated cell selected from a group consisting of: a bone cell, skeletal muscle cell, smooth muscle cell, cardiac muscle cell, glial cell, neuronal cell, skin epithelial cell, liver epithelial cell, pancreas epithelial cell, pancreas endocrine cell, pancreatic islet cell, pancreas exocrine cell, gut epithelium cell, kidney epithelium cell, epidermal associated structure, hair follicles, soft tissues surrounding teeth, dentin (teeth), enamel (teeth), and cement (teeth).

The invention also provides for isolated populations of DPMSCs wherein the genome of the cells in the population has not been altered by insertion of pre-selected isolated DNA, by substitution of a segment of the cellular genome with pre-selected isolated DNA, or by deletion of or inactivation of at least a portion of the cellular genome.

The invention also provides for methods of obtaining a population of DPMSCs described above by culturing a dental pulp source in media supplemented with one or more growth factors selected from the group consisting of: platelet-derived growth factor, insulin, selenium, epidermal growth factor (EGF), insulin-like growth factor (IGF), dexamethasone, linoleic acid, and ascorbic acid to obtain population of DPMSCs. In some aspects, all of the previous components are included in the culturing media. In some aspects, the DPMSCs are human DPMSCs and the dental pulp source is from a human. In other aspects, the adherent cells and non-adherent cells are co-cultured without selection by immunodepletion, physical depletion, or chemical depletion. In other aspects, the method does not deplete the starting source of cells or the cell culture of mononuclear cells expressing CD3, CD14, CD19, CD38, CD66b and CD45 glycophorin A. In other aspects, the methods further comprise placing the cells in a cell culture container, wherein the cell culture container does not comprises an extracellular matrix (ECM) substrate. In other aspects of the methods, the serum percentage comprises about 0.5-2.5%.

In another aspect of the invention, the methods of culturing include one or more of the following culturing parameters: insulin is present at a concentration of about 10 to about 50 µg/ml, transferrin at a concentration of greater than 0 but less than about 10 µg/ml, selenium at a concentration of about 0.1 to about 5 µg/ml, linoleic acid at a concentration of about 0 to about 1 µg/m, dexamethasone at a concentration of about 0.005 to 0.15 µM, L-ascorbic acid at a concentration of about 10-50 mg/L, platelet-derived growth factor at a concentration of about 5 to about 15 ng/ml, epidermal growth factor 1 to at a concentration of about 15 ng/ml, insulin-like growth factor at a concentration of 1 to about 15 ng/ml, and fibroblast growth factor-b1 at a concentration of about 15 ng/ml. In yet another aspect, the methods of culturing include all of previous components in the culturing media.

In another aspect, the invention provides for methods of inducing differentiation of DPMSCs to differentiated cells and compositions of the differentiated cells obtained from these methods.

The invention also encompasses cells produced by any of the processes described herein. In one embodiment, the invention provides for DPMSCs produced by the culturing method as described in Example 1.

In another aspect, the invention provides for methods of providing therapeutic assistance to an individual in need thereof by administering an amount of DPMSCs effective to aid therapy to the individual. In another aspect, the invention provides for methods of administering stem cells to an individual in need thereof for beneficial effects. In some embodiments, an effective amount of cells are introduced to the individual in need thereof. In other embodiments, the individual in need thereof is an individual with any one or more of the medical, biological, genetic or physiological conditions described herein.

In yet another aspect, the invention provides methods of providing therapeutic enzymes, proteins, or other biological product to an individual with or suspected of having a genetic defect by:
(a) performing an in utero transplantation of a sufficient amount of DPMSCs to form a chimerism of cells or tissues to produce human cells in prenatal or post-natal individuals following transplantation and (b) allowing the cells to produce therapeutic enzymes, proteins, or other products in the individual with or suspected of having genetic defects.

In yet another aspect, the invention provides methods of providing gene therapy in an individual in need of therapeutic treatment, by: (a) genetically altering DPMSCs by introducing an isolated pre-selected DNA encoding a desired gene product into one or more DPMSCs; (b) expanding the cells in culture; and (c) introducing the cells into the body of the individual to produce the desired gene product, thus providing gene therapy.

In yet another aspect, the invention provides methods of providing therapy for damaged tissue in a human individual in need thereof by: (a) culturing the DPMSCs to proliferate them; and (b) contacting an effective amount of the expanded DPMSCs with the damaged tissue of said individual to provide therapy. In one embodiment, the cells are introduced into the body of the individual by localized injection or by systemic injection. In another embodiment, the cells are introduced into the body of the individual in conjunction with a suitable matrix implant that provides additional genetic material, cytokines, growth factors, or other factors to promote growth and differentiation of the cells. In another embodiment, the cells are encapsulated within a polymer capsule prior to introduction into the body of the individual.

In yet another aspect, the invention provides methods of identifying genetic polymorphisms associated with physiologic abnormalities by: (a) isolating DPMSCs from a statistically significant population of individuals from whom phenotypic data can be obtained; (b) expanding the DPMSCs from the statistically significant population of individuals to establish DPMSC cultures; (c) identifying at least one genetic polymorphism in the cultured DPMSCs; (d) inducing the cultured DPMSCs to differentiate; and (e) characterizing aberrant metabolic processes associated with the genetic polymorphism by comparing the differentiation pattern exhibited by DPMSCs having a normal genotype with the differentiation pattern exhibited by DPMSCs having an identified genetic polymorphism.

In yet another aspect, the invention provides methods for treating cancer in an individual in need thereof by: (a) genetically altering DPMSCs to express a tumoricidal protein, an anti-angiogenic protein, or a protein that is expressed on the surface of a cancer cell in conjunction with a protein associated with stimulation of an immune response to antigen; and (b) introducing an amount of the genetically altered DPMSCs into the individual effective to halt the growth of or eradicate the cancer cells.

In yet another aspect, the invention provides methods of determining cellular responses to biologic or pharmacologic agents by: (a) isolating DPMSCs from a statistically significant population of individuals: (b) expanding the DPMSCs from the statistically significant population of individuals to establish a plurality of DPMSC cultures; (c) contacting the DPMSC cultures with one or more biologic or pharmacologic agents; (d) identifying one or more cellular responses to the one or more biologic or pharmacologic agents; and (e) comparing the cellular responses of the DPMSC cultures from individuals in the statistically significant population to determine the cellular responses to biologic or pharmacologic agents.

In yet another aspect, the invention provides methods of treating blindness in an individual in need thereof comprising administering to individual an effective amount of neuroretinal cells derived from DPMSCs. In one embodiment, the blindness is associated with any one or more of the following: neuroretinal disease, macular degeneration, diabetic retinopathy, glaucoma, or retinitis pigmentosa. In another embodiment, the DPMSC is genetically modified to selectively express an endogenous gene or a transgene that ameliorates blindness in the individual.

In yet another aspect, the invention provides methods for treating periodontal disease in an individual in need thereof comprising administering to the individual an effective amount of gingiva-like material wherein the gingiva-like material has been derived from DPMSCs.

In yet another aspect, the invention provides methods for aiding skin grafting and plastic surgery in an individual in need thereof comprising administering to the individual an effective amount of skin epithelial tissue wherein the skin epithelial tissue has been derived from DPMSCs.

In yet another aspect, the invention provides methods for producing human hematopoietic cells or blood cells ex vivo comprising culturing DPMSCs in a manner as to induce its differentiation into hematopoietic cells or blood cells.

In yet another aspect, the invention provides methods for providing therapeutic assistance to treat cardiac diseases in an individual in need thereof comprising administering to the individual an amount of cardiomyocytes derived from DPMSCs effective to ameliorate cardiac failure. In some embodiments, the cardiac disease is selected from the group consisting of: myocarditis, cardiomyopathy, heart failure, damage caused by heart attacks, hypertension, atherosclerosis, and heart valve dysfunction.

In yet another aspect, the invention provides methods for providing therapeutic assistance to treat neural diseases in an individual in need thereof comprising administering to the individual an amount of DPMSCs or neuronally related differentiated cells derived from DPMSCs effective to aid amelioration of neurodegenerative diseases. In some embodiments, the neural disease is selected from the group consisting of: stroke, Alzheimer's, Parkinson's disease, Huntington's disease, AIDS associated dementia, spinal cord injury, and metabolic diseases affecting the brain or other nerves.

In yet another aspect, the invention provides methods for providing therapeutic assistance to treat diseases of the joints or cartilage in an individual in need thereof comprising administering to the individual an amount of DPMSCs, chondrocytes derived from DPMSCs, or osteoblast derived from DPMSCs effective to aid amelioration of cartilage degenerative diseases. In some embodiments, the disease of the joints or cartilage is selected from the group consisting of: cartilage tears, cartilage thinning, osteoarthritis, bone fractures, non-healing fractures, osteoarthritis, and holes in bones cause by cancerous tumors spreading to bone.

In yet another aspect, the invention provides methods of providing a database of gene profiles of a pluripotent derived stem cell to aid in drug discovery by: (a) determining the gene profile from DPMSCs from at least one individual, wherein the gene profile involves at least one gene; and (b) storing the gene profile(s) on an accessible medium.

DETAILED DESCRIPTION

The invention provides for compositions, methods for isolation of DPMSCs, methods for inducing specific differentiation of the cells and the cell populations resulting therefrom. More specifically, the invention relates to an isolated population of DPMSCs, which is highly homogeneous such that a significant percentage, or proportion of, the population of DPMSCs co-expresses the following markers: CD10, CD13, CD29, CD44, CD49a, CD49d, CD59, CD73, CDw90, CD105, Oct-4 Isoform A and B, Nanog, Sox-2, and SSEA-4 and such that, within the same population, a low percentage of the cells in the population express CD34 and CD45. The highly homogeneous population of DPMSCs have the potential to differentiate to form cells of a variety of cell lineages of the endoderm, mesoderm, and ectoderm.

I. General Techniques

The practice of the present invention will employ, unless otherwise indicated, conventional techniques of stem cell biology, cell culturing, molecular biology (including recombinant techniques), microbiology, cell biology, biochemistry and immunology, which are within the skill of the art. Such techniques are explained fully in the literature, such as, *Molecular Cloning: A Laboratory Manual*, third edition (Sambrook et al., 2001) Cold Spring Harbor Press; *Oligonucleotide Synthesis* (P. Herdewijn, ed., 2004); Animal Cell Culture (R. I. Freshney), ed., 1987); *Methods in Enzymology* (Academic Press, Inc.); *Handbook of Experimental Immunology* (D. M. Weir &C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991) *Short Protocols in Molecular Biology* (Wiley and Sons, 1999), *Embryonic Stem Cells: A Practical Approach* (Notaranni et al. eds., Oxford University Press 2006); *Essentials of Stem Cell Biology* (R. Lanza, ed., Elsevier Academic Press 2006); *Stem Cell Assays* (*Methods in Molecular Biology*) (Mohan C. Vemuri, Ed., Humana Press; first edition (Aug. 10, 2007); *Mesenchymal Stem Cells: Methods and Protocols* (*Methods in Molecular Biology*) (Darwin J. Prockop, Donald G. Phinney, Bruce A. Bunnell, Eds., first edition (Mar. 7, 2008)); *Handbook of Stem Cells* (Robert Lanza, et al., Eds., Academic Press (Sep. 14, 2004); *Stem Cell Culture* Vol 86: *Methods in Cell Biology* (Jennie P. Mather, Ed., Academic Press, first edition (May 15, 2008)); *Practical Hematopoietic Stem Cell Transplantation* (Andrew J. Cant, et al. Eds., Wiley-Blackwell, first edition (Jan. 22, 2007)); *Hematopoietic Stem Cell Protocols* (Kevin D. Bunting, Ed., Humana Press, 2nd ed. edition (Jan. 31, 2008)); *Bone Marrow and Stem Cell Transplantation* (*Methods in Molecular Medicine*) (Meral Beksac, Ed., Humana Press; first edition (May 3, 2007)); *Stem Cell Therapy and Tissue Engineering for Cardiovascular Repair: From Basic Research to Clinical Applications* (Nabil Dib. et al., Eds., Springer, first edition (Nov. 16, 2005)); *Blood And Marrow Stem Cell Transplantation: Principles, Practice, And Nursing Insights* (Kim Schmit-Pokorny (Author) and Susan Ezzone (Editor), Jones & Bartlett Publishers; third edition (May 22, 2006)); *Hematopoietic Stem Cell Protocols* (Christopher A. Klug and Craig T. Jordan, Eds., Humana Press; first edition (Dec. 15, 2001)); and *Clinical Bone Marrow and Blood Stem Cell Transplantation* (Kerry Atkinson, et al., Eds., Cambridge University Press; third edition (Dec. 8, 2003)).

Unless defined otherwise, all technical and scientific terms used herein have the same meaning as is commonly understood by one of ordinary skill in the art to which this invention belongs.

If a definition set forth in this section is contrary to or otherwise inconsistent with a definition set forth in patents, published patent applications and other publications that are herein incorporated by reference, the definition set forth in this section prevails over the definition that is incorporated herein by reference.

II. Definitions

As used herein, the terms "dental pulp-derived stem cell (DPSC)," "dental pulp-derived progenitor cells," "dental pulp marrow similar cells" (DPMSC), are used interchangeably and refer to a highly homogeneous cell population that is fairly uniform in its co-expression of a panel of certain markers: CD10, CD13, CD29, CD44, CD49a, CD49d, CD59, CD73, CDw90, CD105, Oct-4 Isoform A and B, Nanog, Sox-2, SSEA-4, CD34, and CD45. It is to be understood that other markers can be expressed on the DPMSCs in addition to the list above.

As used herein, the terms "highly homogenous" and "homogenous" population of DPMSCs refer to a population of DPMSCs that is fairly uniform in its co-expression of a panel of certain markers: CD10, CD13, CD29, CD44, CD49a, CD49d, CD59, CD73, CDw90, CD105, Oct-4 Isoform A and B, Nanog, Sox-2, SSEA-4, CD34, and CD45. In one aspect, a significant percentage, or proportion of the population of DPMSCs of the invention express the following markers: CD10, CD13, CD29, CD44, CD49a, CD49d, CD59, CD73, CDw90, CD105, Oct-4 Isoform A and B, Nanog, Sox-2, and SSEA-4 and additionally, within the same population, a low percentage of the cells in the population express CD34 and CD45. The percentage of the population of DPSMCs co-expressing the marker profiles described herein can be about any of about 40%, 50%, 60%, 70%, 75%, 80%, 85%, 90%, 95%, 98%, or 99%. In some aspects, the percentage of the population of DPSMCs co-expressing the marker profiles described herein can be at least about any of about 40%, 50%, 60%, 70%, 75%, 80%, 85%, 90%, 95%, 98%, or 99%. The population of DPMSCs can be contained in a vessel for purposes of culturing, proliferation, or differentiation, which encompasses not only standard cell culture vessels but matrices and other materials with which one of skill in the art would use to culture DPMSCs.

As used herein, the term "population" or "isolated population" of pluripotent DPMSCs refers to a population of one or more DPMSCs that has been manipulated to provide a preparation of cells that is substantially free of additional components. In some aspects, the cell preparation is at least about 60%, by weight, volume, or number, free from other components that are present when the cell is produced or cultured. In various aspects, the cell is at least about 75%, or at least about 85%, or at least about 90%, 91%, 92%, 93%, 94%, 95%, 96%, 97%, or at least about 98%, or at least about 99%, by weight, volume, or number, pure. In some aspects, the percentage refers to a percentage of stem cells in a cell culture or population. A population or isolated population of DPMSCs can be obtained, for example, by purification from a natural source, e.g., by mechanical or physical or chemical extraction, fluorescence-activated cell-sorting, or other techniques known to the skilled artisan. The purity can be assayed by any appropriate method, such as fluorescence-activated cell-sorting (FACS) or by visual examination.

"Purity" as used to describe the purity of stem cells does not refer to the presence of only stem cells in the composition but rather indicates that the stem cells have been manipulated such that they have been removed from their natural tissue environment and indicates their relationship to the other cells present in the resulting population.

As used herein, the term "pluripotent" refers to a DPMSC's potential to differentiate into cells of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent stem cells can give rise to any fetal or adult cell type. Alone, they cannot develop into a fetal or adult animal because they lack the potential to contribute to extraembryonic tissue (e.g., placenta in vivo or trophoblast in vitro).

An "individual," "subject" or "patient" is a vertebrate. In certain embodiments, the vertebrate is a mammal. Mammals include, but are not limited to, primates (including human and non-human primates), pets (e.g., dogs, cats, rabbits, etc.), agricultural animals (e.g., cows, livestock, etc.), sport animals (e.g., horses), and rodents (e.g., mice and rats). In certain embodiments, a mammal is a human.

By "treatment" or "treating" is meant an approach for obtaining a beneficial or desired result, including clinical results. For purposes of this invention, beneficial or desired results include, but are not limited to, alleviation of symptoms associated with a condition diminishment of the extent of one or more symptoms associated with a condition, or prevention of a worsening of the symptoms associated with a condition. In some aspects, treatment with a one or more cells disclosed herein is accompanied by no or fewer side effects than are associated with currently available therapies.

"Receiving treatment" includes initial treatment and/or continuing treatment.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, the method may reduce the probability of disease development in a given time frame and/or reduce the extent of the disease in a given time frame, when compared to not using the method. In some aspects, such comparisons are based on clinical studies using a statistically significant number of individuals. Disease development can be detectable using standard clinical techniques. Development may also refer to disease progression that can be initially undetectable and includes occurrence, recurrence, and onset.

An "effective amount" (when used in the treatment or prophylaxis context, or in the context of palliating pain or alleviating the symptoms of a particular condition) is an amount sufficient to effect beneficial or desired results including clinical results. An effective amount can be administered in one or more administrations. For purposes of this invention, an effective amount of DPMSCs is a certain amount of cells that can reduce one of more symptoms of the conditions for which the individual is being treated. An effective amount of DPMSCs encompasses the use of DMP-SCs when they are being grown or proliferated in their pluripotent, undifferentiated state as well as the use of DMPSCs when they have been cultured further to induce them to differentiate down a particular pathway (e.g., neural, cardiomyocyte, chondrocyte, etc.). When used in the context of "assisting therapy," an effective amount enhances a therapeutic regimen (as compared to a regimen lacking the DPMSCs) and, as such, provides a beneficial or desired result.

As used herein, "in need thereof" includes individuals who have a condition or disease or are "at risk" for the condition or disease. As used herein, an "at risk" individual is an individual who is at risk of development of a condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, diet, history of previous disease, presence of precursor disease, genetic (i.e., hereditary) considerations, breeding protocols and considerations, and environmental exposure.

By "pharmaceutically acceptable carrier" is meant any material which, when combined with an active ingredient, allows the ingredient to retain biological activity and does not provoke an unacceptable immune response (e.g., a severe allergy or anaphylactic shock) based on the knowledge of a skilled practitioner. Examples include, but are not limited to, any of the standard pharmaceutical carriers such as carboxymethylcellulose (CMC), phosphate buffered saline solutions, water, emulsions such as oil/water emulsion, and various types of wetting agents. Exemplary diluents for aerosol or parenteral administration are phosphate buffered saline or normal (0.9%) saline. An exemplary carrier for the infusion of cells is CMC. Compositions comprising such carriers are formulated by well known conventional methods (see, for example, *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000, which are each hereby incorporated by reference in their entireties, particularly with respect to formulations).

General reference to "the composition" or "compositions" includes and is applicable to compositions of the invention. The invention also provides pharmaceutical compositions comprising the components described herein.

As used herein, the singular form "a", "an", and "the" includes plural references unless indicated otherwise. For example, "a" DPMSC includes one or more dental pulp marrow similar cells.

Reference to "about" a value or parameter herein includes (and describes) aspects that are directed to that value or parameter per se. For example, description referring to "about X" includes description of "X."

It is understood that aspects and aspects of the invention described herein include "comprising," "consisting," and "consisting essentially of" aspects and aspects.

III. Population of Dental Pulp Marrow Similar Cells (DPMSCs)

The present invention provides for homogeneous populations of dental pulp marrow similar cells (DPMSCs) that can differentiate to into many types of cells from multiple layers (e.g., ectoderm, mesoderm and endoderm). These cells show great plasticity in their ability to differentiate into multiple types of cells from different layers of the body. The DPMSCs exhibit differentiation phenotypes akin to an embryonic stem cell. The cells of the present invention described herein have the capacity to differentiate to form at least one, two or three differentiated cell types of mesodermal, ectodermal and endodermal origin. The phenotype of the population of DPMSCs of the invention is more homogenous in terms of the relatively high percentage of the cell population expressing particular markers (or low percentage of the cell population not expressing other particular markers) than other stem cell cultures described in the art, which tended to be fairly heterogeneous in that, as a whole, those stem cell population displayed a wide variations of phenotypes.

A. DPMSCs from Dental Pulp

DPMSCs can be obtained by using a starting source of dental pulp for culturing. In one aspect of the invention, the source of the dental pulp may be from child (e.g., teeth lost as part of losing baby teeth). In another aspect of the invention, the source of the dental pulp may be from adult teeth grown after losing baby teeth. In another aspect, the starting source may be derived from a tooth organ. In one aspect, deciduous dental pulp mononuclear cells are derived from dental pulp.

DPMSCs of the invention can be obtained from any vertebrate. In one aspect of the invention, DPSMCs are obtained from a mammal, such as a human. In other aspects of the invention, the DPMSCs are obtained from a non-human. In yet other aspects of the invention, the DPMSCs are obtained from primates (including human and non-human primates), pets (e.g., dogs, cats, rabbits, etc.), agricultural animals (e.g., cows, livestock, etc.), sport animals (e.g., horses), and rodents (e.g., mice and rats). In all cases, no human embryos are destroyed in the process of obtaining DPMSCs of the invention.

Accordingly, the invention provides for compositions (e.g., population or isolated population) of human DPMSCs, non-human DPMSCs, primate DPMSCs, as well as DPMSCs from different animal species. In one aspect of the invention, DPMSCs can be a subpopulation of dental pulp such that, under the experimental conditions described herein, the DPMSCs are predominantly and selectively proliferating. In other aspects of the invention, a gradient between the piece of dental pulp and the culture medium can serve as a vector directing the cells toward what they perceive as a site of injury, which can lead to their continued and selective migration in the Petri dish.

B. Phenotype of DPMSCs

The population of DPMSCs of invention can be described by various phenotypes. In one aspect, the population of DPMSCs can be described in terms of its homogeneity in its co-expression of certain markers. These markers can be on the cell surface and detected by standard methods in the art (e.g., flow cytometry). Alternatively, the population of DPMSCs can be described by the expression of certain genes within the cells and measured by standard assays in the art (e.g., rt-PCR). In yet another alternative, the DPMSCs can also be described by its karyotype (e.g., normal karyotype) or by its biological characteristics. Non-limiting examples of biological activities include cell doubling time, telomerase activity, and differentiation capabilities.

In one aspect of the invention, DNA content can be measured by standard assays in the art (e.g., FISH). The detection of telomerase activity can be determined by standard assays in the art (e.g., TRAP-assay/TRAPeze kit). In another aspect of the invention, cells can be stained by standard assays in the art (e.g., Von Kossa, Nuclear Fast Red). Alkaline phosphatase activity can be measured by standard assays in the art (e.g., Alkaline Phosphatase staining). In yet another aspect of the invention, glycogen can be detected by standard assays in the art (e.g., Periodic acid-Schiff staining). Albumin concentration can be determined by standard assays in the art (e.g., ELISA) and urea concentration can be determined by standard assays in the art (e.g., QuantiChrom™ Urea Assay). The details of the standard assays described here can be found in Example 2.

Accordingly, in one aspect, the population of DPMSCs of the invention is homogeneous in its co-expression of markers such as, but not limited to, CD10, CD13, CD29, CD44, CD49a, CD49d, CD59, CD73, CD90, CD105, Oct-4 Isoform A and B, Nanog, Sox-2, and SSEA-4. Homogeneity refers to the percentage of cells within a given population of DPMSCs that express the same marker profile. In some aspects, the invention provides for a population of DPMSCs that is homogeneous in that about 40%, 50%, 60%, 70%, 75%, 80%, 85%, 90%, 95%, 98%, or 99% of the cells in the population co-express CD10, CD13, CD29, CD44, CD49a, CD49d, CD59, CD73, CD90, CD105, Oct-4 Isoform A and B, Nanog, Sox-2, and SSEA-4. In other aspects, the invention provides for a population of DPMSCs that is homogeneous in that at least about 40% of the cells in the population co-express CD10, CD13, CD29, CD44, CD49a, CD49d, CD59, CD73, CD90, CD105, Oct-4 Isoform A and B. Nanog, Sox-2, and SSEA-4. Preferably, the population of DPMSCs are homogeneous to the extent that at least about 50%, at least about 60%, at least about 70%, at least about 75%, at least about 80%, at least about 85%, at least about 90%, at least about 95%, at least about 98%, or at least about 99% of the DPMSCs in the population co-express CD10, CD13, CD29, CD44, CD49a, CD49d, CD59, CD73, CD90, CD105, Oct-4 Isoform A and B, Nanog, Sox-2, and SSEA-4. In other aspects, about 90-99% the population of DPMSCs co-express these markers.

In another aspect, a low percentage (e.g., <1%) of the cells in the population of DPMSCs exhibits expression of markers such as CD34 and CD45. In the same homogeneous population where a significant percentage or proportion (e.g., at least about 90%) of the population of DPMSCs co-express CD10, CD13, CD29, CD44, CD49a, CD49d, CD59, CD73, CD90, CD105, Oct-4 Isoform A and B, Nanog, Sox-2, and SSEA-4, a low percentage or proportion (e.g., 0.25%-1%) of the population of human DPMSCs obtained after 14-20 cell doublings has expression of CD34 and CD45. In another aspect of the invention, a low percentage of the cells in the population of DPMSCs express CD66c, KDR, CD133, VE-Cad and CD117.

The findings by the inventors that the DPMSC population expressed SSEA-4 is consistent with other immunhistochemistry and cytofluorimetric assays, which showed that human DPMSCs, grown at $2-10^3/cm^2$ seeding density, express SSEA-4 protein after thawed (Kannagi R, *EMBO J.* 2:2355-61, 1983).

In another aspect of the invention, the population of DPMSCs also expressed a certain profile of messenger RNA expression. Analysis of a population of DPMSCs by rt-PCR can be done to determine messenger expression during proliferation phase. Non-limiting examples of messenger expression which can be detected in the DPMSC population of the invention include: Oct-4, MDR-1, Abcg-2, Msx-2, PPAR-γ, c-Met, CK-19, alkaline phosphatase, osteocalcin, osteonectin, BMP-2, BMP-4, BMP-7, BMPr-Ia, BMPr-Ib, Cbfa-I type I, Cbfa-I type II, Dlx-5, collagen I, FGFr-I, FGFr-II, aggrecan, dermo-I, dental matrix protein, G-Fap, glypican, $β^3$-Tubulin, neurofilament light, medium, heavy, NSE, musashi, vimentin, N-nos, ASA, SMA, cardiac actin, myocardin, ANP, Gata-4, Nkx-2.5, Mef-2a, c-TnI, and myosin heavy chain. On the other hand, the population of DPMSCs express minimal levels to no levels of messenger RNA for MHC-α, MHC-β, KDR, TRT, Osteopontin, BMPr-II, Collagen II, Map-2, V-Mlc, and cTnT. In one aspect of the invention, the population of DPMSCs co-express mRNA of each of the following: Oct-4 Isoforms A and B, Nanog, Sox-2, SSEA-4, c-Myc, Klf-4, and Rex-1.

Yet another way to characterize the population of DPMSCs of the invention is by protein expression. One way that the protein expression can be determined is by immunofluorescence of the DPMSCs during proliferation phase. Non-limiting examples of protein expression which can be detected in the DPMSC population of the invention include: Aggrecan, collagen I, FGFr-I, FGFr-II, c-TnT, collagen II, SMA, Neurofilament light, G-Fap, NSE, VWF, Cbfa-I, Gata-4, Msx-2, Neuro D, Nanog. Oct-4, SSEA-4. Immunoblot can also be used to determine protein expression of the DPMSCs during proliferation phase. Non-limiting examples of protein expression which can be detected in the DPMSC population of the invention include: ASA, Serca, $β^3$-Tubulin, Synaptophysin, Msx-2, Oct-4, Connexin-43, Dlx-5, Neuro-D, Ca-Channel, and Cbfa-I.

DPMSCs express mRNA for POU-domain transcription factor Oct-4, which is required to maintain undifferentiated state of embryonic stem (ES) cell/embryonal carcinoma (EC) cell. Oct-4 is a transcription factor expressed in the pregastrulation embryo, early cleavage stage embryo, cells of the inner cell mass of the blastocyst, and in embryonic carcinoma (EC) cells (Nichols J, et al *Cell* 95:379-91, 1998), and is down-regulated when cells are induced to differentiate. Expression of Oct-4 plays an important role in determining early steps in embryogenesis and differentiation. Oct-4, in combination with Rox-1, causes transcriptional activation of the Zn-finger protein Rex-1, also required for maintaining ES undifferentiated (Rosfjord E, Rizzino A., *Biochem Biophys Res Commun* 203:1795 802, 1997; Ben-Shushan E, et al, *Mol Cell Biol* 18:1866-78, 1998). In addition, Sox-2, expressed in ES/EC, but also in other more differentiated cells, is needed together with Oct-4 to retain the undifferentiated state of ES/EC (Uwanogho D., et al., *Mech Dev* 49:23-36, 1995).

Human DPMSCs of the invention express and stain positive with SSEA-4. Oct-4 protein levels tend to decrease in human DPMSCs cultures beyond 40 cell doublings, the results of which, without being bound by theory, may be due to a partial loss of undifferentiated phenotype. Thus, the presence of Oct-4, combined with SSEA-4, are markers that correlate with presence of the most primitive cells in DPMSC cultures.

DPMSCs of the invention display different rates of proliferation depending on how many doublings have occurred since the start of the culturing from the dental pulp source. Accordingly, in one aspect, the invention encompasses an isolated population of DPMSCs that have an average doubling time of about 30-40 hours for the initial ten cell doublings. The average doubling time can be about 30, 31, 32, 33, 34, 35, 36, 37, 38, 39 or 40 hours for the population of DPMSCs the initial ten cell doublings. In one embodiment, the doubling time is about 36 hours for the initial ten cell doublings. After the initial ten cell doublings, cell-doubling time can be about 28 hours until about 30-35 cell doublings and then the rate slowly decreases thereafter. The DPMSCs of the invention encompass an isolated population of DPMSCs that have an average doubling time of 25-40 hours for the proliferation of the DPMSCs as averaged over the time in culture. In yet another aspect of the invention, the average doubling time can be about 28 hours in 1.25-2.5% human serum medium and about 29 or 30 hours in 025-0.5% human serum medium. The estimated number of starting primary culture cells can be about 80 to 800.

A population of DPMSCs of the invention can proliferate as undifferentiated, pluripotent DPMSCs for at least about a month, preferably about two months, even more preferably about three months or more. Alternatively, the population of DPMSCs of the invention can proliferate as undifferentiated, pluripotent DPMSCs for at least about 10 doublings, preferably at least about 20 doublings, and even more preferably at least about 30, 40, 50, 60, or more doublings since the start of the culture from the dental pulp source. The invention also encompasses a population of DPMSCs which have been grown from cryopreserved DPMSCs.

In another aspect of the invention, the population of DPMSCs also display a reduction of telomere length as compared to internal controls as a measure of telomere activity. As further detailed in the Examples as one embodiment of the invention, the telomere length of DPMSCs from two donors (age 6 years) cultured at reseeding densities of $2 \times 10^3$ cells/cm$^2$ was between 10-20 kbp. The telomere length of the internal control 1301 cell line was estimated to be 100%. The mean telomere length of DPMSCs was 18.4% P2 and 17.1% P5 (after thawed) compared with the control. Accordingly, the DPMSCs of the invention encompass an isolated population of DPMSCs that have telomere length of less than 75% of the control cell line, preferably less than about 65%, preferably less than about 55%, and more preferably less than about 45%.

The population of DPSMCs of the invention have the capability to differentiate into one or more (such as two or all three) of the cell types of ectodermal, endodermal, or mesodermal lineages. In another aspect, the population of DPMSCs of the invention have the capability to differentiate into any one or more of the following: osteoblast, skeletal muscle cell, smooth muscle cell, cardiac muscle cell, glial cell, neuronal cell and hepatic cell. In another aspect, the population of DPSMCs of the invention have the capability to differentiate into any one or more of the following: a bone cell, skeletal muscle cell, smooth muscle cell, cardiac muscle cell, glial cell, neuronal cell, skin epithelial cell, liver epithelial cell, pancreas epithelial cell, pancreas endocrine cell, pancreatic islet cell, pancreas exocrine cell, gut epithelium cell, kidney epithelium cell, epidermal associated structure, hair follicles, soft tissues surrounding teeth, dentin (teeth), enamel (teeth), and cement (teeth). The invention contemplates any and all of the above parameters, as described in the above sections and elsewhere herein, in any combination, to describe and characterize the DPMSCs.

IV. Method of Isolating and/or Culturing Dental Pulp Marrow Similar Cells

Dental pulp marrow similar cells (DPMSCs) isolated as described herein may be cultured using methods of the invention starting from a source of dental pulp as described above. The dental pulp can be either enzymatically disaggregated or non-enzymatically disaggregated (e.g., mechanical disaggregation). In one aspect, the disgregated mixed population of cells are not subjected to any type of depletion techniques (e.g., immunodepletion or physical or chemical depletion). In another aspect, the methods do not involve depleting cells (e.g., mononuclear cells) expressing the following markers: CD3, CD14, CD19, CD38, CD66b and CD45$^+$ glycophorin A.

The cells can then be plated in, from example, one or more of any type of culturing vessel, such as a plastic culture dish, and maintained in a proliferation medium that is supplemented with various growth factors. The growth factors may be chosen from platelet-derived growth factor (e.g., PDGF-BB), epidermal growth factor (EGF), fibroblast growth factor-b (FGF-b), insulin-like growth factor (IGF), insulin, dexamethasone, linoleic acid, ascorbic acid, and selenium to obtain a population of DPMSCs. In one embodiment, the medium may be supplemented with all of these components. In one embodiment, the proliferation medium is described in the Examples and is referred to here in Mid-free medium. The growth factors which can be used include, but are not limited to, 1-50 ng/ml (preferably about 5-15 ng/ml) platelet-derived growth factor-BB (PDGF-BB), 1-50 ng/ml (preferably about 5-15 ng/ml) epidermal growth factor (EGF), 1-50 ng/ml (preferably about 5-15 ng/ml) insulin-like growth factor (IGF), 50 ng/ml (preferably about 5-15 ng/ml) fibroblast growth factor-b (FGF-b), with $10^{-10}$ to $10^{-8}$ M dexamethasone or other appropriate steroid, 0-1 μg/IL linoleic acid, and 10-50 mg/L ascorbic acid.

In another aspect of the invention, the DPMSCs of the invention are cultured in media that comprises insulin at a concentration of about 10 to about 50 μg/ml, transferrin at a concentration of greater than 0 but less than about 10 μg/ml, selenium at a concentration of about 0.1 to about 5 μg/ml, linoleic acid at a concentration of about 0 to about 1 μg/m, dexamethasone at a concentration of about 0.005 to 0.15 μM, L-ascorbic acid at a concentration of about 10-50 mg/L, platelet-derived growth factor at a concentration of about 5 to about 15 ng/ml, epidermal growth factor at a concentration of about 1 to 15 ng/ml, insulin-like growth factor at a concentration of 1 to about 15 ng/ml, and ml and fibroblast growth factor-b1 to at a concentration of about 15 ng/ml.

In another aspect of the invention, the DPMSCs of the invention are cultured in media that comprised of a proliferation medium containing F-12 Coon's modified/Ambesi's modified/Medium 199/CMRL 1066 supplemented with about 1.25% of Human serum, platelet-derived growth factor-BB at a concentration of about 1 to about 50 ng/ml, epidermal growth factor at a concentration of about 1 to about 50 ng/ml, insulin-like growth factor-I at a concentration of about 1 to about 50 ng/ml, fibroblast growth factor-I at a concentration of about 1 to about 50 ng/ml, dexamethasone at a concentration of about $10^{-10}$ to about $10^{-8}$ M, linoleic acid at a concentration of about 20 to about 100 µg/L, ascorbic acid at a concentration of about 10 to about 50 mg/L and gentamycin at a concentration of about 0.5 ml/L. In another aspect of the invention, DPMSCs are placed, optionally dissociated, in a medium containing Collagenase II at a concentration at about 1000 U/mL and a CTC solution. The CTC solution contains Trypsin at a percentage by volume of about 0.5%, Collagenase II at a concentration of about 22 U/mL and chicken serum at a percentage by volume of about 0.2%. In yet another aspect of the invention, dental pulp population of cells is not subjected to any type of depletion techniques (e.g., immunodepletion or physical or chemical depletion) and when colonies develope in primary culture reaches confluence, cells can be detached by the CTC solution and sub-cultured in the proliferation medium. The culture is maintained semi-confluently to prevent cell differentiation.

In one alternative, the DPMSCs can be placed in a cell culture container with an extracellular matrix (ECM) substrate. In another alternative, the DPMSCs can be placed in a cell culture container without an extracellular matrix (ECM) substrate. In yet another alternative, the DMPSCs can be placed in a cell culture container such that it settles and forms a three-dimensional structure. As is known to one of skill in the art, three-dimensional structures, such as scaffolding (including bioscaffolding), can be used to culture the DPMSCs and/or differentiate the DPMSCs to cells and/or tissues. For example, the DPMSCs can be cultured with scaffolding to grow trachea, blood cells, brain tissue, kidney, pancreas, liver, heart, lung, spinal cord, nerve(s), neural cells, neurons, cartilage, bone, and other cells and/or tissues that could be used in regenerative medicine.

Culture in low-serum medium is preferred to maintain the cells in the undifferentiated state. Serum can be human serum or non-human serum, depending on the species of DPMSCs being isolated. Human serum can be autologous. Low serum as used herein refers to a level by percentage by volume of about 0.5-2.5%. In one aspect, the present invention provides for methods for isolating DPMSCs and subsequent proliferation thereof that involve adding a low 1.25% human serum medium containing insulin, selenium, linoleic acid, dexamethasone, and platelet derived growth factor. The low-human serum medium may be F12 in admixture with M-199 and CMRL-1066. The insulin may be optionally present at a concentration of from about 1 to about 5 µg/ml. Low serum medium may contain an effective amount of transferrin at a concentration of greater than 0 but less than about 10 µg/ml, the selenium may be present at a concentration of about 0.1 to about 5 µg/L, the linoleic acid may be present at a concentration of 0 to about 1 µg/mL, and the dexamethasone may be present at a concentration of about $10^{-10}$ to $10^{-8}$ M. The low-serum medium may contain about 10-50 mg/L-ascorbic acid. The low-serum medium may contain about 5 to about 15 ng/ml platelet-derived growth factor, 1 to about 15 ng/ml epidermal growth factor, 1 to about 15 ng/ml insulin-like growth factor, and 1 to about 15 ng/ml fibroblast growth factor-b. The invention also contemplates the use of serum-free media with the addition of any one or all of the growth factors components listed above.

One of skill in the stem cell art can routinely culture the DPMSCs of the invention by using the media conditions described herein for proliferation. Once established in culture, cells can be frozen and stored as frozen stocks. In one embodiment, the cells are frozen and stored using the proliferation medium described herein with 10% DMSO. Other methods for preparing frozen stocks for cultured cells are also known to those of skill in the art. In addition to culturing DPMSCs for proliferation, the population of DPMSCs can also be cultured in media with other factors added to induce differentiation into progeny cells.

The invention also includes DPMSC populations produced by the culturing method(s) described herein. The invention also includes cells cultured under conditions described herein, including cells initially cultured (for example, upon introduction into culture media) and along any point of the culture process.

In another aspect of the invention, a population of dental pulp cells with broad differentiation potential, as well as mesodermal-, endodermal-, and ectodermal-derived lineages can be isolated via the unique expansion/selection procedure presented in the invention, which involves the use of low percentages of autologous human serum.

III. Inducing DPMSCs to Differentiate to Form Committed Progenitors and Tissue-Specific Cell Types and Uses Thereof The present invention further provides for differentiated cells derived from the pluripotent DPMSCs described herein as well as methods to induce differentiation of these cells. In one aspect, the invention encompasses DPMSCs which can differentiate into any one or more of the following: splanchnic mesoderm cells, muscle cells, neuronal cells, cardiomyocytes and hepatocytes. In another aspect, the invention encompasses DPMSCs which can differentiate into any one or more of the following: a bone cell, skeletal muscle cell, smooth muscle cell, cardiac muscle cell, glial cell, skin epithelial cell, liver epithelial cell, pancreas epithelial cell, pancreas endocrine cell or islet cell, pancreas exocrine cell, gut epithelium cell, kidney epithelium cell, or an epidermal associated structure (e.g., hair follicle). In another aspect, the invention encompasses DPMSCs which can differentiate into progeny cells that can form soft tissues surrounding teeth or may form teeth (e.g., dentin, enamel and cement). In yet another aspect, the invention encompasses DPMSCs which can differentiate into any one or more of the following: osteoblast cells and myocytes.

The present invention also provides for isolated pluripotent DPMSCs as described herein, wherein genome of the cell has not been altered by insertion of pre-selected isolated DNA, by substitution of a segment of the cellular genome with preselected isolated DNA, or by deletion of or inactivation of at least a portion of the cellular genome.

Using appropriate growth factors, chemokines, and cytokines as described herein and/or also known to one of skill in the art, DPMSCs of the present invention can be induced to differentiate to form a number of cell lineages, including, for example, a variety of cells of mesodermal origin as well as cells from neuroectodermal origin (e.g., glial cells, oligodendrocytes, and neurons) as well as endodermal origin (e.g., hepatocytes). The invention encompasses these methods.

A. Splanchnic Mesoderm

Splanchnic mesoderm may be grown by using the homogeneous population of DPMSCs of the invention. In one embodiment, to grow osteoblasts, 20,000 cells/cm$^2$ of DPMSCs can be cultured with about $10^{-6}$ to $10^{-8}$ M (preferably about 100 nM) dexamethasone, β-glycerophosphate and 0.5-3 mM (preferably 1 mM) ascorbic acid. To demonstrate presence of osteoblasts, Von Kossa staining (silver reduction of CaPo4) can be used, or antibodies against osteonectin, osteopontin and osteocalcin (immunohistochemistry/Western/rt-PCR), after about 3 months of culture. X-Ray diffraction patterns and infrared spectra can also be used to evaluate the presence of Hydroxyapatite formation.

B. Muscle

DPMSCs can be induced to undergo differentiation to any muscle phenotype by plating confluent DPMSCs prior to induction of differentiation. In one aspect, to induce muscle cell differentiation, about 10,000 cells/cm$^2$ DPMSCs cells can be treated with DMEM 5% FBS with IBMX 0.1-1 mM (preferably 0.5 mM) and VEGF 5-20 ng/mL (preferably 10 ng/mL). Differentiation can be evaluated by using Western blot and immunofluorescence. Skeletal muscle differentiation in vitro can be demonstrated by detecting sequential activation of myogenin, actinin, skeletal actin and skeletal myosin, either by immunohistochemistry or Western blot analysis using standard techniques known to those of skill in the art and commercially available antibodies. Skeletal actin, Serca 2a, Ca-channel and Msx-2 can be detected as early as 15 days after induction, and skeletal myosin at 40 days. By immunohistochemistry, about 70-80% of cells can express mature muscle proteins after 14 days. Treatment with differentiation medium can result in the expression of ASA, Ca-channel, SMA, c-TnT, Connexin-43, Gata-4, Myosin heavy chain, Myogenin, Nkx-2.5, N-caderin, Serca-2a ATPase during the 15 days of culture. In addition, skeletal myosin can be organized and co-expressed with ASA at 40 days, like actinin. Smooth muscle actin can be detected at two days after induction and can persist. Ryanodine receptor may not be expressed.

C. Neuronal Cells

DPMSCs can be induced to undergo differentiation to neuronal cells. As further detailed in the Examples for one embodiment, neural development can be induced by culturing DPMSCs in neural differentiation medium. Neural differentiation medium can include a minimum essential medium, such as DMEM-HG. Neural differentiation medium typically contains one or more additional additives, such as antibiotics, growth factors, nutrients, or combinations thereof. Specific non-limiting examples of such additives include NT-3 (from about 1 ng/ml to about 100 ng/ml), NGF (from about 1 ng/ml to about 100 ng/ml), BDNF (from about 5 ng/ml to about 500 ng/ml), insulin (from about 0.1 μg/ml to about 10 μg/ml), IBMX (from about 0.1 μM to about 100 μM) and indomethacin (from about 10 μM to about 500 μM). In another aspect, this medium can include any one or more of the following: DMEM-HG, 1×ITS, and FGF (e.g., at about 0.5-100 ng/mL, preferably about 10 ng/mL). The medium may also contain one or more of the following cytokines in order to induce differentiation into certain cell types: 5-50 ng/mL BDNF (preferably about 16 ng/mL) for obtaining dopaminergic neurons. The choice of growth factors to induce differentiation of DPMSCs into neural cells can be based on what is known in embryonic development of the nervous system or from studies that evaluated in vitro CNS differentiation.

In one aspect of the invention, neural specification is induced by incubating DPMSC cells at about 3,000 cells/cm$^2$ in DMEM-high glucose with 10% FBS. Medium is replaced after 24 hours with a neural commitment medium containing DMEM-high glucose, 10% FBS with B27, EGF at a concentration of about 10 ng/ml and bFGF at a concentration of about 20 ng/ml for 15 days. Cells are passed 1:3 and placed in the neural commitment medium with NT-3 at a concentration of about 20 ng/ml, NGF at a concentration of about 20 ng/ml, BDNF at a concentration of about 50 ng/ml, BHA at a concentration of about 20 μM, IBMX at a concentration of about 50 μM, ATRA at a concentration of about 1 μM, and Progesteron at a concentration of about 20 nM.

In another aspect of the invention, neural differentiation is induced by contacting neurally committed cells with a neural differentiation medium that consists of DMEM, NT-3 at a concentration of about 20 ng/ml, NGF at a concentration of about 20 ng/ml, BDNF at a concentration of about 50 ng/ml, insulin at a concentration of about 5 μg/ml, indomethacin at a concentration of about 200 μM, and IBMX at a concentration of about 0.5 mM. Neurally committed DPMSC cells are incubated in the neural differentiation medium for about 1 day.

In one aspect of the invention, DPMSC cells can be allowed to settle to the bottom of the culture dish to form a 3D structure. Neural differentiation may be expected to occur, for example, in a 100% humidified atmosphere of 95% air, 5% CO2 at 37°. Neural differentiation may be detected in about 4 weeks. In another aspect of the invention, the morphology of the neural-induced DPMSC cells closely resembled that of mature neurons: they had a large number of neurites, increased from about 3 to about 4 weeks after differentiation, and with significant branching.

After about 2-4 weeks, the culture of cells can be examined to determine the growth of astrocytes and neurons. Astrocytes can be identified as glial-fibrilar-acidic-protein (GFAP) positive cells, oligodendrocytes can be identified as glucocerebroside positive (Gal C) and neurons can be identified as cells that express in a sequential fashion NeuroD, Tubulin-IIIB (Tuji), synaptophysin and neurofilament-68, 160-200 kDa.

In one non-limiting example, the number of neurites per neuron can increase from 3±1, to 5±1 and 7±2 from 2, 3 to 4 weeks after differentiation. Differentiation to cells with characteristics of neurons can be confirmed by demonstrating presence of GFAP, neurofilament-160, synaptophysin, β$^3$-Tubulin by Western blot. The use of immunofluorescence can reveal the presence of synaptophysin, Synapsyn I, Neurofilament 160, β$^3$-Tubulin, N-caderin, Tyrosine hydroxylase, Neuro-D, N-Cadherin, Neurofilament-68, and NSE.

The use of rt-PCR can show that cells express β$^3$-Tubulin, Neurofilament-68, -160, -200 kDa, vimentin, NSE, β$^3$-Tubulin, G-Fap, Glypican, Musashi, n-Nos, but not MAP-2. Other growth factors that are specifically expressed in the brain and that can affect neural development in vivo and in vitro include brain derived neurotrophic factor (BDNF), glial derived neurotrophic factor (GDNF) and ciliary neurotrophic factor (CNTF). BDNF is a member of the nerve growth factor family that promotes in vitro differentiation of NSC, human subependymal cells, and neuronal precursors to neurons and promotes neurite outgrowth of hippocamal stem cells in vivo. In one non-limiting example, DPMSCs treated with 5-20 ng/mL (preferably 16 ng/mL) BDNF and EGF could differentiate into tyrosine hydroxylase positive neurons, consistent with the known function of BDNF to support survival of dopaminergic neurons of the substantia nigra.

In one aspect of the invention, neural stem precursor marker, Vimentin, is expressed both in proliferation and neural differentiation, but during the induction, it is less organized. Neuro-endocrine nuclear factor, Neuro-D/Beta-2, is expressed only during proliferation. Expression of Nestin, another neurofilament neural stem marker, is decreased from proliferation to the induction stage. $\beta^3$-Tubulin is expressed in about 99% of DPMSC cells after differentiation. Structural neurofilaments NF-160 and NF-200 are expressed only during differentiation, the positivity of expression is about 50% for NF-160 and to a lesser extent for NF-200, which is consistent with a mature neural phenotype. In contrast, NF-68 protein is expressed during proliferation and after neural induction, as shown for NSE.

In another aspect of the invention, synaptic vesicle trafficking markers Synapsyn-I and synaptophysin are expressed after differentiation in all neural induced DPMSC cells, at the same time, Tyrosine hydroxylase, N-caderin, and p75-NGFr are detected only after induction. The Oligodendrocyte marker-4 is not expressed. G-Fap, astrocyte marker, is expressed during both proliferation and neural differentiation, but is less organized during induction. GFAP and beta3-tubulin are co-expressed.

D. Cardiomyocytes

Differentiation to cardiomyocytes can be achieved by plating confluent DPMSC prior to induction of differentiation. In one aspect, to induce cardiomyocyte cell differentiation, confluent (e.g., 10,000 cells/cm$^2$) DPMSC cells can be treated with DMEM HG with FBS (from about 1% to about 10%), IBMX (from about 0.1 mM to about 10 mM), and VEGF (from about 1 ng/ml to about 20 ng/ml) and cultured at condition favorable to the differentiation, for example, in a 100% humidified atmosphere of 95% air, 5% CO$_2$ at 37°. Cardiomyocyte differentiation may be detected between about 2 weeks to about 3 months. Muscle differentiation in vitro can be demonstrated by detecting sequential activation of actinin, skeletal and cardiac actin and skeletal myosin, either by immunohistochemistry or Western blot and rt-PCR analysis using commercially available antibodies and specific primers. Expression of ASA, Ca-channel DHPR, SMA, c-TnT, Connexin-43, Msx-2, Myosin heavy chain, Gata-4, Serca 2A can also be determined as an indication of differentiation down the cardiomyocyte pathway.

In another aspect of the invention, differentiation to any muscle phenotype can be achieved by plating DPMSC at 11,000 cells/cm$^2$ prior to induction of differentiation. To induce cardiomyocyte cell differentiation, confluent DPMSC cells can be treated with DMEM with about 5% FCS, bFGF at a concentration of about 10 ng/mL, VEGF at a concentration of about 10 ng/mL, and IGF-1 at a concentration of about 10 ng/mL. Cells can be cultured to reach confluency for about 2 weeks to about 3 months with medium exchanges every 4 days.

Cardiomyocyte differentiation may be expected to occur, for example, in a 100% humidified atmosphere of 95% air, 5% CO2 at 37°. In one aspect of the invention, cardiomyocyte differentiation may be detected between about 2 weeks to about 3 months. During this differentiation period, cells became long and irregular. Co-expression of Atrial natriuretic peptide (ANP), Smooth muscle actin (SMA), Skeletal muscle actin (SKMA), Cardiac actin (CA), cardiac-Troponin T (c-TNT). Miocyte enhancer factor-2a (MEF-2a), and Myosin heavy chain (Mhc) can be detected during proliferation and differentiation.

In another aspect of the invention, mRNA expression level of Gata-4 and Nkx-2.5 is low in both proliferation and differentiation phases, whereas Msx-2 m-RNA expression is high. Expression of Myocardin decreases after differentiation. In yet another aspect of the invention, cells can organize filaments of α-actinin, α-sarcomeric actin and Myosin heavy chain. α-sarcomeric actin and Myosin heavy chain can be co-expressed and organized in a fraction of differentiating cells.

In one aspect of the invention, gap-junctions can be demonstrated by the presence of connexin-43 in proximity to cell to-cell contact sites. L-Type calcium channels, Serca-2 ATPase pump, c-TNT can also be identified in differentiated cells. SMA can be expressed at high level during the proliferation stage and the expression decreases after induction without losing the filamentous structure. Expression of Msx-2 decreases constantly from proliferation to differentiation stage, whereas GATA-4 expression is lost after cardiomyocyte induction.

E. Hepatic Cells

In one aspect, differentiation to hepatic cells can be achieved by plating confluent (e.g., 20,000 cells/cm$^2$) DPMSC prior to induction of differentiation with DMEM low glucose 1-10% FCS, hepatocyte growth factor (HGF) (from about 1 ng/ml to about 100 ng/ml), oncostatin (OSM) (from about 1 ng/ml to about 100 ng/ml), nicotinamide (from about 1 mM to about 100 mM), LDL (from about 0.1 μg/ml to about 10 ng/ml), FGF-4 (from about 1 ng/ml to about 100 ng/ml), insulin (from about 1 μg/ml to about 10 μg/ml), linoleic acid (from about 180 μg/L to about 1 mg/L), and glucose (from about 1 g/L to about 10 g/L) and cultured under conditions favorable to the differentiation. One of skill in the art can ascertain the differentiation pathway to hepatic cells by observing small epitheloid cells that express and secrete albumin. In addition, the cells can be tested for expression of mRNA for HGF receptor, cytokeratin 19, Abcg-2, MDR-I, transferrin, somatostatin, erythropoietin, and cytochrome P-450 subunit 2e1. In addition, the presence and secretion of albumin, urea, cytokeratin-8-18-19, HNF-3β and HNF-4α may also indicate possible differentiation to hepatic cells.

In another aspect of the invention, hepatocyte differentiation can be achieved by incubating confluent DPMSCs with DMEM low glucose 1% FCS, hepatocyte growth factor at a concentration of about 20 ng/mL, Oncostatin at a concentration of about 10 ng/ml, Nicotinamide at a concentration of about 10 mM, LDL at a concentration of about 1.25 μg/mL, FGF-4 at a concentration of about 10 ng/mL, Insulin (from about 1 μg/ml to about 10 μg/ml), Linoleic acid at a concentration of about 0.00018 g/L and glucose at a concentration of about 1.25 g/L for about 14 to about 37 days. Hepatic differentiation may be expected to occur, for example, in a 100% humidified atmosphere of 95% air, 5% CO2 at 370, and hepatic differentiation may be detected after about 5 weeks.

In another aspect of the invention, after about 14 to about 37 days, differentiated cells can assume a globular shape with an eccentric nucleus. During proliferation to differentiation stage, these cells can show increased expression of Albumin, Transferrin, Somatostatin, Erytropoictin and Cytochrome P-450 subunit 2e1, constant expression of c-MET/HGF-r, Abcg-2, MDR-I, and decreased expression of cytokeratin-19. In yet another aspect of the invention, a large percentage of cells can be stained positive for the hepatic epiteliol specific cytokeratins 8, 18 and 19 after differentiation with a small filamentous organization. Cells can express both hepatocyte nuclear factor 4α and 3β, after hepatic induction. In another aspect, cells can acquire several hepatocytic functions such as the ability to store glycogen as demonstrated by PAS staining and to produce albumin and urea as examined by testing the concentration and dosage of these factors in culture supernatants.

IV. Kits Containing DPMSCs or DPMSC Isolation and Culture Components

DPMSCs of the present invention (and/or differentiated cells derived from DPMSCs of the invention) can be provided in kits, with appropriate packaging material. For example, DPMSCs can be provided as frozen stocks (in appropriate preservation media, for example, as described herein), accompanied by separately packaged appropriate factors and media, as previously described herein, for culture in the undifferentiated state. Additionally, separately packaged factors for induction of differentiation, as previously described, can also be provided.

Kits containing effective amounts of appropriate factors for isolation and culture of stem cells (such as those from a patient) are also provided by the present invention. Upon obtaining a dental pulp from an individual (such as a patient), the technician selects the stem cells using the method(s) described herein or using one or more selection tools based on the marker profile of the DPMSCs described herein (e.g., anti-CD45 and anti-glycophorin A) provided in the kit, then cultures the cells as described by the method(s) of the present invention, using culture medium supplied as a kit component. The composition of the basic culture medium has been previously described herein. The kits may also contain instructions addressing any one or more methods of culturing, differentiating, or using the cells as described herein.

V. Methods of Using DPMSCs and Differentiated Cells Derived from DPMSCs

DPMSCs of the invention have many uses, both in its undifferentiated state as well as in its differentiated state. The invention provides for methods of administering DPMSCs to an individual in need of such treatment. Accordingly, in some aspects of the invention, DPMSCs can be adminstered the individual for therapeutic assistance. In all of the conditions listed below, it is to be understood that the DPMSCs and differentiated cells derived from the DPMSCs can not only be used for treatment purposes but also to assist in the therapy for the conditions. One of skill in the art may readily determine the appropriate state (differentiated vs. undifferentiated) that a population of DPMSCs should be in when the population is being used, for example, for therapeutic purposes to treat a condition (e.g., tissue repair and/or assisting or aiding treatment). In some circumstance, the DPMSCs is used in its undifferentiated, pluripotent state. The DPMSCs may be optionally manipulated (e.g., genetically) to provide added benefits to the individual. In other instances, it may be appropriate to culture the DPMSCs in a manner to induce differentiation down a particular pathway where the individual in need of could benefit from such cells.

DPMSCs, and the medium used for DPMSC selection of the present invention, hold strong promise in clinical reparative medicine for the treatment of degenerative or inherited diseases and are free of the ethical concerns raised by the use of ES cells. Autologous ex vivo expanded DPMSC cells could be used for autologous implantation aimed to repair damaged, aged or diseased tissues and organs. The ability to stably transduce DPMSC cells with specific genes, can also enable the genetic manipulation of autologous cells for the treatment of degenerative and congenital disorders.

DPMSCs of the present invention that have been induced to differentiate to form bone cells can be used as cell therapy and/or assist cell therapy for tissue regeneration in osteoporosis, Paget's disease, bone fracture, osteomyelitis, osteonecrosis, achondroplasia, osteogenesis imperfecta, hereditary multiple exostosis, multiple epiphyseal dysplasia, Marfan's syndrome, mucopolysaccharidosis, neurofibromatosis or scoliosis, reconstructive surgery for localized malformations, spina bifida, hemivertebrae or fused vertebrae, limb anomalies, reconstruction of tumor-damaged tissue, and reconstruction after infection, such as middle ear infection.

DPMSCs can be induced to differentiate to form skeletal muscle cells for cell therapy and/or assist cell therapy for tissue repair in the treatment of Duchene muscular dystrophy, Becker muscular dystrophy, myotonic dystrophy, skeletal myopathy, and reconstructive surgery to repair skeletal muscle damage. DPMSCs can be induced to differentiate to form smooth muscle cells for cell therapy or tissue repair in the treatment of developmental abnormalities of the gastrointestinal system, such as oesophageal atresia, intestinal atresia, and intussusception, as well as for replacement of tissues after surgery for bowel infarction or colocolostomy. Smooth muscle cells formed from the DPMSCs of the present invention can also be used for bladder or uterine reconstruction, for neovascularization, for repair of vessels damaged by, for example, atherosclerosis or aneurysm. Smooth muscle precursor cells (mesangial cells) can be used as an in vitro model for glomerular diseases or for cell therapy or tissue regeneration in diabetic neuropathy. Smooth muscle precursors can also be used to repair macula densa of the distal convoluted tubule or juxtaglomerular tissues, which play a role in blood pressure regulation.

Cardiomyocytes derived from the DPMSCs can be useful for cell therapy and/or assist cell therapy for tissue repair for treating heart tissue damaged following myocardial infarction, in conjunction with congestive heart failure, during valve replacement, by congenital heart anomalies, or resulting from cardiomyopathies or endocarditis. Cells can be delivered locally, especially by injection, for increased effectiveness.

Microglial cells differentiated from DPMSCs can be used to treat spinal cord injuries and neurodegenerative disorders, such as Huntingtons disease, Parkinsons disease, Multiple Sclerosis, and Alzheimers disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury.

Microglial cells differentiated from DPMSCs can be induced to differentiate into neuroectodermal cells and used to treat spinal cord injuries and neurodegenerative disorders, such as Huntingtons disease, Parkinsons disease, Multiple Sclerosis, and Alzheimers disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury. DPMSCs induced to form oligodendrocytes and astrocytes, for example, can be used for transplant into demyelinated tissues, especially spinal cord, where they function to myelinate the surrounding nervous tissues. This technique has been demonstrated effective in mice, using embryonic stem cells as the source of oligodendrocyte and astrocyte precursors (Brustle, O., et al., Science (1999) 285: 754-756). The DPMSCs of the present invention can exhibit the broad range of differentiation characteristic of embryonic cells, but provide the added advantage of contributing autologous cells for transplant. Accordingly, the DPMSCs of the invention or its neuronally related differentiated cell can be used to treat a disease with neural deficits or degeneration including among but not limited to stroke, Alzheimer's, Parkinson's disease, Huntington's disease, AIDS-associated dementia, spinal cord injury, and metabolic diseases effecting the brain or other nerves.

Other uses for the cells of the invention include providing therapeutic enzymes, proteins, or other biological products by performing an in utero transplantation of a population of the DPMSCs to form chimerism of cells or tissues to produce human cells in prenatal or post-natal humans or animals following transplantation, wherein the cells produce therapeutic enzymes, proteins, or other biological products in the human or animal so that genetic defects are corrected.

The present invention includes methods of providing therapy for damaged tissue in a human individual in need thereof comprising: (a) culturing the DMPSCs to proliferate them; and (b) contacting an effective amount of the expanded DPMSCs with the damaged tissue of said individual to aid therapy. The cells may be introduced into the body of the individual by localized injection, or by systemic injection. The cells may be introduced into the body of the individual in conjunction with a suitable matrix implant. The matrix implant may provide additional genetic material, cytokines, growth factors, or other factors to promote growth and differentiation of the cells. The cells may be encapsulated prior to introduction into the body of the individual, such as within a polymer capsule.

The present invention also provides methods of using DPMSCs to identify genetic polymorphisms associated with physiologic abnormalities, involving isolating the DPMSCs from a statistically significant population of individuals from whom phenotypic data can be obtained, expanding the DPMSCs from the statistically significant population of individuals to establish DPMSC cultures, identifying at least one genetic polymorphism in the cultured DPMSCs, inducing the cultured DPMSCs to differentiate, and characterizing aberrant metabolic processes associated with said at least one genetic polymorphism by comparing the differentiation pattern exhibited by DPMSCs having a normal genotype with the differentiation pattern exhibited by DPMSCs having an identified genetic polymorphism.

The present invention further provides methods for treating cancer (or in some embodiments, methods of delivering a therapeutic protein to an individual with cancer), in an individual by genetically altering DPMSCs to express a tumoricidal protein, an anti-angiogenic protein, or a protein that is expressed on the surface of a tumor cell in conjunction with a protein associated with stimulation of an immune response to antigen, and introducing an amount of the genetically altered DPMSCs into the individual effective to generate an anti-cancer effect (e.g., modify cultured cells and use them in different ways to halt growth of or kill cancer cells).

The present invention provides methods of using DPMSCs to characterize cellular responses to biologic or pharmacologic agents by isolating DPMSCs from a statistically significant population of individuals, expanding the DPMSCs from the statistically significant population of individuals to establish a plurality of DPMSC cultures, contacting the DPMSC cultures with one or more biologic or pharmacologic agents, identifying one or more cellular responses to the one or more biologic or pharmacologic agents, and comparing the one or more cellular responses of the DPMSC cultures from individuals in the statistically significant population.

In another aspect, the DPMSCs cells of the invention can be used to produce tooth component material for treatment of dental disease. In another aspect, the DPMSCs cells of the invention can be used to develop skin epithelial tissue derived from pluripotent stem cells that can be utilized for skin grafting and plastic surgery. In another aspect, the DPMSCs cells of the invention can be used to enhance muscle, such as in the penis or heart. In another aspect, the DPMSCs cells of the invention can be used to produce blood ex vivo for therapeutic use, or to produce human hematopoietic cells and/or blood in prenatal or post natal animals for human use. In another aspect, the DPMSCs cells of the invention can be used as a therapeutic to aid in the recovery of a patient from chemotherapy or radiation therapy in treatment of cancer, in the treatment of autoimmune disease, to induce tolerance in the recipient. In another aspect, the DPMSCs cells of the invention can be used to treat AIDS or other infectious diseases.

In another aspect, the DPMSCs cells of the invention can be used to treat cardiac diseases including, but not limited to, myocarditis, cardiomyopathy, heart failure, damage caused by heart attacks, hypertension, atherosclerosis, and heart valve dysfunction. A genetically engineered pluripotent mammalian derived stem cell, or its differentiated progeny, can be used to treat a disease associated with CNS deficits or damage.

A population of DPMSCs or their differentiated progeny such as stromal cells can be used to support the growth and differentiation of other cell types in vivo or in vitro, including but not limited to hematopoietic cells, pancreatic islet or beta cells, hepatocytes, etc. The stem cell, or cartilage differentiated progeny, can be used to treat a disease of the joints or cartilage including but not limited to cartilage tears, cartilage thinning, and osteoarthritis. Moreover, the stem cells or their osteoblast differentiated progeny can be used to aid amelioration of a process having deleterious effects on bone including among but not limited to bone fractures, non-healing fractures, osteoarthritis, "holes" in bones caused by tumors spreading to bone such as prostate, breast, multiple myloma etc.

The present invention also encompasses methods of providing for a database of at least one gene profile of DPMSCs as described herein, and the use of this databank to aid in drug discovery. Accordingly, in one aspect, the invention provides for methods of providing a database of gene profiles of a pluripotent derived stem cell to aid in drug discovery by: (a) determining the gene profile from DPSMCs from at least one individual, wherein the gene profile involves at least one gene; and (b) storing the gene profile(s) on an accessible medium.

The cells of the present invention can be used in cell replacement therapy and/or gene therapy to treat congenital neurodegenerative disorders or storage disorders such as, for instance, mucopolysaccharidosis, leukodystrophies (globoid-cell leukodystrophy, Canavan disease), fucosidosis, GM2 gangliosidosis, Niemann-Pick, Sanfilippo syndrome, Wolman disease, and Tay Sacks. They can also be used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

The present invention also provides methods of using specifically differentiated cells for therapy comprising administering the specifically differentiated cells to an individual in need thereof. It further provides for the use of genetically engineered pluripotent stem cells to selectively express an endogenous gene or a transgene, and for the use of DPMSCs grown in vivo for transplantation/administration into an individual to treat a disease. For example, neuroretinal cells derived from pluripotent stem or DPMSCs can be used to treat blindness caused by, but not limited to, neuroretinal disease caused by, but not limited to, macular degeneration, diabetic retinopathy, glaucoma, or retinitis pigmentosa. The cells can be used to engraft a cell into an individual comprising administering autologous, allogenic or xenogenic cells, to restore or correct tissue specific metabolic, enzymatic, coagulation, structural or other function to the mammal. The cells can be used to engraft a cell into an individual, causing the differentiation in vivo of cell types, and for administering the differentiated stem cells into the mammal. The cells, or their in vitro or in vivo differentiated progeny, can be used to correct a genetic disease, degenerative disease, cardiovascular disease, metabolic storage disease, neural, or cancer disease process.

Several approaches may be used for transplantation to prevent immune rejection. For universal donor cells: DPMSC can be manipulated to serve as universal donor cells for cell and gene therapy to remedy genetic or other diseases and to replace enzymes. Undifferentiated DPMSCs express mRNA and very low protein percentages for HLA-type I, HLA-type II. DPMSCs can be modified to serve as universal donor cells by eliminating HLA-type I and HLA-type II antigens, and potentially introducing the HLA-antigens from the prospective recipient to avoid that the cells become easy targets for NK-mediated killing, or become susceptible to unlimited viral replication and/or malignant transformation. Elimination of HLA-antigens can be accomplished by homologous recombination or via introduction of point-mutations in the promoter region or by introduction of a point mutation in the initial exon of the antigen to introduce a stop-codon, such as with chimeroplasts. Transfer of the host HLA-antigen can be achieved by retroviral, lentiviral, adeno-associated virus or other viral transduction or by transfection of the target cells with the HLA-antigen cDNA's. DPMSCs can be used to establish and set amount or a given range or level of a protein in the body or blood.

For intrauterine transplant to circumvent immune recognition: DPMSCs can be used in intrauterine transplantation setting to correct genetic abnormalities, or to introduce cells that will be tolerated by the host prior to immune system development. This could be a way to make human cells, such as blood, in large quantities in animals or it could be used as a way to correct human embryo genetic defects by transplanting cells that make the correct protein or enzyme.

The present invention also provides for methods of using the DPMSCs for gene therapy in an individual in need of therapeutic treatment, involving genetically altering the cells by introducing into the cell an isolated pre-selected DNA encoding a desired gene product, expanding the cells in culture, and introducing the cells into the body of the individual to produce the desired gene product. Until now, human cells used for gene therapy have been essentially limited to bone marrow and skin cells, because other types of cells could not be extracted from the body, grown in culture, genetically altered, then successfully reimplanted into the patient from whom the tissue was taken. See, for example, Anderson, W. F., *Nature* (1998) 392: 30; Anderson, W. F., *Scientific American* (1995) 273: 1 5; Anderson, W. F. *Science* (1992) 256: 808-813). DPMSCs of the present invention can be extracted and isolated from the body, grown in culture in the undifferentiated state or induced to differentiate in culture, and genetically altered using a variety of techniques, especially viral transduction. Uptake and expression of genetic material is demonstrable, and expression of foreign DNA is stable throughout development. Retroviral and other vectors for inserting foreign DNA into stem cells are known to those of skill in the art. See, e.g., Mochizuki, H., et al., *J. Virol* (1998) 72(11): 8873-8883; Robbins, P., et al., *J. Virol.* (1997) 71(12): 9466-9474; Bierhuizen, M., et al., *Blood* (1997) 90(9): 3304-3315; Douglas, J., et al., *Hum. Gene Ther*. (1999) 10(6): 935-945; Zhang, G., et al., *Biochem. Biophys. Res. Commun*. (1996) 227(3): 707-711). Once transduced using a retroviral vector, enhanced green fluorescent protein (eGFP) expression persists in terminally differentiated muscle cells, and endothelium derived from the isolated DPMSCs, demonstrating that expression of retroviral vectors introduced into DPMSC persists throughout differentiation.

Hematopoietic stem cells, although limited in differentiation potential, demonstrate utility for gene therapy (see Kohn, D. B., *Curr. Opin. Pediatr*. (1995) 7: 56-63). The cells of the present invention provide a wider range of differentiated cell types which can retain transduced or transfected DNA when terminally differentiated, as demonstrated by the fact that terminally differentiated muscle cells, endothelium, and c-Kit positive cells retained enhanced green fluorescent protein expression although the retroviral vector had been introduced into the undifferentiated stem cell.

DPMSCs of the present invention provide other advantages over hematopoietic stem cells for gene therapy, as well. Stem cells of the present invention are relatively easy to isolate from bone marrow aspirates obtained under local anesthesia, easy to expand in culture, and easy to transfect with exogenous genes. Adequate numbers of hematopoietic stem cells for the same purpose must be isolated from at least one liter of marrow and the cells are difficult to expand in culture (see Prockop, D. J., *Science* (1997) 276: 71-74).

Candidate genes for gene therapy include, for example, genes encoding Apolipoprotein E (which has been correlated with risk for Alzheimer's disease and cardiovascular disease), MTHFR (variants of which have been associated with increased homocysteine levels and risk of stroke), Factor V (which has been correlated with risk of thrombosis), ACE (variants of which have been correlated with risk of heart disease), CKR-5 (which has been associated with resistance to HIV), HPRT (hypoxanthine-guanine phosphoribosyl transferase, the absence of which results in Lesch-Nyhan disease), PNP (purine nucleoside phosphorylase, the absence of which results in severe immunodeficiency disease), ADA (adenosine deaminase, the absence of which results in severe combined immunodeficiency disease), p21 (which has been proposed as a candidate gene for treatment for ataxia telangiectasia), p47 (the absence of which is correlated with lack of oxidase activity in neutrophils of patients with chronic granulomatous disease, GenBank accession number M55067 and M38755), Rb (the retinoblastoma susceptibility gene associated with tumor formation, GenBank accession number M15400). KVLQT1 (a potassium channel protein, with aberrant forms associated with cardiac arrhythmias, Genbank accession number U40990), the dystrophin gene (associated with Duchenne muscular dystrophy, GenBank accession numbers M18533, M17154, and M18026), CFTR (the transmembrane conductance regulator associated with cystic fibrosis, GenBank accession number M28668), phosphatidylinositol 3-kinase (associated with ataxia telangiectasia, GenBank accession number U26455), and VHL (loss or mutation of the protein is associated with Von-Hippel Lindau disease: Latif, F., et al., *Science* (1993) 260: 1317-1320). Other diseases which can be treated effectively using these genetically-altered cells include, Factor IX deficiency, adenosine deaminase deficiency (associated with severe combined immunodeficiency disease, or SCIDS), and diabetes, and deficiencies in glucocerebrosidase α-iduronidase.

These novel genes can be driven by an inducible promoter so that levels of enzyme can be regulated. These inducible promoter systems may include a mutated ligand binding domain of the human estrogen receptor (ER) attached to the protein to be produced. This would require that the individual ingests tamoxifen to allow expression of the protein. Alternatives are tetracyclin on or off systems, RU486, and a rapamycin inducible system. An additional method to obtain relative selective expression is to use tissue specific promoters. For instance in the brain, one can introduce a transgene driven by the neuron-specific enolase promoter (Ad-NSE) or the glial fibrillary acidic protein promoter (GFAP) promoter, which will allow almost exclusive expression in brain tissue. Likewise, endothelial expression only may be obtained by using the Tec promoter or the VE-cadherin promoter.

Genetically altered DPMSCs can be introduced locally or infused systemically. Human stem cells with more limited differentiation potential, when transfected with a gene for factor IX, secrete the protein for at least 8 weeks after systemic infusion into SCID mice. See, e.g., Keating, A., et al., *Blood* (1996) 88: 3921. DPMSCs of the present invention, having a broader differentiation potential than other non-embryonic stem cell, provide an added advantage for systemic or local administration, because they can migrate to a variety of tissues, where cytokines, growth factors, and other factors induce differentiation of the cell. The differentiated cell, now a part of the surrounding tissue, retains its ability to produce the protein product of the introduced gene.

In Parkinson's disease, for example, clinical trials have shown that mesencephalic dopamine neurons obtained from human embryo cadavers can survive and function in the brains of patients with Parkinson's disease. PET scans have indicated that $_{[18F]}$fluorodopa uptake in the area around the cell graft is increased after transplantation, and remains so for at least six years in some patients. See, e.g., Dunnett, S. and A. Biorklund, *Nature* (1999) 399 (Suppl.) A32-A-39; Lindvall, O., *Nature Biotech*. (1999) 17: 635-636; Wagner, J., et al., *Nature Biotech*. (1999) 17: 653-659. Unlike the embryonic cells, isolated DPMSCs as described by the present invention provide a ready supply of cells for transplant, yet maintain the differentiation potential that makes embryonic cell transplant therapy an attractive alternative for disease treatment.

For AIDS therapy, DPMSCs of the present invention can be genetically engineered to produce Rev M10, a transdominant negative mutant of Rev that blocks the function of a wild-type Rev produced in HIV-infected cells. See, e.g., Bevec, D. et al., *Proc. Natl. Acad. Sci. USA* (1992) 89: 9870-9874; Ranga, U., et al., *Proc. Natl. Acad. Sci. USA* (1998) 95(3): 1201-1206. Once induced to differentiate into hematopoietic lineage cells and introduced into the patient, DPMSCs can repopulate the HIV-infected patient's depleted T cell supply. Since the genetically altered cells possess the mutant Rev M110, they will most likely be resistant to the lethal effects of infection by most strains of HIV.

Genetically altered DPMSCs can also be encapsulated in an inert carrier to allow the cells to be protected from the host immune system while producing the secreted protein. Techniques for microencapsulation of cells are known to those of skill in the art, see, for example, Chang. P., et al., *Trends in Biotech*. (1999) 17(2): 78-83). Materials for microencapsulation of cells include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275 (Baetge, E., et al.), for example, describes improved devices and methods for long-term, stable expression of a biologically active molecule using a biocompatible capsule containing genetically engineered cells. Such biocompatible immunoisolatory capsules, in combination with the DPMSCs of the present invention, provide a method for treating a number of physiologic disorders, including, for example, diabetes and Parkinson's disease.

In the diabetic patient, for example, heterologous stem cells which have been genetically altered to produce insulin at physiologically therapeutic levels can be encapsulated for delivery within the patient's tissues. Alternately, autologous stem cells can be derived from the patient's own bone marrow aspirate for transduction with a retroviral vector as previously described. Once genetically altered to produce physiologically therapeutic levels of insulin, these cells can be encapsulated as described by Chang or Baetge and introduced into the patient's tissues where they remain to produce insulin for extended periods of time.

Another advantage of microencapsulation of cells of the present invention is the opportunity to incorporate into the microcapsule a variety of cells, each producing a biologically therapeutic molecule. DPMSCs of the present invention can be induced to differentiate into multiple distinct lineages, each of which can be genetically altered to produce therapeutically effective levels of biologically active molecules. DPMSCs carrying different genetic elements can be encapsulated together to produce a variety of biologically active molecules.

DPMSCs of the present invention can be genetically altered ex vivo to express one or more desired gene products. The DPMSCs can then be screened or selected ex vivo to identify those cells which have been successfully altered, and these cells can be reintroduced into the individual, either locally or systemically. Alternately, DPMSCs can be genetically altered and cultured to induce differentiation to form a specific cell lineage for transplant. In either case, the transplanted DPMSCs provide a stably-transfected source of cells that can express a desired gene product. Especially where the patient's own bone marrow aspirate is the source of the DPMSCs, this method provides an immunologically safe method for producing transplant cells. The method can be used for treatment of diabetes, cardiac myopathy, neurodegenerative disease, and adenosine deaminase deficiency, to name only a few of a multitude of examples. In diabetes, for example, DPMSCs can be isolated, genetically altered to produce insulin, then transplanted into the patient suffering from the disease. Where the disease is associated with autoimmunity, DPMSCs can be genetically altered to express either an altered MHC or no MHC in order to avoid immune surveillance. Suppression of MHC expression in transplanted pancreatic islet cells has been successfully performed using an adenoviral vector expressing the E3 region of the viral genome. Cells of the present invention can be stably transfected or transduced, as the inventors have demonstrated, and can therefore provide a more permanent source of insulin for transplant into a diabetic patient.

Donor DPMSCs, particularly if genetically altered to alter MHC expression, and autologous DPMSCs, if genetically altered to express the desired hemoglobin gene products, can be especially effective in cell therapy for the treatment of sickle cell anemia and thalassemia.

Methods for Genetically Altering DPMSCs

Cells isolated by the method described herein can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer.

DPMSCs can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Homologous Recombination

Calcium phosphate transfection, which relies on precipitates of plasmid DNA/calcium ions, can be used to introduce plasmid DNA containing a target gene or polynucleotide into isolated or cultured DPMSCs. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Since the cells of the present invention are isolated cells, microinjection can be particularly effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. This technique has been used effectively to accomplish germline modification in transgenic animals.

Cells of the present invention can also be genetically modified using electroporation. The target DNA or RNA is added to a suspension of cultured cells. The DNA/RNA-cell suspension is placed between two electrodes and subjected to an electrical pulse, causing a transient permeability in the cell's outer membrane that is manifested by the appearance of pores across the membrane. The target polynucleotide enters the cell through the open pores in the membrane, and when the electric field is discontinued, the pores close in approximately one to 30 minutes.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPC) can be added. A recommended reagent for liposomal transfer is Lipofectin®, (Life Technologies, Inc.), which is commercially available. Lipofectin®, for example, is a mixture of the cationic lipid N-[1-(2,3-dioleyloyx)propyl]-N—N—N-trimethyl ammonia chloride and DOPE. Delivery of linear DNA, plasmid DNA, or RNA can be accomplished either in vitro or in vivo using liposomal delivery, which may be a preferred method due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam®, (Promega). Cationic lipid-mediated gene transfer efficiency can be enhanced by incorporating purified viral or cellular envelope components, such as the purified G glycoprotein of the vesicular stomatitis virus envelope (VSV-G), in the method of Abe, A., et al. (J. Virol. (1998) 72: 6159 6163).

Gene transfer techniques which have been shown effective for delivery of DNA into primary and established mammalian cell lines using lipopolyamine-coated DNA can be used to introduce target DNA into DPMSCs. This technique is generally described by Loeffler, J. and Behr, J., *Methods in Enzymology* (1993) 217: 599-618.

Naked plasmid DNA can be injected directly into a tissue mass formed of differentiated cells from the isolated DPMSCs. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA.

Microprojectile gene transfer can also be used to transfer genes into DPMSCs either in vitro or in vivo. The basic procedure for microprojectile gene transfer was described by J. Wolff in *Gene Therapeutics* (1994) at page 195. Briefly, plasmid DNA encoding a target gene is coated onto microbeads, usually 1-3 micron sized gold or tungsten particles.

The coated particles are placed onto a carrier sheet inserted above a discharge chamber. Once discharged, the carrier sheet is accelerated toward a retaining screen. The retaining screen forms a barrier which stops further movement of the carrier sheet while allowing the polynucleotide-coated particles to be propelled, usually by a helium stream, toward a target surface, such as a tissue mass formed of differentiated DPMSCs. Microparticle injection techniques have been described previously, and methods are known to those of skill in the art (see Johnston, S. A., et al., *Genet. Eng.* (NY) (1993) 15: 225-236; Williams, R. S., et al., *Proc. Natl. Acad. Sci. USA* (1991) 88: 2726-2730; Yang, N. S., et al., *Proc. Natl. Acad. Sci. USA* (1990) 87: 9568-9572).

Signal peptides can be attached to plasmid DNA, as described by Sebestyen, et al. (*Nature Biotech.* (1998) 16: 80-85), to direct the DNA to the nucleus for more efficient expression.

Viral vectors are used to genetically alter DPMSCs of the present invention and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H., et al., *J. Virol.* (1998) 72: 8873-8883). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems.

A retroviral DNA vector is generally used with the packaging cell line to produce the desired target sequence/vector combination within the cells. Briefly, a retroviral DNA vector is a plasmid DNA which contains two retroviral LTRs positioned about a multicloning site and SV40 promoter so that a first LTR is located 5 to the SV40 promoter, which is operationally linked to the target gene sequence cloned into the multicloning site, followed by a 3 second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types was demonstrated by Martin, F., et al., (*J. Virol.* (1999) 73: 6923-6929), who used single-chain variable fragment antibody directed against the surface glycoprotein high-molecular-weight melanoma-associated antigen fused to the amphotropic murine leukemia virus envelope to target the vector to delivery the target gene to melanoma cells. Where targeted delivery is desired, as, for example, when differentiated cells are the desired objects for genetic alteration, retroviral vectors fused to antibody fragments directed to the specific markers expressed by each cell lineage differentiated from the DPMSCs of the present invention can be used to target delivery to those cells.

Lentiviral vectors are also used to genetically alter cells of the invention. Many such vectors have been described in the literature and are known to those of skill in the art. Salmons, B. and Gunzburg, W. H., "Targeting of Retroviral Vectors for Gene Therapy," *Hum. Gene Therapy* (1993) 4: 129-141. These vectors have been effective for genetically altering human hematopoietic stem cells (Sutton, R., et al., *J. Virol.* (1998) 72: 5781-5788). Packaging cell lines have been described for lentivirus vectors (see Kafri, T., et al., *J. Virol.* (1999) 73: 576-584; Dull, T., et al., *J. Virol.* (1998) 72: 8463-8471).

Recombinant herpes viruses, such as herpes simplex virus type I (HSV-1) have been used successfully to target DNA delivery to cells expressing the erythropoietin receptor (Laquerre, S., et al., *J. Virol.* (1998) 72: 9683-9697). These vectors can also be used to genetically alter the cells of the present invention, which the inventors have demonstrated to be stably transduced by a viral vector.

Adenoviral vectors have high transduction efficiency, can incorporate DNA inserts up to 8 Kb, and can infect both replicating and differentiated cells. A number of adenoviral vectors have been described in the literature and are known to those of skill in the art (see, for example, Davidson. B. L., et al., *Nature Genetics* (1993) 3: 219-223; Wagner, E., et al., *Proc. Natl. Acad. Sci. USA* (1992) 89: 6099-6103). Methods for inserting target DNA into an adenovirus vector are known to those of skill in the art of gene therapy, as are methods for using recombinant adenoviral vectors to introduce target DNA into specific cell types (see Wold, W., Adenovirus Methods and Protocols, Humana Methods in Molecular Medicine (1998), Blackwell Science, Ltd.). Binding affinity for certain cell types has been demonstrated by modification of the viral vector fiber sequence. Adenovirus vector systems have been described which permit regulated protein expression in gene transfer (Molin, M., et al., *J. Virol.* (1998) 72: 8358-8361). A system has also been described for propagating adenoviral vectors with genetically modified receptor specificities to provide transductional targeting to specific cell types (Douglas, J., et al., *Nature Biotech.* (1999) 17: 470-475). Recently described ovine adenovirus vectors even address the potential for interference with successful gene transfer by preexisting humoral immunity (Hofmann, C., et al., *J. Virol.* (1999) 73: 6930-6936).

Adenovirus vectors are also available which provide targeted gene transfer and stable gene expression using molecular conjugate vectors, constructed by condensing plasmid DNA containing the target gene with polylysine, with the polylysine linked to a replication-incompetent adenovirus. (Schwarzenberger, P., et al., *J. Virol.* (1997) 71: 8563-8571.)

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al., *Science* (1989) 243: 1188-1191; Bredenbeek, P. J., et al., *J. Virol.* (1993) 67: 6439-6446; and Frolov, I., et al., *Proc. Natl. Acad. Sci. USA* (1996) 93: 11371-11377.

The stem cells of the present invention can also be used for tissue repair. The inventors have demonstrated that DPMSCs of the present invention differentiate to form a number of cell types, including fibroblasts, osteoblasts, (skeletal muscle, smooth muscle, cardiac muscle) cells. For example, DPMSCs induced to differentiate into osteoblasts, by the method previously described herein, can be implanted into bone to enhance the repair process, to reinforce weakened bone, or to resurface joints.

Matrices are also used to deliver cells of the present invention to specific anatomic sites, where particular growth factors incorporated into the matrix, or encoded on plasmids incorporated into the matrix for uptake by the cells, can be used to direct the growth of the initial cell population. DNA can be incorporated within pores of the matrix, for example, during the foaming process used in the formation of certain polymer matrices. As the polymer used in the foaming process expands, it entraps the DNA within the pores, allowing controlled and sustained release of plasmid DNA. Such a method of matrix preparation is described by Shea, et al., in *Nature Biotechnology* (1999) 17: 551-554.

Plasmid DNA encoding cytokines, growth factors, or hormones can be trapped within a polymer gene-activated matrix carrier, as described by Bonadio, J., et al., *Nature Medicine* (1999) July 5(7):753-759. The biodegradable polymer is then implanted near a broken bone, for example, where DPMSCs are implanted and take up the DNA, which causes the DPMSCs to produce a high local concentration of the cytokine, growth factor, or hormone, accelerating healing of the damaged tissue.

Cells provided by the present invention, or DPMSCs isolated by the method of the present invention, can be used to produce tissues or organs for transplantation. Oberpenning, et al. (*Nature Biotechnology* (1999) 17: 149-155) reported the formation of a working bladder by culturing muscle cells from the exterior canine bladder and lining cells from the interior of the canine bladder, preparing sheets of tissue from these cultures, and coating a small polymer sphere with muscle cells on the outside and lining cells on the inside. The sphere was then inserted into a dog's urinary system, where it began to function as a bladder. Nicklason, et al., *Science* (1999) 284: 489-493, reported the production of lengths of vascular graft material from cultured smooth muscle and endothelial cells. Other methods for forming tissue layers from cultured cells are known to those of skill in the art (see, for example, Vacanti, et al., U.S. Pat. No. 5,855,610). These methods can be especially effective when used in combination with cells of the present invention, which have a broader range of differentiation than previously-described non-embryonic stem cells.

DPMSCs of the present invention can be used to repopulate heart muscle cells by either direct injection into the area of tissue damage or by systemic injection, allowing the cells to home to the cardiac tissues. This method can be particularly effective if combined with angiogenesis. Both the methods of injection and methods for promoting angiogenesis are known to those of skill in the art. The DPMSCs of the present invention provide a broader differentiation range to provide a more varied source of cells for cardiac or other tissue repair utilizing these techniques.

DPMSCs of the present invention are also useful, for example, for the purpose of repopulating the bone marrow after high dose chemotherapy. Prior to chemotherapy, a DPMSCs are obtained from the patient. Stem cells are isolated by the method of the present invention, and are grown in culture and induced to differentiate. A mixture of differentiated and undifferentiated cells is then reintroduced into the patient's bone marrow space. Clinical trials are currently underway using hematopoietic stem cells for this purpose. The DPMSCs of the present invention, however, provide the additional benefit of further differentiation to form cells that can replace those damaged by chemotherapy in other tissues as well as in bone marrow.

Alternatively, the method described by Lawman, et al. (WO 98/42838) can be used to change the histocompatibility antigen of stem cells from an allogeneic donor or donors. Using this method, panels of available bone marrow transplants can be generated for preparation of frozen stocks, storage, and administration to patients who are unable, as in leukemia patients, for example, to provide their own bone marrow for reconstitution.

Re-population of a patient's immune system cells or blood cells can be accomplished, for example, by isolating autologous stem cells from the patient, culturing those cells to expand the population, then reintroducing the cells into the patient. This method can be particularly effective where the immune system or bone marrow cells must be depleted by radiation and/or chemotherapy for therapeutic purposes, such as in the case, for example, of patients diagnosed with multiple myeloma, non-Hodgkins lymphoma, autoimmune disease, or solid tumor cancers.

For the treatment of leukemias, autoimmune disease, or genetic diseases such as sickle cell anemia or thalassemia, re-population of the patient's blood or immune system cells with allogeneic cells of the present invention, or isolated by the method of the present invention, can be performed, particularly when the histocompatibility antigen has been altered in the manner described by Lawman, et al. (WO 98/42838).

For the purposes described herein, either autologous or allogeneic DPMSCs of the present invention can be administered to a patient, either in differentiated or undifferentiated form, genetically altered or unaltered, by direct injection to a tissue site, systemically, on or around the surface of an acceptable matrix, or in combination with a pharmaceutically acceptable carrier.

DPMSCs Provide a Model System for Studying Differentiation Pathways:

Yet another use of the population of DPMSCs of the invention is as a research tool. Cells of the present invention are useful for further research into developmental processes, as well. Ruley, et al. (WO 98/40468), for example, have described vectors and methods for inhibiting expression of specific genes, as well as obtaining the DNA sequences of those inhibited genes. Cells of the present invention can be treated with the vectors such as those described by Ruley, which inhibit the expression of genes that can be identified by DNA sequence analysis. The cells can then be induced to differentiate and the effects of the altered genotype/phenotype can be characterized.

Hahn, et al. (*Nature* (1999) 400: 464468) demonstrated, for example, that normal human epithelial fibroblast cells can be induced to undergo tumorigenic conversion when a combination of genes, previously correlated with cancer, were introduced into the cells.

Control of gene expression using vectors containing inducible expression elements provides a method for studying the effects of certain gene products upon cell differentiation. Inducible expression systems are known to those of skill in the art. One such system is the ecdysone-inducible system described by No, D., et al. *Proc. Natl. Acad. Sci. USA* (1996) 93: 3346-3351.

DPMSCs can be used to study the effects of specific genetic alterations, toxic substances, chemotherapeutic agents, or other agents on the developmental pathways. Tissue culture techniques known to those of skill in the art allow mass culture of hundreds of thousands of cell samples from different individuals, providing an opportunity to perform rapid screening of compounds suspected to be, for example, teratogenic or mutagenic.

For studying developmental pathways, DPMSCs can be treated with specific growth factors, cytokines, or other agents, including suspected teratogenic chemicals. DPMSCs can also be genetically modified using methods and vectors previously described. Furthermore, DPMSCs can be altered using antisense technology or treatment with proteins introduced into the cell to alter expression of native gene sequences. Signal peptide sequences, for example, can be used to introduce desired peptides or polypeptides into the cells. A particularly effective technique for introducing polypeptides and proteins into the cell has been described by Rojas, et al., in *Nature Biotechnology* (1998) 16: 370-375. This method produces a polypeptide or protein product that can be introduced into the culture media and translocated across the cell membrane to the interior of the cell. Any number of proteins can be used in this manner to determine the effect of the target protein upon the differentiation of the cell. Alternately, the technique described by Phelan et al. (*Nature Biotech*. (1998) 16: 440-443) can be used to link the herpes virus protein VP22 to a functional protein for import into the cell.

Cells of the present invention can also be genetically engineered, by the introduction of foreign DNA or by silencing or excising genomic DNA, to produce differentiated cells with a defective phenotype in order to test the effectiveness of potential chemotherapeutic agents or gene therapy vectors.

DPMSCs Provide a Variety of Differentiated and Undifferentiated Cultured Cell Types for High-Throughput Screening DPMSCs of the present invention can be cultured in, for example, 96-well or other multi-well culture plates to provide a system for high-throughput screening of, for example, target cytokines, chemokines, growth factors, or pharmaceutical compositions in pharmacogenomics or pharmacogenetics. The DPMSCs of the present invention provide a unique system in which cells can be differentiated to form specific cell lineages from the same individual. Unlike most primary cultures, these cells can be maintained in culture and can be studied over time. Multiple cultures of cells from the same individual and from different individuals can be treated with the factor of interest to determine whether differences exist in the effect of the cellular factor on certain types of differentiated cells with the same genetic makeup or on similar types of cells from genetically different individuals.

Cytokines, chemokines, pharmaceutical compositions and growth factors, for example, can therefore be screened in a timely and cost-effective manner to more clearly elucidate their effects. Cells isolated from a large population of individuals and characterized in terms of presence or absence of genetic polymorphisms, particularly single nucleotide polymorphisms, can be stored in cell culture banks for use in a variety of screening techniques. For example, dental pulp marrow similar cells from a statistically significant population of individuals, which can be determined according to methods known to those of skill in the art, provide an ideal system for high-throughput screening to identify polymorphisms associated with increased positive or negative response to a range of substances such as, for example, pharmaceutical compositions, vaccine preparations, cytotoxic chemicals, mutagens, cytokines, chemokines, growth factors, hormones, inhibitory compounds, chemotherapeutic agents, and a host of other compounds or factors. Information obtained from such studies has broad implication for the treatment of infectious disease, cancer, and a number of metabolic diseases.

In the method of using DPMSCs to characterize cellular responses to biologic or pharmacologic agents, or combinatorial libraries of such agents, DPMSCs are isolated from a statistically significant population of individuals, culture expanded, and contacted with one or more biologic or pharmacologic agents. DPMSCs can be induced to differentiate, where differentiated cells are the desired target for a certain biologic or pharmacologic agent, either prior to or after culture expansion. By comparing the one or more cellular responses of the DPMSC cultures from individuals in the statistically significant population, the effects of the biologic or pharmacologic agent can be determined. Alternately, genetically identical DPMSCs, or cells differentiated therefrom, can be used to screen separate compounds, such as compounds of a combinatorial library. Gene expression systems for use in combination with cell-based high-throughput screening have been described (see Jayawickreme, C. and Kost, T., *Curr. Opin. Biotechnol.* (1997) October 8, 5: 629-634). A high volume screening technique used to identify inhibitors of endothelial cell activation has been described by Rice, et al., which utilizes a cell culture system for primary human umbilical vein endothelial cells. (Rice, et al., *Anal. Biochem*. (1996) 241: 254-259.) The cells of the present invention provide a variety of cell types, both terminally differentiated and undifferentiated, for high-throughput screening techniques used to identify a multitude of target biologic or pharmacologic agents. Importantly, the cells of the present invention provide a source of cultured cells from a variety of genetically diverse individuals who may respond differently to biologic and pharmacologic agents.

DPMSCs and Genetic Profiling

Genetic variation can have indirect and direct effects on disease susceptibility. In a direct case, even a single nucleotide change, resulting in a single nucleotide polymorphism (SNP), can alter the amino acid sequence of a protein and directly contribute to disease or disease susceptibility. Functional alteration in the resulting protein can often be detected in vitro. For example, certain APO-lipoprotein E genotypes have been associated with onset and progression of Alzheimer's disease in some individuals.

DNA sequence anomalies can be detected by dynamic-allele specific hybridization, DNA chip technologies, and other techniques known to those of skill in the art. Protein coding regions have been estimated to represent only about 3% of the human genome, and it has been estimated that there are perhaps 200,000 to 400,000 common SNPs located in coding regions.

Previous investigational designs using SNP-associated genetic analysis have involved obtaining samples for genetic analysis from a large number of individuals for whom phenotypic characterization can be performed. Unfortunately, genetic correlations obtained in this manner are limited to identification of specific polymorphisms associated with readily identifiable phenotypes, and do not provide further information into the underlying cause of the disease.

DPMSCs of the present invention can provide the necessary element to bridge the gap between identification of a genetic element associated with a disease and the ultimate phenotypic expression noted in a person suffering from the disease. Briefly, DPMSCs are isolated from a statistically significant population of individuals from whom phenotypic data can be obtained (see Collins, et al., *Genome Research* (1998) December, 8(12):1229-1231). These DPMSC samples are then cultured expanded and subcultures of the cells are stored as frozen stocks, which can be used to provide cultures for subsequent developmental studies.

From the expanded population of cells, multiple genetic analyses can be performed to identify genetic polymorphisms. For example, single nucleotide polymorphisms can be identified in a large sample population in a relatively short period of time using current techniques, such as DNA chip technology, known to those of skill in the art (Wang, D., et al., *Science* (1998) 280: 1077-1082; Chee, M., et al., *Science* (1996) 274: 610-614; Cargill, M., et al., *Nature Genetics* (1999) 22: 231-238; Gilles, P., et al., *Nature Biotechnology* (1999) 17: 365-370; Zhao, L. P., et al., *Am. J. Human Genet.* (1998) 63: 225-240). Techniques for SNP analysis have also been described by Syvanen (Syvanen, A., Hum. Mut. (1999) 13: 1-10), Xiong (Xiong, M. and L. Jin, *Am. J. Hum. Genet.* (1999) 64: 629-640), Gu (Gu, Z., et al., *Human Mutation* (1998) 12: 221-225), Collins (Collins, F., et al., *Science* (1997) 278: 1580-1581), Howell (Howell, W., et al., *Nature Biotechnology* (1999) 17: 87-88), Buetow (Buetow, K., et al., *Nature Genetics* (1999) 21: 323-325), and Hoogendoom (Hoogendoom, B., et al., *Hum. Genet.* (1999) 104: 89-93).

When certain polymorphisms are associated with a particular disease phenotype, cells from individuals identified as carriers of the polymorphism can be studied for developmental anomalies, using cells from non-carriers as a control. DPMSCs of the present invention provide an experimental system for studying developmental anomalies associated with particular genetic disease presentations, particularly, since they can be induced to differentiate, using certain methods described herein and certain other methods known to those of skill in the art, to form particular cell types. For example, where a specific SNP is associated with a neurodegenerative disorder, both undifferentiated DPMSCs and DPMSCs differentiated to form neuronal precursors, glial cells, or other cells of neural origin, can be used to characterize the cellular effects of the polymorphism. Cells exhibiting certain polymorphisms can be followed during the differentiation process to identify genetic elements which affect drug sensitivity, chemokine and cytokine response, response to growth factors, hormones, and inhibitors, as well as responses to changes in receptor expression and/or function. This information can be invaluable in designing treatment methodologies for diseases of genetic origin or for which there is a genetic predisposition.

In the present method of using DPMSCs to identify genetic polymorphisms associated with physiologic abnormalities, DPMSCs are isolated from a statistically significant population of individuals from whom phenotypic data can be obtained (a statistically significant population being defined by those of skill in the art as a population size sufficient to include members with at least one genetic polymorphism) and culture expanded to establish DPMSC cultures. DNA from the cultured cells is then used to identify genetic polymorphisms in the cultured DPMSCs from the population, and the cells are induced to differentiate. Aberrant metabolic processes associated with particular genetic polymorphisms are identified and characterized by comparing the differentiation patterns exhibited by DPMSCs having a normal genotype with differentiation patterns exhibited by DPMSCs having an identified genetic polymorphism or response to putative drugs.

DPMSCs Provide Safer Vaccine Delivery

DPMSCs cells of the present invention can also be used as antigen-presenting cells when genetically altered to produce an antigenic protein. Using multiple altered autologous or allogeneic progenitor cells, for example, and providing the progenitor cells of the present invention in combination with plasmids embedded in a biodegradable matrix for extended release to transfect the accompanying cells, an immune response can be elicited to one or multiple antigens, potentially improving the ultimate effect of the immune response by sequential release of antigen-presenting cells. It is known in the art that multiple administrations of some antigens over an extended period of time produce a heightened immune response upon ultimate antigenic challenge. Alternately, DPMSCs can be used as antigen-presenting cells, in the method of Zhang, et al. (*Nature Biotechnology* (1998) 1: 1045-1049), to induce T-cell tolerance to specific antigen.

Many current vaccine preparations incorporate added chemicals and other substances, such as antibiotics (to prevent the growth of bacteria in vaccine cultures), aluminum (adjuvant), formaldehyde (to inactivate bacterial products for toxoid vaccines), monosodium glutamate (stabilizer), egg protein (component of vaccines prepared using embryonated chicken eggs), sulfites (stabilizer), and thimerosol (a preservative). Partly due to these added components, there is currently a broad-based public concern over the safety of vaccine preparations. Thimerosol, for example, contains mercury and is made from a combination of ethyl mercuric chloride, thiosalicylic acid, sodium hydroxide and ethanol. Furthermore, some studies, although inconclusive, have suggested a possible link between some vaccine components and potential complications such as those diseases commonly associated with autoimmunity. Thus, more effective vaccine therapies are needed and public cooperation with vaccine initiatives will be easier to promote if there is a greater degree of comfort with the method of vaccination.

DPMSCs of the present invention can be differentiated to form dendritic cells, which present antigen to T cells and thereby activate them to respond against foreign organisms. These dendritic cells can be genetically altered to express foreign antigens, using techniques previously described. A particular advantage of this method of vaccine delivery lies in the fact that more than one antigen can be presented by a single genetically altered cell.

Differentiated or undifferentiated DPMSC vaccine vectors of heterologous origin provide the added advantage of stimulating the immune system through foreign cell-surface markers. Vaccine design experiments have shown that stimulation of the immune response using multiple antigens can elicit a heightened immune response to certain individual antigens within the vaccine preparation.

Immunologically effective antigens have been identified for hepatitis A, hepatitis B, varicella (chickenpox), polio, diphtheria, pertussis, tetanus, Lyme disease, measles, mumps, rubella, Haemophilus influenzae type B (Hib), BCG, Japanese encephalitis, yellow fever, and rotavirus, for example.

The method for inducing an immune response to an infectious agent in a human individual using DPMSCs of the present invention can be performed by expanding a clonal population of dental pulp marrow similar cells in culture, genetically altering the expanded cells to express one or more pre-selected antigenic molecules to elicit a protective immune response against an infectious agent, and introducing into the individual an amount of genetically altered cells effective to induce the immune response. Methods for administering genetically altered cells are known to those of skill in the art. An amount of genetically altered cells effective to induce an immune response is an amount of cells which produces sufficient expression of the desired antigen to produce a measurable antibody response, as determined by methods known to those of skill in the art. Preferably, the antibody response is a protective antibody response that can be detected by resistance to disease upon challenge with the appropriate infectious agent.

DPMSCs and Cancer Therapy

DPMSCs of the present invention provide a novel vehicle for cancer therapies. For example, DPMSCs can be induced to differentiate to form endothelial cells or precursors which will home to endothelial tissues when delivered either locally or systemically. The cells participate in formation of blood vessels to supply newly-formed tumors (angiogenesis), and divide and proliferate in the endothelial tissue accordingly. By genetically engineering these cells to undergo apoptosis upon stimulation with an externally-delivered element, the newly-formed blood vessels can be disrupted and blood flow to the tumor can be eliminated. An example of an externally-delivered element would be the antibiotic tetracycline, where the cells have been transfected or transduced with a gene which promotes apoptosis, such as Caspase or BAD, under the control of a tetracycline response element. Tetracycline responsive elements have been described in the literature (Gossen, M. & Bujard, H., Proc. Natl. Acad. Sci. USA (1992) 89: 5547 5551), provide in vivo transgene expression control in endothelial cells (Sarao, R. & Dumont, D., Transgenic Res. (1998) 7: 421 427), and are commercially available (CLONETECH Laboratories, Palo Alto, Calif.).

Alternately, undifferentiated DPMSCs or DPMSCs differentiated to form tissue-specific cell lineages can be genetically altered to produce a product, for export into the extracellular environment, which is toxic to tumor cells or which disrupts angiogenesis (such as pigment epithelium-derived factor (PEDF), described by Dawson, et al., Science (1999) 285: 245-248). For example, Koivunen, et al., describe cyclic peptides containing an amino acid sequence which selectively inhibits MMP-2 and MMP-9 (matrix metalloproteinases associated with tumorigenesis), preventing tumor growth and invasion in animal models and specifically targeting angiogenic blood vessels in vivo (Koivunen, E., Nat. Biotech. (1999) 17: 768 774). Where it is desired that cells be delivered to the tumor site, produce a tumor-inhibitory product, and then be destroyed, cells can be further genetically altered to incorporate an apoptosis-promoting protein under the control of an inducible promoter.

DPMSCs also provide a vector for delivery of cancer vaccines, since they can be isolated from the patient, cultured ex vivo, genetically altered ex vivo to express the appropriate antigens, particularly in combination with receptors associated with increased immune response to antigen, and reintroduced into the individual to invoke an immune response to the protein expressed on tumor cells.

EXAMPLES

The examples, which are intended to be purely exemplary of the invention and should therefore not be considered to limit the invention in any way, also describe and detail aspects and aspects of the invention discussed above.

Abbreviations: BDNF=brain-derived neurotrophic factors, Beta2/NeuroD=neurogenic differentiation transcription factor (also, beta-cell E-box transactivator 2), bFGF=basic fibroblast growth factor, BHA=butylated hydroxyanisole, BMP-receptor=1B bone morphogenetic protein receptor, type IB, c-Met=HGF receptor, DMEM=Dulbecco's modified Eagle medium, ECM=extracellular matrix, EGF= epidermal growth factor, ES=embryonic stem cells, FACS= fluorescence-activated cell sorting, FBS=fetal bovine serum, FN=fibronectin, GFAP=glial fibrillary acidic protein, HGF= hepatocyte growth factor, MAPCs=multipotent adult progenitor cells, NF-M=neurofilament 160-kDa, NF-L=neurofilament 68 kDa, NF-H=200 kDa neurofilament 200 kDa, NGF=β-nerve growth factor, NT-3=neurotrophin-3, NTRK3=NT-3 receptor, Osc=osteocalcin, Osp=osteopontin, Runx2=runt-homology domain transcription factor, SSEA-4=stage-specific embryonic antigen 4, Trk-A=tyrosine kinase receptor A (also, NGF receptor), TuJ1=β-III-tubulin III.

Example 1A

Isolation of DPMSC

Cell Culture

Dental pulp was extracted from normal exfoliated human deciduous teeth of 5- to 7-year old children (10 patients) with informed consent of the donors. Dental pulp was extracted using needle and was transferred into 35-mm Petri dishes F12/Medium 199/CMRL 1066 supplemented with 1.25% Human serum and supplemented with 1-50 ng/ml (preferably about 5-15 ng/ml) platelet derived growth factor-BB (PDGF-BB), 1-50 ng/ml (preferably about 1-15 ng/ml) epidermal growth factor (EGF), 1-50 ng/ml (preferably about 1-15 ng/ml) insulin-like growth factor (IGF), 1-50 ng/ml (preferably about 1-15 ng/ml) fibroblast growth factor-b (FGF-b), $10^{-10}$ to $10^{-8}$ M dexamethasone or other appropriate steroid, 0-1 μg/mL linoleic acid, and 10-50 mg/L ascorbic acid. Tissue explant of dental pulp was used to isolate immature DPMSC. The growing culture of DPMSC was maintained under these conditions for 1 day and then the cells were placed, optionally dissociated, in a collagenase/trypsin/chicken serum (CTC) media, and seeded into 35-mm Petri dishes. The use of CTC media aids in the detachment of cells that have developed more cell-to-cell connection junctions (e.g., tight junctions and desmosomes) and is better at detaching cells with such junctions than trypsin alone.

The culture was maintained semi-confluent in order to prevent the differentiation of the cells, and the cells were passed every 3 days with the medium refreshed two times at week. After 7 days, small colonies of adherent cells developed. After 2 weeks, DPMSC cells were small highly proliferative cells exhibiting reduced cytoplasm. Growth curves confirmed that DPMSC proliferated both in mediums with 2.5-1.25-0.5% human serum (HS) but that in 0.5% HS, the medium needed replacing daily, or every two days. The doubling time was estimated in 28 hours in 1.25%-2.25% HS medium and 29-30 hours in 0.25%-0.5% HS medium. DPMSCs showed a normal karyotype.

TABLE 1

| Medium | Plating efficiency | Duplication Time | Days Before Starvation |
| --- | --- | --- | --- |
| 1-Mid 2.5% HS | 135% | 28 hours | 5 days |
| 2-Mid 1.25% HS | 101% | 28 hours | 4 days |
| 3-Mid 0.5% HS | 58% | 29 hours | 3 days |
| 4-Mid 0.25% HS | 48% | 30 hours | 2 days |

Table 1 shows the index for plating efficiency, duplication time and days required before medium starvation.

For freezing, the cells were resuspended in a medium containing F12/Medium 199/CMRL 1066 supplemented with 1.25% human serum, growth factors, and 10% dimethylsulfoxide (Sigma, St. Louis, Mo., USA) at $5 \times 10^5$ cells/ml, and the temperature was slowly and gradually decreased at a rate of 1° C. per minute until a final temperature of −70° C. was reached. Thereafter, cells were transferred to liquid nitrogen. For thawing cryo-vials with DPMSC, the vials were placed into a 37° C. water bath for 2 minutes and thereafter washed twice with F12/Medium 199/CMRL 1066 supplemented with 1.25% human serum, and placed into culture. All cultures were incubated at 37° C. in a 5% $CO_2$ and high humidity environment.

Despite the high density of the cells exiting the dental pulp, neither differentiation nor slowed proliferation was observed as could be expected for confluent cell cultures, particularly in the absence of specific growth factors. At the same time, both differentiation and slowed proliferation were noted during the subsequent confluent culture following trypsinization. Without being bound by theory, it is possible that explanting dental pulp as an outgrowth culture before the initial passage with trypsinization may prevent any stem cells from undergo premature differentiation.

Example 1B

Method of Isolating and/or Culturing DPMSC

Dental pulp was extracted from normal exfoliated human deciduous teeth of 5- to 7-year-old children (12 patients) with informed consent of the donors. Dental pulp was extracted using needle and was transferred into 35-mm Petri dishes (Falcon, BD-Biosciences, Italy) with a proliferation medium composed of F-12 Coon's modified/Ambesi's modified (Gibco)/Medium 199(Sigma Aldrich, Germany)/CMRL 1066 (Sigma Aldrich, Germany) supplemented with 1.25% of Human serum 1-50 ng/ml platelet-derived growth factor-BB (PDGF-BB, Immunotools, Germany), 1-50 ng/ml epidermal growth factor (EGF, Immunotools, Germany), 1-50 ng/ml insulin-like growth factor-1 (IGF-1, Immunotools, Germany), 1-50 ng/ml fibroblast growth factor-I (FGF-b, Immunotools, Germany), $10^{-10}$ to $10^{-8}$ M dexamethasone (MP), 20-100 µg/L linoleic acid (Sigma, Germany), 10-50 mg/L ascorbic acid (Sigma) and 0.5 ml/L gentamycin (Gibco). The growing culture of DPMSC was maintained under these conditions for 1 day and then the cells were placed, optionally dissociated, in a medium containing Collagenase II 1000 U/mL (Wortington, USA) plus a CTC solution (Trypsin 0.5%, Sigma) Collagenase II 22 U/mL (Wortington) and chicken serum 0.2% (Gibco). Cells were then seeded into 35-mm Petri dishes.

Dental pulp population of cells was not subjected to any type of depletion techniques (e.g., immunodepletion or physical or chemical depletion) and when colonies developed in primary culture reached confluence after 2-3 weeks, cells were detached by CTC and sub-cultured into 100 mm dishes in the proliferation medium. The culture was maintained semiconfluent in order to prevent the differentiation of the cells, and the cells were passed every 3 days at the density of $2.10^3$ cells/cm$^2$.

Example 2A

Methods of Phenotype Analysis of DPMSC Cell Population

Immunofluorescence, Flow-cytometry, FISH and Immunoblot

Immunofluorescence and FISH analyses were performed on 4% buffered paraformaldehyde or methanol/acetone fixed cells, while FACS analysis was performed on P3-P5 cells detached from the culture substrate through a short incubation in CTC. Staining was performed either using properly conjugated primary antibodies or with un-conjugated primary antibodies followed by an incubation with conjugated secondary antibodies. Intracellular staining was performed after a permeabilization step utilizing the Intrastain Fixation and Permeabilization kit (Dako, Danmark), following the manufacturer's instructions.

Image acquisition was carried out by a Confocal Laser Microscope (Leica TCS-SP2, Leica Microsystems, Italy), utilizing either a 63× oil immersion objective (numerical aperture: 1.40) or a 40× oil immersion objective (numerical aperture: 1.25). Epifluorescence and phase contrast images were obtained utilizing a live cell imaging dedicated system consisting of a Leica DMI 6000B microscope which is connected to a Leica DFC350FX camera (Leica Microsystems, Italy). A 10× objective (numerical aperture: 0.25) was employed for this purpose. Bright field images were captured utilizing an Olympus AX70 microscope connected to an Olympus DP50 camera (Olympus, Italy). A 10× objective (numerical aperture: 0.40) was employed for this purpose. Adobe Photoshop software was utilized to compose, overlay the images and to adjust contrast (Adobe, USA).

FISH (Fluorescence-in-situ-hybridization) was performed utilizing X- and Y-chromosome probes (Vysis), following the manufacturer's instructions. DNA content of ethanol-fixed and propidium iodide-stained cells was determined.

Lysates for immunoblot were collected using the TRIzol Reagent (Gibco, Italy) as recommended by the manufacturer, and then quantified by BCA Protein Assay Reagent Kit (Pierce) and program LABSYSTEMS GENESIS V2.16. Samples were electrophoresed on a SDS-PAGE gel and transferred to a polyvinylidene difluoride membrane or nitrocellulose transfer membrane (Protran nitrocellulose transfer membrane; Schleicher & Schuell). Membranes were blocked in Tris-buffered saline with 5% BSA and 0.5-1% Tween. Antibody/antigen complexes were detected using ECL reagent (Amersham Biosciences)

RT-PCR Analysis.

Total RNA was extracted from $2.5 \times 10^6$ DPMSC cells grown in expansion or differentiation media, using TRIzol Reagent (Gibco, Italy), as recommended by the manufacturer. After treatment with DNase I (Ambion, USA), first strand cDNA synthesis was performed with 2 µg total RNA using random hexanucleotides and M-MLV reverse transcriptase (Invitrogen). PCR amplification was carried out in a final volume of 50 µl, using an amount of cDNA ranging from 80 ng to 150 ng, 10 mM Tris-HCl pH 9.0, 1.5 mM $MgCl_2$, 0.2 mM dNTPs, 25 pmol of each primer and 2 U Taq I polymerase (Amersham, Italy). The PCR conditions are described in Table 2

The optimal conditions and the number of cycles were determined to allow amplification of samples within the linear phase of the PCR. The reaction products were analyzed on 1-2% agarose gels.

TRAP-assay.

The detection of telomerase activity was performed utilizing the TRAPeze kit (Chemicon International) following the manufacturer's instructions.

Karyotyping.

Metaphase spreads were prepared from single-cell derived clones, cultured in the proliferation medium for 72 hours. Chromosome analysis was performed according to the standard procedures using QFQ and RBA banding techniques at 400-650 band resolution, respectively.

Von Kossa Staining.

Cells, fixed in 4% paraformaldehyde for 20 minutes, were treated with 2% silver nitrate (Sigma) in a clear glass coplin jar placed directly in front of a 60-W lamp for 1 hour. Slides were rinsed in distilled water (dH$_2$O), fixed with 2.5% sodium thiosulphate (Sigma) for 5 minutes, and washed in dH$_2$O. Cells were counterstained with Nuclear Fast Red (Sigma) for 1 minute and rinsed in tap water.

Alkaline Phosphatase Staining.

Cells differentiated for 28 days in ostogenic medium were fixed at −20° C. in methanol for 2 minutes and washed in 100 mM Tris-HCl, pH 9.5, 100 mM NaCl, and 10 mM MgCl$_2$ buffer (Sigma) for 10 minutes. Slides were then stained with fast 5-bromo-4-chloro-3-indolyl phosphate and nitroblue tetrazolium alkaline phosphatase substrate (Sigma) for 5 to 10 minutes and rinsed in dH$_2$O.

Periodic Acid-Schiff Staining for Glycogen Detection.

Slides were oxidized in 1% periodic acid for 5 minutes and rinsed three times in dH2O. Slides were then treated with Schiff's reagent for 15 minutes, rinsed in dH2O for 5-10 minutes, stained with Mayer's hematoxylin for 1 minute, and rinsed in dH2O.

Albumin and Urea Production

After differentiation for 17 days, medium was removed. Before adding fresh medium, cells were washed with HBSS. After 4 days, supernatants were collected and immediately snap-frozen. Albumin concentrations were determined by ELISA assays (Human Albumin Elisa Quantitation Kit Bethyl—Montgomery, Tex.), following the manufacturer's instructions. Urea concentrations were determined by QuantiChrom™ Urea Assay Kit (BioAssay Systems Hayward) following the manufacturer's instructions.

Example 2B

Phenotype Analysis of DPMSC Cell Population

RT-PCR revealed expression of Oct-4 Isoforms A-B, Sox-2, Nanog, Klf-4, c-Myc and Rex-1. DPMSC expressed mRNA for Rex-1 (low), Klf-4, Oct-4 iso A-isoB, Sox-2, Nanog, and c-Myc. It should be noted that over-expression of Klf-4, Oct-4 iso A-isoB, Sox-2, and c-Myc in somatic cells can permit their return to an undifferentiated stem stage.

Expression mRNA of stemness transcription factors in DPMSC was compared with NTERA2 embryonic stem cell line. Staining with antibodies confirmed that about 99% of the cells were strongly positive for Oct-4, Sox-2 and Nanog. The uniformity of expression of Oct-4 and Nanog was further confirmed by flow cytometry, while as expected, human primary fibroblasts were negative for this marker.

99% of OCT-4 expression was observed for DPMSC cells in proliferation and the signal had both cytoplasmic and nuclear localization. Immunoblot showed the presence of two isoforms of Oct-4 with the same grade of expression of control+cells NTERA-2. Immunofluorescence analysis showed that about 96% of the DPMSC cell population expressed Oct-4. FACS analysis also showed that about 99% of the cell population expressed Sox-2 expression for DPMSC cells in proliferation and that the signal had both cytoplasmic and nuclear localization. About 99% of the DPMSC cells in proliferation expressed Nanog and the signal was exclusively nuclear localization.

It should be noted in this respect that only a small fraction of amniotic stem cells was shown to be positive for Oct-4, while the percentage of Oct-4-positive cells varied from <0.01 to 80%, depending on the O$_2$ concentration in m-MAPC (Jiang et al., 2002). The high percentage of positive cells for Oct-4, Sox-2, and Nanog indicated an extremely uniform population of stem cells. Consistent with this observation, as shown below, we noted uniform differentiation of the entire stem cell population toward the same tissue type. Other ES markers, SSEA-3, SSEA-4, and TRA-1-60, TRA-1-81 and ALP were less uniformly expressed in DPMSC cells, but not SSEA-1.

Experiments were conducted to determine that ALP mRNA expression in DPMSCs was comparable to NTERA2 cells. In an alkaline phosphatase assay and BICP/NBT substrate transformation, DPMSCs demonstrated a high enzymatic activity in proliferation phase. DPMSCs showed no detectable signal for SSEA-1 and a low but present signal for SSEA-3 in 99% of cells. DPMSCs were 92% positive in a FACS analysis for SSEA-4 and SSEA-4 antibody stains DPMSC as well. Immunofluorescence studies for TRA-1-60 resulted in a low but integral positive signal for DPMSCs. Immunofluorescence studies for TRA-1-81 resulted in a low but integral positive signal for DPMSCs.

Additionally, the outgrowth cells were uniformly positive for human mesenchymal stem cell-specific antigens by FACS and expressed high levels (>90-95%) of CD10, CD29, CD13, CD44, CD49a, CD49d, CD59, CD73, CDw90, CD105, and Oct-4.

The outgrowth cells expressed low levels of CD66e, KDR, CD133, VE-Cad, and CD117. The phenotype was more homogenous and the same results were obtained after thawing, but their protein level decreased in human DPMSC cultures beyond 40 cell doublings, which may have been due to a partial loss of undifferentiated phenotype. A very small percentage (e.g., <1%) of the DPMSCs did expressed CD34 and CD45. The expression level of the following markers in the DPMSC cell population was as follows:

| Marker | Percentage Expressed in DPMSC cell population |
|---|---|
| CD-10 | 92.58% |
| CD-13 | 100% |
| CD-29 | 100% |
| CD-44 | 99% |
| CD-49a | 99% |
| CD-49d | 100% |
| CD59 | 100% |
| CD-73 | 100% |
| CD-90 | 100% |
| CD-105 | 99% |
| CD-66e | 0.79% |
| KDR | 4.47% |
| CD-133 | 2.28% |
| VE-Cad | 1.61% |
| CD-117 | 17.52% |
| CD-34 | 0.2% |
| CD-45 | 0.44% |

RT-PCR analysis of mRNA expression of the stem cell marker hTERT in DPMSC cell isolates was also conducted and relative telomerase activity compared with NTERA2 and KitCtr+positive controls. The telomere length of DPMSC P2 and P5 from a donor, age 6, was determined using Flow Fish techniques. Telomere length was (18.4%) about 14.7 Kbp P2 and (17.16%) about 13.8 kbp P5, respectively, 1301 cells (long telomeres). We have proved telomerase mRNA presence by rt-PCR, and its enzymatic activity that was 15.8% with respect to NTERA2 cells.

The presence of Oct-4, Sox-2, and Nanog combined with SSEA-4, SSEA-3, TRA-1-60, TRA-1-81, ALP, TRT presence and activity and telomere length are markers that correlated with presence of the most primitive cells in DPMSC cultures, like the absence of SSEA-1. During the proliferation phase, immunofluorescence was conducted to determine protein expression of Collagen I, Fibroblast Growth Factor receptor-I (FGFr-I), Growth Factor receptor-ii (FGFr-II), cardiac Troponin T (c-TnT), Smooth Muscle Actin (SMA), Neurofilament light (NF-L), Glial Fibrillar acidic protein (G-Fap), Neural Specific Enolase (NSE), Core Binding Factor Type I and II (Cbfa-I Ty I, II), Muscle segmental Omeobox 2 (Msx-2), Neuro-D, Connexin-43, Abcg-2, Serca-2a, Nestin, Vimentin. Messenger expression during proliferation phase was determined by RT-PCR and showed the expression of MDR-I, Abcg-2, FGFr-I, FGFr-II, Msx-2, Dlx-5, PPAR-γ, c-Met, CK-19, Alkaline phosphatase, Osteocalcin, Osteonectin, BMP-2, BMP-4, BMP-7, BMPr-Ia, BMPr-Ib, Cbfa-I type I, Cbfa-I type II, Collagen Type I, Aggrecan, Dermo-I, Dental matrix protein, G-Fap, Glypican, 3'-Tubulin, Neurofilament light, medium and heavy, NSE, Musashi, Vimentin, Sarcomeric actin (ASA), SMA, Cardiac actin, Myocardin, ANP, Gata-4, Nkx-2.5, Myosin heavy chain. Immunoblot analysis showed the expression of ASA, Serca 2a, $\beta^3$-Tubulin, Msx-2, Connexin-43, Dlx-5, Neuro-D, Ca-Channel DHPR, Cbfa-I Ty I-II.

FGFr-II was expressed at low degree during proliferation and at times, absent. In proliferation phase, 99% expression of Connexin-43 was observed. Cx-43 expression was observed by immunoblot both in proliferation and myocyte differentiation. GATA-4 expression showed nuclear and cytoplasmic (perinuclear) staining. Abcg-2 mRNA was expressed at high levels both in proliferation and hepatic differentiation. MDR-I and Abcg-2 mRNAs were expressed both in proliferation and differentiation. Immunohistochemistry and fluorescence experiments for neuro D expression on DPMSC during proliferation phase showed nuclear localization. Immunoblot in proliferation and neuronal differentiation showed no expression only after complete differentiation. Smooth muscle actin, protein and mRNA were expressed during proliferation phase. Cardiac specific actin isoform showed low expression, protein and mRNA presence in proliferation. Nestin, a neural stem cell marker, protein was expressed in DPMSC. Vimentin, another neural stem cell marker, protein and mRNA were expressed in DPMSC during proliferation phase.

A population of identical cells from non-deciduous, permanent adult teeth were obtained and analyzed for immunophenotype as shown:

| Surface Antigens | Commercial Medium | Mid 1.25% HS |
|---|---|---|
| CD-13 | 45.58% | 99.99% |
| CD-29 | 87.50% | 99.18% |
| CD-34 | 0.07% | 0.04% |
| CD-45 | 0.27% | 0.08% |
| CD-49a | 87.47% | 95.73% |
| CD-73 | 99.87% | 100% |
| CD-90 | 97.51% | 99.9% |
| CD-105 | 55% | 96.89% |
| CD-117 | 0.70% | 2.01% |
| CD-133 | 0.50% | 0.64% |
| KDR | 0.51% | 1.47% |
| VE-Cad | 0.03% | 1.61% |
| CD-59 | 99.90% | 99.99% |
| CD-49d | 63.44% | 99.84% |
| CD-44 | 76.84% | 99.67% |
| CD-10 | 15.55% | 94.00% |
| CD-66e | 0.37% | 0.88% |

Immunophenotypic analysis by FACS of human adult third molar DPMSC 3° obtained after 14-20 cell doublings showed that a low percentage (e.g., <1%) of the cells did not express CD34, CD45; and that a high percentage (e.g., >90%) of the cells in the population expressed CD10, CD29, CD13, CD44, CD49a, CD49d, CD59, CD73, CDw90, and CD105. The population of cells expressed low levels of CD66e, KDR, CD133, VE-Cad, and CD117. The phenotype of the population of cells obtained using the protocols and medium described herein was highly homogenous as compared to the phenotype which was obtained using a simple commercial medium.

Without being bound by theory, it is possible that DPMSC represent a subpopulation of Dental Pulp that under our experimental conditions were predominantly and selectively proliferating. The gradient between the piece of dental pulp and the culture medium may serve as a vector directing the cells toward what they perceive as a site of injury, which leads to their continued and selective migration in the Petri dish.

Growth curves confirmed that DPMSC proliferate at high rate in mediums with 1.25-2.5% and even with 0.25-0.5% Human serum (HS), but in the latter conditions they need daily, or every two days, medium replacing; doubling time was estimated in 28 hours in 1.25-2.5% HS medium and 29-30 hours in 0.25-0.5% HS medium. Such high proliferation grade, as compared to BMSC, agrees with results obtained from Ghronthos S. Et al 2000 and Pierdomenico L. et al 2005.

It should be noted in this respect that over-expression of Klf-4, Oct-4 iso A-isoB, Sox-2, c-Myc in somatic cells may permit their to return in indifferentiate stem stage (Wernig M. et al 2007, Meissner A. et al 2007).

DPMSC, like MIAMI cells, express a high number of different types of messenger RNA found during all three germ layers terminal tissue specific differentiation. The question of why such high degree of extranuclear signals for many nuclear factors, such as Sox-2, Gata-4, Cbfa-I, Neuro-D/Beta2, HNF-3β, HNF4α, Msx-2, Dlx-5 and others were present was investigated. Without being bound by theory, it is possible that this atypical pattern of expression is the result of an accumulation of inactivated nuclear factors that permits to the cells a rapid response to a differentiation stimulus. This hypothesis could explain the expression of the numerous m-RNA species, normally associated to differentiation, in undifferentiated cells, suggesting that they could be molecularly equipped to remain pluripotent or to progress to diverse lineages. The likeness in population purity between IDPSC (Kerkis et al 2006) and the population of cells described in the present study leads us to believe that they are similar. The difference consists in the use of a medium with very low human serum which makes our cells more suited for human clinical applications.

DPMSC cells, and the medium used for their selection, hold strong promise in clinical reparative medicine for the treatment of degenerative or inherited diseases and are free of the ethical concerns raised by the use of ES cells. Autologous ex vivo expanded DPMSC cells could be used for autologous implantation aimed to repair damaged, aged or diseased tissues and organs. The ability to stably transduce DPMSC cells with specific genes, would also enable the genetic manipulation of autologous cells for the treatment of degenerative and congenital disorders.

Example 3A

Inducing DPMSCs to Differentiate to Form Committed Progenitors and Tissue-Specific Cell Types Using appropriate growth factors, chemokines, and cytokines, DPMSC of the present invention were induced to differentiate to form a number of cell lineages, including a variety of cells of mesodermal origin as well as cell from neuroectodermal origin and endodermal origin.

Osteoblastic Differentiation

About 20,000 DPMSCs/cm² were cultured in F-12 medium with about Dexamethasone (from about 10 nM to about 500 nM), β-glycerophosphate (from about 1 mM to about 5 mM), ascorbic acid (from about 10 mg/ml to about 100 mg/ml), $Ca^{2+}$ (from about 1 mM to about 2 mM), $Mg^{2+}$ (from about 0.1 mM to about 1 mM), glucose (from about 1 g/ml to about 5 g/ml), human serum (from about 0.5% to about 2%), retinoic acid (from about 100 nM to about 500 mM), 17-β-Estrogen (from about 0.1 M to about 10 μM), Vitamin K2 (from about 0.1 μM to about 10 μM), Vitamin D3 (from about 0.1 nM to about 10 nM) and Calcitonin (from about 0.1 nM to about 10 nM). To demonstrate presence of osteoblasts, we used Von Kossa staining assay (silver reduction of CaPo4) for mineral deposition and antibodies and primers for detecting osteonectin, connexin-43, osteopontin (early osteoblastic marker) and osteocalcin (late osteoblastic marker) after about 3 months of culture. At the same time, we had analyzed the presence, by rt-PCR, for BMPr-Ia, Ib, BMP-2, and BMP-4. We also used x-Ray diffraction patterns to evaluate the presence of hydroxyappatite formation.

In one method, DPMSC cells were suspended in an osteoblastic medium and placed in a Petri dish, such as a culture dish. DPMSC cells were allowed to settle to the bottom of the culture dish. Osteoblastic differentiation may be expected to occur, for example, in a 100% humidified atmosphere of 95% air, 5% $CO^2$ at 37° C. Osteoblastic differentiation was detected after about 2 weeks to about 8 weeks and ranged from about 3 weeks to about 4 months.

Changes in morphology were observed after 3 months of osteoblastic induction. Core binding factor Type I and II were detected by rt-PCR in DPMSC cells in proliferation and osteoblastic differentiation. Immunoblot showed Cbfa-I, osteoblastic master gene, isoforms expression in DPMSC cells. Cbfa-I was expressed in proliferation and after 3 months, osteoblastic differentiation. Msx-2 was constitutively expressed both in proliferation and differentiation population. Dlx-5 was down-regulated in differentiation as shown both by rt-PCR and immunoblot. mRNA expression of extracellular matrix proteins: collagen I, alkaline phosphatase, osteocalcin, and osteonectin in the proliferation and differentiation population.

rt-PCR analysis was conducted for detection of early osteoblastic marker osteopontin in proliferation and after 14 days and 3 months of osteoblastic induction. Very little to no osteopontin expression was observed during proliferation while an increased expression was observed at 14 days and a decreased expression was observed after 3 months of differentiation. In the differentiation stage, connexin-43 and osteopontin were co-expressed. Immunofluorescence showed the absence of osteocalcin during proliferation whereas osteocalcin was expressed after osteoblastic differentiation.

Example 3B

Osteoblastic Differentiation

About 40,000 DPMSC cells/cm² were cultured in F-12 Coon's modified/Ambesi's modified medium with Dexamethasone (from about 100 nM to about 25 nM, MP, Biomedicals), β-glycerophosphate 1.5 mM (Sigma), ascorbic acid-3P 13.5 μM (Fluka), $Ca^{2+}$ 1.2 mM (Sigma), $Mg^{2+}$ 0.6 mM (Sigma), Glucose 2 g/L (Sigma), human serum from 0.5% to 1%, Retinoic Ac. 250 nM (MP), 17-β-Estrogen 1 μM (MP, Biomedicals), Vitamin K2 10 μM (Sigma), Vit. D3 (from about 5 nM to about 10 nM, Sigma) and Calcitonin (from about 1 nM to about 2 nM, MP, Biomedicals).

In one aspect of the invention, DPMSC cells were suspended in an osteoblastic medium and placed in a culture dish. In this example, DPMSC cells were allowed to settle to the bottom of the culture dish to form a 3D structure. Osteoblastic differentiation may be expected to occur, for example, in a 100% humidified atmosphere of 95% air, 5% $CO_2$ at 37° C. Osteoblastic differentiation may be detected between 2 weeks to 8 weeks.

To confirm osteogenesis, cells were examined by RT-PCR for the expression of several genes, including osteocalcin (OSC), Collagen I, CBFA-I, ALP, osteonectin (OSN), osteopontin (OP), bone morphogenic protein-2, 4, 7 (BMP-2, -4, -7), in addition to receptors involved in osteogenesis bone morphogenic protein receptor-Ia, Ib-II (BMPr-Ia,-Ib, II) and the homeodomain proteins muscle segmental omeobox-2 (Msx2) and distal-less 5 (Dlx5).

Expression of CBFA-1 type I and II, a transcription factor that binds to the promoters of several osteogenic genes (Ducy et al., 1997), was observed at all time points in osteo-induced DPMSC cells. CBFA-1 type I expression was not specific to osteo-induced cells as a basal expression was observed in non-induced DPMSC cells. Quantification of CBFA-1 type I and II expression by semiquantitative PCR, confirmed a time-dependent increase in gene expression compared with non-induced DPMSC for type II and a decreased time-dependent expression compared with non-induced DPMSC for type I. These data were supported by western blot that also evidenced CBFA-1 proteins expression.

ALP and Collagen I expression were observed at all time points in differentiated and control DPMSC cells, however, continued treatment for 90 days resulted in an increase in ALP and Collagen I expression levels. In addition to CBFA-1, Collagen I and ALP, OSN expression was also observed in differentiated and control DPMSC cells. Although the expression of these genes is indicative of osteogenesis, they are not specific markers. However, expression of the late differentiation bone-specific gene OSC was observed in both induced and non-induced DPMSC cells. OSC protein was only expressed after 3 months of induction, as determined by immunofluorescence and immunoblot. It has also been demonstrated in the literature (Nefussi J. R. et al 1997).

The early osteoblastic differentiation marker (Yamamoto N. et al 2002) OSP expression in osteo-induced DPMSC cells seemed to be triphasic: not expressed during proliferation, highly expressed at 14 days and decreased expression after 3 months of induction. These data were confirmed by immunofluorescence. Both osteo- and non-induced DPMSC cells expressed homeodomain protein msx-2, a gene involved in osteoblast differentiation (Benson et al., 2000). Dlx5 was detected in non-induced DPMSC cells and its expression decreased in induced DPMSC cells. Data were confirmed by Western Blot.

BMP-2 and 4 expression was observed at all time points in differentiated and control DPMSC cells. At the same time, the expression of BMPr-Ia and Ib was observed at all time points, but with an increased expression level in the differentiated cells. On the other hand, the expression of BMP-7 messenger was present only during proliferation and BMPr-II expression was always absent on DPMSC cells.

During differentiation, some mineral nodules appeared and Von Kossa staining assay (silver reduction of CaPo4)

was used for revealing mineral deposition. X-Ray diffraction patterns were also used to evaluate the presence of Hydroxyapatite formation. 3D-Aggregate experiments showed the same results. Immunostaining was demonstrated to be specific in experiments where no staining was detected when primary antibodies were used as a negative control and Hobit cell line (Keeting P. E. et al 1992) was used as a positive control.

Example 4A

Generation of Neural Cells from Adult Dental Pulp Stem Cells

Differentiated neurons are post-mitotic, thus, little or no neuronal regeneration is usually observed in vivo. Therapies for neurodegenerative and traumatic disorders of the brain may be significantly furthered if new, proliferating neural stem cells (NSC) could be introduced in the defective areas of the brain which would resume the function of the defective tissue. DPMSCs selected from post-natal bone marrow that differentiate to all mesodermal cell types can also differentiate to neurons, oligodendrocytes, and astrocytes.

DPMSC cultures were established as described above. Neural development was induced as follows: Generations of neurons, astrocytes and oligodendrocytes were grown in medium consisting of neural differentiation medium. This medium comprised the following: DMEM-HG, 1×ITS, and 0.5-100 ng/mL FGF (preferably about 10 ng/mL). The medium also contained one or more of the following cytokines in order to induce differentiation into certain cell types: 5-50 ng/mL BDNF (preferably about 16 ng/mL) for dopaminergic neurons. The choice of growth factors to induce differentiation of DPMSCs into neural cells was based on what was known in embryonic development of the nervous system or from studies that evaluated in vitro NSC differentiation. Astrocytes were identified as glial-fibrilar-acidic-protein (GFAP) positive cells, oligodendrocytes were identified as glucocerebroside positive (GalC) and neurons were identified as cells that express in a sequential fashion NeuroD, Tubulin-IIIB (Tuji), synaptophysin and neurofilament-68, 160-200 kDa.

Other growth factors that are specifically expressed in the brain and that affect neural development in vivo and in vitro include brain derived neurotrophic factor (BDNF), glial derived neurotrophic factor (GDNF) and ciliary neurotrophic factor (CNTF). BDNF is a member of the nerve growth factor family that promotes in vitro differentiation of NSC, human subependymal cells, and neuronal precursors to neurons and promotes neurite outgrowth of hippocamal stem cells in vivo. Consistent with the known function of BDNF to support survival of dopaminergic neurons of the substantia nigra, when DPMSCs were treated with 16 ng/mL BDNF and 10 ng/ml EGFR, exclusive differentiation into tyrosine hydroxylase positive neurons was observed.

The ease with which DPMSCs was isolated from post-dental pulp, ex vivo expanded and induced to differentiate in vitro to glial cells or specific neuronal cell types circumvented one of the key problems in NSC transplantation, namely the availability of suitable donor tissue.

Generally, neural differentiation proceeds in at least three sequential steps: neural specification, neural commitment, and neural differentiation. Neural specification was induced by contacting 3000 DPMSC/cm² cells with a neural specification medium. A neural specification medium included a minimum essential medium, such as DMEM-HG. A neural specification medium typically contained one or more additional additives, such as serum, antibiotics, growth factors, nutrients, or combinations thereof. Specific non-limiting examples of such additives include serum (from about 5% to about 25% by volume).

DPMSC cells were incubated in a neural specification medium for sufficient time to induce neural specification. Such incubation time was between about 12 hours to about 36 hours, such as about 24 hours or 1-2 days. Neural commitment was induced by contacting neurally specified DPMSCs with a neural commitment medium. A neural commitment medium included a minimum essential medium, such as DMEM-HG. A neural commitment medium typically contained one or more additional additives, such as antibiotics, growth factors, nutrients, or combinations thereof. Examples of such additives included: EGF (from about 1 ng/ml to about 100 ng/ml) NT-3 (from about 1 ng/ml to about 100 ng/ml), NGF (from about 1 ng/ml to about 100 ng/ml), and BDNF (from about 5 ng/ml to about 500 ng/ml). BHA (from about 0.1 µM to about 100 µM) IBMX (from about 0.1 µM to about 100 µM) ATRA (from about 0.1 µM to about 10 µM) Progesteron (from about 0.1 nM to about 100 nM) 20 nM. Neurally specified DPMSCs were incubated in a neural commitment medium for sufficient time to induce neural commitment. Such incubation time was between about 10 days to about 20 days, such as about 15 days.

The number of neurites per neuron increased from 3 to 4 weeks after differentiation. Differentiation to cells with characteristics of neurons was confirmed by demonstrating presence of GFAP, neurofilament-160, synaptophysin, $\beta^3$-Tubulin by Western blot. The presence of synaptophysin, Synapsyn 1, Neurofilament 160, $\beta^3$-Tubulin, N-caderin, Tyrosine hydroxylase, Neuro-D, N-Cadherin, Neurofilament-68, NSE, Nestin, p75-NGFr and Vimentin was detected by immunofluorescence. Expression of $\beta^3$-Tubulin, Neurofilament-68, -160, -200, vimentin, NSE, $\beta^3$-Tubulin, G-Fap, Glypican, Musashi, and nestin was detected by rt-PCR.

Example 4B

Neurogenic Differentiation

Neural specification is induced by incubating DPMSC cells (3,000 cells/cm²) in DMEM-high glucose (Invitrogen) with 10% FBS. After 24 hours, medium was replaced with neural commitment medium with DMEM-high glucose, 10% FBS containing B27 (Invitrogen), 10 ng/ml EGF (Peprotech EC) and 20 ng/ml bFGF (Peprotech EC) for 15 days. Cells were then passed 1:3 and placed in neural commitment medium with NT-3 20 ng/ml (Immunotools), NGF 20 ng/ml (Immunotools), BDNF 50 ng/ml (Immunotools), BHA 20 µM (Sigma), IBMX 50 µM (Sigma), ATRA 1 µM (Sigma), and Progesteron 20 nM (Sigma).

Neural differentiation is induced by contacting neurally committed cells with a neural differentiation medium, that consists of DMEM. NT-3 20 ng/ml (Immunotools), NGF 20 ng/ml (Immunotools), BDNF 50 ng/ml (Immunotools), 5 µg/ml insulin (Sigma), 200 µM and indomethacin (Sigma) and 0.5 mM IBMX (Sigma). Neurally committed DPMSC cells were incubated in a neural differentiation medium for 1 day.

In one aspect of the invention, DPMSC cell pellets were suspended in three sequential mediums in a culture dish. In this example, DPMSC cells were allowed to settle to the bottom of the culture dish to form a 3-dimensional (3D) structure. Neural differentiation may be expected to occur, for example, in a 100% humidified atmosphere of 95% air, 5% $CO_2$ at 370. Neural differentiation may be detected in 4 weeks.

The morphology of the neural-induced DPMSC cells closely resembled that of mature neurons: they had a large number of neurites, increased from 3 to 4 weeks after differentiation, and with significant branching.

Semiquantitative rt-PCR showed that DPMSC cells expressed $\beta^3$-Tubulin, Neurofilament-68, -160, -200, vimentin, NSE, G-Fap, Musashi, both at low levels in proliferation and at high levels after induction. Neural stem precursor marker, Vimentin, was expressed both in proliferation and neural differentiation, but during the induction, it was less organized. Neuro-endocrine nuclear factor, Neuro-D/Beta-2, was expressed only during proliferation as demonstrated by both immunofluorescence and Western blot.

Expression of Nestin, another neurofilament neural stem marker, was decreased from the proliferation to induction stage. $\beta^3$-Tubulin was largely expressed in 99% of DPMSC cells after differentiation assayed by both immunofluorescence and Western blot. Structural neurofilaments NF-160 and NF-200 were expressed only during differentiation, the positivity was about 50% for the first and a lesser extent for the second, which is consistent with a mature neural phenotype (D'ippolito G. et al 2004). Data were also confirmed by immunoblot for NF-160. In contrast, NF-68 protein was always expressed during proliferation and after neural induction, as shown for NSE.

Synaptic vesicle trafficking markers Synapsyn-I and synaptophysin were expressed only after differentiation in all neural induced DPMSC cells, at the same time, Tyrosine hydroxylase, N-caderin, and p75-NGFr were detected using immunofluorescence only after induction.

The Oligodendrocyte marker-4 (O-4) was not expressed. G-Fap, astrocyte marker, was expressed during both proliferation and neural differentiation, but was less organized during the induction. GFAP and beta3-tubulin were co-expressed, consistent with recent findings (Soen Y. et al 2006). 3D-Aggregate experiments showed the same results. Specific immunostaining was demonstrated in experiments where no staining was detected when primary antibodies were used as negative controls and Bc2C glioblastoma cell line was used as positive control.

Example 5A

Cardiomyocyte Differentiation

Differentiation to any cardiomyocytes can be achieved by plating DPMSC at 10,000 cells/cm$^2$ prior to induction of differentiation. To induce cardiomyocyte cell differentiation, confluent DPMSC cells were treated with DMEM HG with FBS (from about 1% to about 10%), IBMX (from about 0.1 mM to about 10 mM), VEGF (from about 1 ng/ml to about 20 ng/ml). DPMSC cells were suspended in a cardiomyocyte medium and placed in a culture dish. DPMSC cells were allowed to settle to the bottom of the culture dish. Cardiomyocyte differentiation was expected to occur, for example, in a 100% humidified atmosphere of 95% air, 5% CO2 at 37°. Cardiomyocyte differentiation was detected between about 2 weeks to about 3 months. Muscle differentiation in vitro was demonstrated by detecting sequential activation of actinin, skeletal and cardiac actin and skeletal myosin, either by immunohistochemistry or Western blot and rt-PCR analysis using commercially available antibodies and specific primers. By immunohistochemistry, 90% of cells expressed mature muscle proteins after 14 days. Treatment with differentiation medium resulted in expression of ASA, Ca-channel DHPR, SMA, c-TnT, Connexin-43, Msx-2, Myosin heavy chain, Gata-4, Serca 2A during the 18 days of culture. In addition, cardiac heavy myosin were organized and co-expressed with ASA up to 30 days, like Actinin.

Example 5B

Cardiomyocyte Differentiation

Differentiation to any muscle phenotype required that DPMSC were plated at 11,000 cells/cm$^2$ prior to induction of differentiation. To induce cardiomyocyte cell differentiation, confluent DPMSC cells were treated with DMEM with 5% FCS (Sigma-Aldrich), 10 ng/mL bFGF, 10 ng/mL VEGF, and 10 ng/mL IGF-1 (all from Peprotech EC). Cells were allowed to become confluent and cultured for about 2 weeks to about 3 months with medium exchanges every 4 days.

In one aspect of the invention, DPMSC cells were suspended in a cardiomyocyte medium and placed in a culture dish. In this example, DPMSC pellet cells were allowed to settle to the bottom of the culture dish to form a 3D structure. Cardiomyocyte differentiation may be expected to occur, for example, in a 100% humidified atmosphere of 95% air, 5% $CO_2$ at 37°. Cardiomyocyte differentiation may be detected between 2 weeks to 3 months. Cardiomyocyte differentiation may be detected between about 2 weeks to about 3 months. During this differentiation period, cells became long and irregular. Co-expression of Atrial natriuretic peptide (ANP), Smooth muscle actin (SMA), Skeletal muscle actin (SKMA), Cardiac actin (CA), cardiac-Troponin T (c-TNT), Miocyte cancer factor-2a (MEF-2a), and Myosin heavy chain (Mhc) was detected by semiquantitative rt-PCR during both proliferation and differentiation. The expression was increased in the last phase.

Messenger expression for Gata-4 and Nkx-2.5 was very low in both phases. Msx-2 m-RNA expression was very high in proliferation and differentiation. Expression of Myocardin was decreased after differentiation. It was shown that cells had organized filaments of α-actinin, α-sarcomeric actin and Myosin heavy chain. Data was confirmed by Western blot. α-sarcomeric actin and Myosin heavy chain were co-expressed and organized in a fraction of differentiating cells, consistent with the literature.

Gap-junctions were demonstrated by the presence of connexin-43 in proximity to cell to-cell contact sites. L-Type calcium channels, Serca-2 ATPase pump, c-TNT were also identified in differentiated cells. SMA was expressed at high degree during the proliferation stage and its expression was decreased after induction, without losing the filamentous structure as shown by immunofluorescence.

It has been reported that α-smooth muscle actin (SMA) is present in embryonic and fetal but not in adult cardiomyocytes, suggesting that these cardiomyocytes may represent an early stage of cardiomyocytes (Leor J. et al 1996, Etzion S. et al 2001). Expression of Msx-2 was decreased constantly from proliferation to differentiation stage, whereas GATA-4 expression was lost after cardiomyocyte induction. 3D-Aggregate experiments showed the same results. Specific immunostaining was demonstrated in experiments where no staining was detected when secondary antibodies were used as negative controls and explanted cultured pieces of heart were used as positive controls.

Example 6A

Hepatic Differentiation

To obtain hepatic cells, DPMSC were plated at 20,000 cells/cm$^2$ prior to induction of differentiation with DMEM low glucose 1-10% FCS, hepatocyte growth factor (HGF) (from about 1 ng/ml to about 100 ng/ml), oncostatin (OSM) (from about 1 ng/ml to about 100 ng/ml), nicotinamide (from about 1 mM to about 100 mM), LDL (from about 0.1 μg/ml to about 10 ng/ml), FGF-4 (from about 1 ng/ml to about 100 ng/ml), insulin (from about 1 μg/ml to about 10 μg/ml), linoleic acid (from about 180 μg/L to about 1 mg/L), and glucose (from about 1 g/L to about 10 g/L). After 14-37 days, small epitheloid cells were seen that expressed and secreted albumin. In addition, the cells expressed mRNA for HGF receptor, cytokeratin 19. Abcg-2, MDR-I, transferrin, somatostatin, erythropoietin, cytochrome P-450 subunit 2e1. The presence and secretion of albumin, urea, cytokeratin-8-18-19, HNF-3β and HNF-4α suggested possible differentiation to hepatic cells.

Example 6B

Hepatic Differentiation

Hepatocyte differentiation was induced in confluent DPMSC cells by incubating with DMEM low glucose 1% FCS, hepatocyte growth factor 20 ng/mL (HGF) (Immunotools), Oncostatin 10 ng/ml (OSM) (Sigma), Nicotinamide 10 mM (Sigma), LDL 1.25 μg/mL (Sigma), FGF-4 10 ng/mL (Sigma), Insulin (from 1 μg/ml to 10 μg/ml) (Sigma), Linoleic acid 0.00018 g/L (MP) and glucose 1.25 g/L (Sigma) for 14-37 days. Hepatic differentiation may be expected to occur, for example, in a 100% humidified atmosphere of 95% air, 5% $CO_2$ at 37°, hepatic differentiation may be detected after 5 weeks.

Differentiated cells, after 14-37 days, assumed a globular shape with an eccentric nucleus. From proliferation to differentiation, these cells had increased expression of Albumin, Transferrin, Somatostatin, Erytropoietin and Cytochrome P-450 subunit 2e1, similar expression for c-MET/HGF-r (Hepatocyte nuclear factor receptor), Abcg-2, MDR-I (Siddiqui M. M. et al 2004, De Coppi P. et al 2007), and decreased expression for cytokeratin-19 (Ck-19) as demonstrated by semiquantitative rt-PCR.

Cells stained positive for the hepatic epitelial specific cytokeratins 8, 18 and 19, in a greater percentage only after differentiation with a small filamentous organization as shown by immunofluorescence. Cells expressed both Hepatocyte nuclear factor 4α and 3β, after Hepatic induction as shown by immunoblotting. These are important nuclear factors for the final morphological and functional commitment into hepatic epithelium (Nagy P. et al 1994, Talens-Visconti R. et al 2006). Cells acquired several hepatocytic functions such as the ability to store glycogen as demonstrated by PAS staining, and to produce albumin and urea as examined by testing the concentration/dose of these factors in culture supernatants. Specific immunostaining was demonstrated in experiments where no staining was detected when secondary antibodies were used as negative controls and HepG2 cells were used as positive controls.

Example 7

DPMSC for Replacement Therapy and/or Gene Therapy

An effective amount of the DPMSCs of the present invention are used in cell replacement therapy and/or gene therapy to treat or alleviate symptoms of congenital neurodegenerative disorders or storage disorders such as, for instance, mucopolysaccharidosis, leukodystrophics (globoid-cell leukodystrophy, Canavan disease), fucosidosis, GM2 gangliosidosis, Nienamnn-Pick, Sanfilippo syndrome, Wolman disease, and Tay Sacks by administering an effective amount of DPMSCs to an individual in need thereof. They are used to treat or alleviate symptoms of acquired neurodegenerative disorders such as Huntingtons, Parkinsons, Multiple Sclerosis, and Alzheimers. They are also used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

An effective amount of DPMSCs of the present invention are used in cell replacement therapy and/or gene therapy to treat or alleviate symptoms of several organ diseases. The cells are used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders such as inborn errors of the urea-cycle, for instance Ornithine decarboxylase deficiency, citrullinemia, and argininosuccinic aciduria; inborn errors of amino acids and organic acids such as phenylketoinuria, hereditary tyrosinemia, and Alpha1-antitrypsin deficiency; and coagulation disorders such as factor VIII and IX deficiency. The cells are used to treat acquired liver disorders due to viral infections. The cells of the present invention are used in ex vivo applications such as to generate an artificial liver (akin to kidney dialysis), to produce coagulation factors and to produce proteins or enzymes generated by liver epithelium.

The cells of the present invention are used to in cell replacement therapy and/or gene therapy to treat or alleviate symptoms of biliary disorders such as biliary cirthosis and biliary atresia.

The cells of the present invention are used to in cell replacement therapy and/or gene therapy to treat or alleviate symptoms of pancreas disorders such as pancreatic atresia, pancreas inflammation, and Alpha1-antitrypsin deficiency. Further, as pancreas epithelium are made from the cells of the present invention, and as neural cells can be made, beta-cells can be generated. These cells are used for the therapy of diabetes (subcutaneous implantation or intrapancreas or intra-liver implantation.

Further, the cells of the present invention are used to in cell replacement therapy and/or gene therapy to treat or alleviate symptoms of gut epithelium disorders such as gut atresia, inflammatory bowel disorders, bowel infarcts, and bowel resection.

Moreover, the cells of the present invention are used to in cell replacement therapy and/or gene therapy to treat or alleviate symptoms of skin disorders such as alopecia, skin defects such as burn wounds, and albinism.

REFERENCES

1. Thomson J, Kalishman J, Golos T, Durning M, Harris C, Becker R, Hearn J: Isolation of a primate embryonic stem cell line. Proc Natl Acad Sci USA 92:7844 8, 1995
2. Thomson J A, Itskovitz-Eldor J, Shapiro S S, Waknitz M A, Swiergiel J J, Marshall V S, Jones J M: Embryonic stem cell lines derived from human blastocysts. Science 282:114 114, 1998

3. Shamblott M. Axelman J, Wang S, Bugg E, Littlefield J, Donovan P, Blumenthal P, Huggins G, Gearhart J: Derivation of pluripotent stem cells from cultured human primordial germ cells. Proc Natl Acad Sci USA 95:13726 31, 1998

4. Williams R L, Hilton D J, Pease S, Willson T A, Stewart C L, Gearing D P, Wagner E F, Metcalf D, Nicola N A, Gough N M: Myeloid leukaemia inhibitory factor maintains the developmental potential of embryonic stem cells. Nature 336:684 7, 1988

5. Orkin S: Embryonic stem cells and transgenic mice in the study of hematopoiesis. Int J Dev Biol 42:927 34, 1998

6. Weissman I L: Translating stem and progenitor cell biology to the clinic: barriers and opportunities. Science 287:1442 6, 2000

7. Gage F H: Mammalian Neural Stem Cells. Science 287:1433 1438, 2000

8. Svendsen C N, Caldwell M A, Ostenfeld T: Human neural stem cells: Isolation, expansion and transplantation. Brain Path 9:499 513, 1999

9. Okabe S, Forsberg-Nilsson K, Spiro A C, Segal M, McKay R D: Development of neuronal precursor cells and functional postmitotic neurons from embryonic stem cells in vitro. Mech Dev 59:89 102, 1996

10. Potten C: Stem cells in gastrointestinal epithelium: numbers, characteristics and death. Philos Trans R Soc Lond B Biol Sci 353:821 30, 1998

11. Watt F: Epidermal stem cells: markers patterning and the control of stem cell fate. Philos Trans R Soc Lond B Biol Sci 353:831, 1997

12. Alison M, Sarraf C: Hepatic stem cells. J Hepatol 29:678 83, 1998

13. Haynesworth S E, Barber M A, Caplan I A: Cell surface antigens on human marrow-derived mesenchymal cells are detected by monoclonal antibodies. Bone 13:69 80, 1992

14. Pittenger M F, Mackay A M, Beck S C, Jaiswal R K, Douglas R, Mosca J D, Moorman M A, Simonetti D W, Craig S, Marshak D R: Multilineage potential of adult human mesenchymal stem cells. Science 284:143 147, 1999

15. Gronthos S, Zannettino A C, Graves S, Ohta S, Hay S J, Simmon P J: Differential cell surface expression of the STRO-1 and alkaline phosphatase antigens on discrete developmental stages in primary cultures of human bone cells. J Bone Miner Res 14:47 56, 1999

16. Prockop D: Marrow stromal cells as stem cells for nonhematopoietic tissues. Science 276:71 4, 1997

17. Jackson K, Mi T, Goodell M A: Hematopoietic potential of stem cells isolated from murine skeletal muscle. Proc Natl Acad Sci USA 96:14482 6, 1999

18. Ferrari G, Cusella-De Angelis G, Coletta M, Paolucci E, Stornaiuolo A, Cossu G, Mavilio F: Muscle regeneration by bone marrow-derived myogenic progenitors. Science 279:528 30, 1998

19. Gussoni E, Soneoka Y, Strickland C, Buzney E, Khan M, Flint A, Kunkel L, Mulligan R: Dystrophin expression in the mdx mouse restored by stem cell transplantation. Nature 401:390 4, 1999

20. Asahara T, Masuda H, Takahashi T, Kalka C, Pastore C, Silver M, Kearne M, Magner M, Isner J M: Bone marrow origin of endothelial progenitor cells responsible for postnatal vasculogenesis in physiological and pathological neovascularization. Circ Res 85:221 8, 1999

21. Lin Y, Weisdorf D J, Solovey A, Hebbel R P: Origins of circulating endothelial cells and endothelial outgrowth from blood. J Clin Invest 105:71 7, 2000

22. Petersen B E, Bowen W C, Patrene K D, Mars W M, Sullivan A K, Murase N, Boggs S S, Greenberger J S, Goff J P: Bone marrow as a potential source of hepatic oval cells. Science 284:1168 1170, 1999

23. Theise N D, Badve S, Saxena R, Henegariu O, Sell S, Crawford J M, Krause D S: Derivation of hepatocytes from bone marrow cells in mice after radiation-induced myeloablation. Hepatology 31:235 40, 2000

24. Theise N D, Nimmakayalu M, Gardner R, Illei P B, Morgan G, Teperman L, Henegariu O, Krause D S: Liver from bone marrow in humans. Hepatology 32:11 6, 2000

25. Frankel M S: In Search of Stem Cell Policy. Science 298:1397, 2000

26. Greider C: Telomeres and senescence: the history, the experiment, the future. Curr Biol 8:178 81, 1998

27. Reubinoff B E, Pera M F, Fong C Y, Trounson A, Bongso A: Embryonic stem cell lines from human blastocysts: somatic differentiation in vitro. Nat Biotech 18:399 404, 2000

28. Nichols J. Zevnik B, Anastassiadis K, Niwa H, Klewe-Nebenius D, Chambers I, Scholer H, Smith A: Formation of pluripotent stem cells in the mammalian embryo depends on the POU transcription factor Oct4. Cell 95:379 91, 1998

29. Rosfjord E, Rizzino A: The octamer motif present in the Rex-1 promoter binds Oct-1 and Oct-3 expressed by EC cells and ES cells. Biochem Biophys Res Commun 203: 1795 802, 1997

30. Ben-Shushan E, Thompson J R, Gudas L J. Bergman Y: Rex-1, a gene encoding a transcription factor expressed in the early embryo, is regulated via Oct-3/4 and Oct-6 binding to an octamer site and a novel protein, Rox-1, binding to an adjacent site. Mol Cell Biol 18:1866 78, 1998

31. Uwanogho D, Rex M, Cartwright E J. Pearl G, Healy C, Scotting P J, Sharpe P T: Embryonic expression of the chicken Sox2, Sox3 and Sox11 genes suggests an interactive role in neuronal development. Mech Dev 49:23 36, 1995

32. Baum C, Weissman I, Tsukamoto A, Buckle A, Peault B: Isolation of a candidate human hematopoietic stem cell population. Proc Natl Acad Sci USA 89:2804, 1992

33. Jordan C, McKeam J, Lemischka I: Cellular and developmental properties of fetal hematopoietic stem cells. Cell 61:953 963, 1990

34. Bhatia M, Wang J, Knapp U, Bonnet D, Dick J: Purification of primitive human hematopoietic cells capable of repopulating immune-deficient mice. Proc Natl Acad Sci USA 94:5320, 1997

35. Goodell M, Rosenzweig M, Kim H, Marks D, DeMaria M, Paradis G, Grupp S, Sieff C, Mulligan R, Johnson R: Dye efflux studies suggest that hematopoietic stem cells expressing low or undetectable levels of 34 antigen exist in multiple species. Nature Medicine 3:1337 1345, 1997

36. Zijlmans J M, Visser J W, Kleiverda K, Kluin P M, Willemze R, Fibbe W E: Modification of rhodamine staining allows identification of hematopoietic stem cells with preferential short-term or long-term bone marrow-repopulating ability. Proc Natl Acad Sci USA 92:8901 8905, 1995

37. Phillips R L, Ernst R E, Brunk B, Ivanova N, Mahan M A, Deanehan J K, Moore K A, Overton G C. Lemischka I R: The genetic program of hematopoietic stem cells. Science 288:1635 40, 2000

38. Martin G R: Isolation of a pluripotent cell line from early mouse embryos cultured in medium conditioned by teratocarcinoma stem cells. Proc Natl Acad Sci USA 78:7634 8, 1981

39. Wobus A M, Holzhausen H, Jakel P, Schoneich J: Characterization of a pluripotent stem cell line derived from a mouse embryo. Exp Cell Res 52:212 9, 1984

40. Kannagi R, Cochran N A, Ishigami F, Hakomori S, Andrews P W, Knowles B B, Solter D: Stage-specific embryonic antigens (SSEA-3 and -4) are epitopes of a unique globo-series ganglioside isolated from human teratocarcinoma cells. EMBO J. 2:2355 61, 1983

41. Scholer H R, Hatzopoulos A K, Balling R, Suzuki N, Gruss P: A family of octamer-specific proteins present during mouse embryogenesis: evidence for germline-specific expression of an Oct factor. EMBO J. 8:2543 50, 1989

42. Yuan H, Corbi N, Basilico C, Dailey L: Developmental-specific activity of the FGF-4 enhancer requires the synergistic action of Sox2 and Oct-3. Genes Dev 9:263545, 1995

43. Rosner M H, Vigano M A, Ozato K, Timmons P M, Poirier F, Rigby P W, Staudt L M: A POU-domain transcription factor in early stem cells and germ cells of the mammalian embryo. Nature 345:686 92, 1990

44. Pikarsky E, Sharir H, Ben-Shushan E, Bergman Y: Retinoic acid represses Oct-3/4 gene expression through several retinoic acid-responsive elements located in the promoter-enhancer region. Mol Cell Biol 14:1026 38, 1994

45. Niwa H, Miyazaki J, Smith A G: Quantitative expression of Oct-3/4 defines differentiation, dedifferentiation or self-renewal of ES cells. Nat Genet 24:372 6, 2000

46. Cooke J E, Godin I, Ffrench-Constant C, Heasman J, Wylie C C: Culture and manipulation of primordial germ cells. Methods Enzymol 255:37 58, 1993

47. Hodes R J: Telomere length, aging, and somatic cell turnover. J Exper Med 190:153 156, 1999

48. Choi K, Kennedy M. Kazarov A. Papadimitriou J C, Keller G: A common precursor for hematopoietic and endothelial cells. Development 125:725 732, 1998

49. Medvinsky A, Dzierzak E: Definitive hematopoiesis is autonomously initiated by the AGM region. Cell 86:897, 1996

50. Yoder M, Hiatt K, Mukherjee P: In vivo repopulating bematopoietic stem cells are present in the murine yolk sac at day 9.0 postcoitus. Proc. Natl. Acad. Sci. USA 94:6776, 1997

51. Spangrude G, Heimfeld S, Weissman I: Purification and characterization of mouse hematopoietic stem cells. Science 241:58, 1988

52. Tricot G, Gazitt Y, Leemhuis T, Jagannath S, Desikan K R, Siegel D, Fassas A, Tindle S, Nelson J, Juttner C, Tsukamoto A, Hallagan J, Atkinson K, Reading C, Hoffman R, Barlogic B: Collection, tumor contamination, and engraftment kinetics of highly purified hematopoietic progenitor cells to support high dose therapy in multiple myeloma. Blood 91:4489 95, 1998

53. Gothot A, Pyatt R, McMahel J, Rice S, Srour E F: Functional heterogeneity of human CD34(+) cells isolated in subcompartments of the G0/G1 phase of the cell cycle. Blood 90:4384 4393, 1997

54. Goodell M, Brose K, Paradis G, Conner A, Mulligan R: Isolation and functional properties of murine hematopoietic stem cells that are replicating in vivo. J Exp Med 183:1797 1806, 1996

55. McCune J M, Namikawa R, Kaneshima H, Shultz L D, Lieberman M, Weissman I L: The SCID-hu mouse: murine model for the analysis of human hematolymphoid differentiation and function. Science 24:1632 1639, 1988

56. Moore K A, Hideo E, Lemischka I R: In vitro maintenance of highly purified transplantable hematopoietic stem cells. Blood 89:4337 437, 1997

57. Fraser C, Szilvassy S, Eaves C, Humphries R: Proliferation of totipotent hematopoietic stem cells culture at limiting dilution on supportive marrow stroma. Proc Natl Acad Sci USA 89:1968 1972, 1992

58. McKay R: Stem cells in the central nervous system. Science 276:66 71, 1997

59. Huard J M, Youngentob S L, Goldstein B J, Luskin M B, Schwob J E: Adult olfactory epithelium contains multipotent progenitors that give rise to neurons and non-neuronal cells. J Comp Neurol 400:469 486, 1998

60. Palmer T D, Takahashi J, Gage F H: The adult rat hippocampus contains primordial neural stem cells. Mol Cell Neurosci 8:389404, 1997

61. Lois C, Alvarez-Buylla A: Proliferating subventricular zone cells in the adult mammalian forebrain can differentiate into neurons and glia. Proc Natl Acad Sci USA 90:2074 7, 1993

62. Roy N S, Wang S, Jiang L, Kang J, Benraiss A, Harrison-Restelli C, Fraser R A, Couldwell W T, Kawaguchi A, Okano H, Nedergaard M, Goldman S A: In vitro neurogenesis by progenitor cells isolated from the adult human hippocampus. Nat Med 5:271 7, 2000

63. Johansson C B, Momma S, Clarke D L, Risling M, Lendahl U, Frisen J: Identification of a neural stem cell in the adult mammalian central nervous system. 1998 96:25 34, 1999

64. Fridenshtein A: Stromal bone marrow cells and the hematopoietic microenvironment. Arkh Patol 44:3 11, 1982

65. Wakitani S, Saito T, Caplan A: Myogenic cells derived from rat bone marrow mesenchymal stem cells exposed to 5-azacytidine. Muscle Nerve 1417 26:18, 1995

66. Gronthos S, Graves S, Ohta S, Simmons P: The STRO-1+fraction of adult human bone marrow contains the osteogenic precursors. Blood 84:4164 73, 1994

67. Colter D C, Class R, DiGirolamo C M, Prockop D J: Rapid expansion of recycling stem cells in cultures of plastic-adherent cells from human bone marrow. roc Natl Acad Sci USA 97:3213 8, 2000

68. Yui J, Chiu C, Lansdorp P: Telomerase activity in candidate stem cells from fetal liver and adult bone marrow. Blood 91:91 (9):3255 62, 1998

69. Bjornson C, Rietze R, Reynolds B, Magli M, Vescovi A: Turning brain into blood: a hematopoietic fate adopted by adult neural stem cells in vivo. science 283:354 7, 1999

70. Almeida Porada G, Crapnell H, Porada C, Benoit H, Quesenberry P, Zanjani E D: In vivo hematopoietic potential of human neuronal stem cells. Exp Hematol 28, Supplement 1:61 (abstract), 2000

71. Clarke D L, Johansson C B, Wilbertz J, Veress B, Nilsson E, Karlstrom H, Lendahl U, Frisen J: Generalized potential of adult neural stem cells. Science 288:1660 3, 2000

72. Rideout W M, 3rd, Wakayama T, Wutz A, Eggan K, Jackson-Grusby L, Dausman J, Yanagimachi R, Jaenisch R: Generation of mice from wild-type and targeted ES cells by nuclear cloning. Nat Genet 24:109 10, 2000

73. Wilmut I, Schnieke A E, McWhir J, Kind A J, Campbell K H: Viable offspring derived from fetal and adult mammalian cells. Nature 385:810 3, 1997

74. Tsonis P A: Regeneration in vertebrates. Dev Biol 221:273 84, 2000

75. Lemischka I: The power of stem cells reconsidered? Proc Natl Acad Sci USA 96:1493 5, 1999

76. Anderson R, Fassler R, Georges-Labou-sse E, Hynes R O, Bader B L, Kreidberg J A, Schaible K, Heasman J, Wylie C: Mouse primordial germ cells lacking beta1 integrins enter the germline but fail to migrate normally to the gonads. Development 126:1655 64, 1999

77. Keller G, Snodgrass H R: Human embryonic stem cells: the future is now. Nat Med 5:151 152, 1999

78. Lefebvre V, de Crombrugghe B: Toward understanding SOX9 function in chondrocyte differentiation. Matrix Biol 16:529 40, 1998

79. Yoshida K, Chambers I, Nichols J, Smith A, Saito M, Yasukawa K, Shoyab M, Taga T, Kishimoto T: Maintenance of the pluripotential phenotype of embryonic stem cells through direct activation of gp130 signalling pathways. Mech Dev 45:163 71, 1994

80. Ma Y G, Rosfjord E, Huebert C, Wilder P, Tiesman J. Kelly D, Rizzino A: Transcriptional regulation of the murine k-FGF gene in embryonic cell lines. Dev Biol 154:45 54, 1992

81. Anderson R, Copeland T K, Scholer H, Heasman J, Wylie C: The onset of germ cell migration in the mouse embryo. Mech Dev 91:61 8, 2000

82. Gerstenfeld L C, Shapiro F D: Expression of bone-specific genes by hypertrophic chondrocytes: implication of the complex functions of the hypertrophic chondrocyte during endochondral bone development. J Cell Biohem 62:1 9, 1996

83. Binette F, McQuaid D P, Haudenschild D R, Yaeger P C, McPherson J M, Tubo R: Expression of a stable articular cartilage phenotype without evidence of hypertrophy by adult human articular chondrocytes in vitro. J Orthop Res 16:207 16, 1998

84. Cai R L: Human CART1, a paired-class homeodomain protein, activates transcription through palindromic binding sites. Biochem Biophys Res Commun 250:305 11, 1998

85. Dietz U H, Sandell L J: Cloning of a retinoic acid-sensitive mRNA expressed in cartilage and during chondrogenesis. J Biol Chem 271:3311 6, 1996

86. Konieczny S F, Emerson C P Jr: Differentiation, not determination, regulates muscle gene activation: transfection of troponin I genes into multipotential and muscle lineages of IOT1/2 cells. Mol Cell Biol 5:2423 32, 1985

87. Dinsmore J, Ratliff J, Deacon T, Pakzaban P, Jacoby D, Galpem W, Isacson O: Embryonic stem cells differentiated in vitro as a novel source of cells for transplantation. Cell Transplant 5:131 143, 1996

88. Chen J. Goldhaner D: Transcriptional mechanisms regulating MyoD expression in the mouse. Cell Tissue Res 296:213 9, 1999

89. Wasserman S: FH proteins as cytoskeletal organizers. Cell Biology 8:111 115, 1998

90. Mesnard L. Samson F, Espinasse I, Durand J, Neveux J Y, Mercadier J J: Molecular cloning and developmental expression of human cardiac troponin T. FEBS Lett 328:139 44, 1993

91. Doumit M E, Merkel R A: Conditions for isolation and culture of porcine myogenic satellite cells. Tissue Cell 24:253 62, 1992

92. Hirschi K K, Rohovsky S A, D'Amore P A: PDGF, TGF-, and heterotypic cell-cell interactions mediate endothelial cell-induced recruitment of 10 RI/2 cells and their differentiation to a smooth muscle fate. J Cell Biol 141:805 14, 1998

93. Miano J, Cserjesi P, Ligon K, Periasamy M, Olson E: Smooth muscle myosin heavy chain exclusively marks the smooth muscle lineage during mouse embryogenesis. Circ Res 75:803 12, 1994

94. Wobus A M, Kaomei G. Shan J, Wellner M C, Rohwedel J, Ji G. Fleischmann B, Katus H A, Hescheler J, Franz W M: Retinoic acid accelerates embryonic stem cell-derived cardiac differentiation and enhances development of ventricular cardiomyocytes. J Mol Cell Cardiol 29:1525 39, 1998

95. Layerriere A C, MacNeill C, Mueller C, Poelmann R E, Burch J B, Evans T: GATA-4/5/6, a subfamily of three transcription factors transcribed in developing heart and gut. J Biol Chem 269:23177 84, 1994

96. Bhavsar P K, Dhoot G K, Cumming D V, Butler-Browne G S, Yacoub M H, Barton P J: Developmental expression of troponin I isoforms in fetal human heart. FEBS Lett 292:5 8, 1991

97. Forssmann W, Richter R, Meyer M: The endocrine heart and natriuretic peptides: histochemistry, cell biology, and functional aspects of the renal urodilatin system. Histochem Cell Biol 110:335 57, 1998

98. Punzel M, Wissink S, Miller J, Moore K, Lemischka I, Verfaillie C: The myeloid-lymphoid initiating cell (ML-IC) assay assesses the fate of multipotent human progenitors in vitro. blood 93:3750 6, 1999

99. Thiemann F T, Moore K A, Smogorzewska E M, Lemischka I R, Crooks G M: The murine stromal cell line AFT024 acts specifically on human $CD34.sub.+CD38-$ progenitors to maintain primitive function and immunophenotype in vitro. Exp Hematol 26:612 619, 1998

100. Rosenberg J B, Foster P A, Kaufinan R J, Vokac E A, Moussalli M, Kroner P A, Montgomery R R: Intracellular trafficking of factor VIII to von Willebrand factor storage granules. J Clin Invest 101:613 24, 1998

101. Baumhueter S. Dybdal N, Kyle C, Lasky L: Global vascular expression of murine CD34 a sialomucin-like endothelial ligand for L-selectin. Blood 84:2554, 1994

102. Hamagushi 1, Huang X L, Takakura N, Tada J. Yamagushi Y, Kodama H, Suda T: In vitro hematopoietic and endothelial cell development from cells expressing TEK receptor in murine aorta-gonad-mesonephros region. Blood 93:1549 1556, 1999

103. Shalaby F, Ho J, Stanford W, Fischer K, Schuh A, Schwartz L, Bernstein A, Rossant J: A requirement for Flk1 in primitive and definitive hematopoiesis and vasculogenesis. Cell 89:981 90, 1997

104. Newman P: The biology of PECAM-1. J Clin Invest 99:3, 1997

105. Tedder T, Steeber D, Chen A, Engel P: The selectins: vascular adhesion molecules. FASEB J 9:866, 1995

106. Nishikawa S, Nishikawa S. Hirashima M. Matsuyoshi N, Kodama H: Progressive lineage analysis by cell sorting and culture identifies FLK1+VE-cadherin+cells at a diverging point of endothelial and hemopoietic lineages. Development 125:1747 57, 1998

107. Belaoussoff M, Farrington S M, Baron M H: Hematopoietic induction and respecification of A-P identity by visceral endoderm signaling in the mouse embryo. Development 125:5009 18, 1988

108. Weiss S, Dunne C, Hewson J, Wohl C, Wheatley M, Peterson A C, Reynolds B A: Multipotent CNS stem cells are present in the adult mammalian spinal cord and ventricular neuroaxis. J Neurosci 16:7599 609, 1996

109. Shihabuddin L S, Ray J, Gage F H: FGF-2 is sufficient to isolate progenitors found in the adult mammalian spinal cord. Exp Neurol 148:577 86, 1997

110. Ciccolini F, Svendsen C N: Fibroblast growth factor 2 (FGF-2) promotes acquisition of epidermal growth factor (EGF) responsiveness in mouse striatal precursor cells: Identification of neural precursors responding to both EGF and FGF-2. J Neuroscience 18(19):7869 7880, 1998

111. Julien J, Mushynski W: Neurofilaments in health and disease. Prog Nucleic Acid Res Mol Biol 61:1 23, 1998

112. Schaafsma H, Ramaekers F: Cytokeratin subtyping in normal and neoplastic epitheliun: basic principles and diagnostic applications. Pathol Annu 29:21 62, 1994

113. Lazaro C A, Rhim J A, Yamada Y, Fausto N: Generation of hepatocytes from oval cell precursors in culture. Cancer Res 58:5514 22, 1998

114. Kiem H, Heyward P, Winkler A, Potter J, Allen J, Miller A, Andrew R: Gene transfer into marrow repopulating cells: comparison between amphotropic and gibbon ape leukemia virus pseudotyped retroviral vectors in a competitive repopulation assay in baboons. Blood 90:4638 45, 1997

115. Nolta J, Dao M, Wells S, Smogorzewska E, Kohn D: Transduction of pluripotent human hematopoietic stem cells demonstrated by clonal analysis after engraftment in immune-deficient mice. Proc Natl Acad Sci USA 93:2414 9, 1996

116. Huibregtse B A, Johnstone B, Goldberg V M, Caplan A I: Effect of age and sanpling site on the chondro-osteogenic potential of rabbit marrow-derived mesenchymal progenitor cells. Orthop Res 18:18 24, 2000

117. Bandyopadhyay P, Ma X, Linehan-Stieers C, Kren B, Steer C: Nucleotide exchange in genomic DNA of rat hepatocytes usingRNA/DNA oligonucleotides. Targeted delivery of liposomes and polyethyleneimine to the asialoglycoprotein receptor. J Biol Chem: 10163 72, 1999

118. Siclaff T D, Nyberg S L, Rollins M D, Hu M Y, Amiot B, Lee A, Wu F J, Hu W S, Cerra F B: Characterization of the three-compartment gel-entrapment porcine hepatocyte bioartificial liver. Cell Biol Toxicol 13:357 64, 1997

119. Peshwa M V, Wu F J, Sharp H L, Cerra F B, Hu W S: Mechanistics of formation and ultrastructural evaluation of hepatocyte spheroids. 32:197 203, 1996

120. Rogler L E: Selective bipotential differentiation of mouse embryonic hepatoblasts in vitro. Am J Pathol 150:591 602, 1997

121. Block G D, Locker J, Bowen W C, Petersen B E, Katyal S, Strom S C, Riley T, Howard T A, Michalopoulos G K: Population expansion, clonal growth, and specific differentiation patterns in primary cultures of hepatocytes induced by HGF/SF, EGF and TGF alpha in a chemically defined (HGM) medium. J Cell Biol 132:1133 49, 1996

122. Hao Q L, Thiemann F T, Petersen D, Smogorzewska E M, Crooks G M: Extended long-term culture reveals a highly quiescent and primitive human hematopoietic progenitor population. Blood 88:3306 3313, 1996

123. Visser J W, Bol S J, van den Engh G: Characterization and enrichment of murine hemopoietic stem cells by fluorescence activated cell sorting. Exp Hematol 9:644 55, 1981

124. Gothot A, van der Loo J C, Clapp D W, Srour E F: Cell cycle-related changes in repopulating capacity of human mobilized peripheral blood CD34(+) cells in non-obese diabetic/severe combined immune-deficient mice. Blood 92:2641 9, 1998

125. Klug M G, Soonpaa M H, Koh G Y, Field L J: Genetically selected cardiomyocytes from differentiating embronic stem cells form stable intracardiac grafts. J Clin Invest 98:216 24, 1996

126. Kipriyanov S M, Little M: Generation of recombinant antibodies. Mol Biotechnol 12:173 201, 1999

127. Shinohara N, Demura T, Fukuda H: Isolation of a vascular cell wall-specific monoclonal antibody recognizing a cell polarity by using a phage display subtraction method. Proc Natl Acad Sci USA 97:2585 90, 2000

128. Iyer V R, Eisen M B, Ross D T, Schuler G, Moore T, Lee J C F, Trent J M, Staudt L M. Hudson J J, Boguski M S, Lashkari D, Shalon D, Botstein D, Brown P O: The transcriptional program in the response of human fibroblasts to serum. Science 283:83 7, 1999

129. Scherf U, Ross D T, Waltham M, Smith L H, Lee J K, Tanabe L, Kohn K W, Reinhold W C, Myers T G, Andrews D T, Scudiero D A, Eisen M B, Sausville E A, Pommier Y, Botstein D, Brown P O, Weinstein J N: A gene expression database for the molecular pharmacology of cancer. Nat Biotech 24:23644, 2000

130. Alizadeh A A, Eisen M B, Davis R E, Ma C, Lossos I S, Rosenwald A, Boldrick J C, Sabet H, Tran T, Yu X, Powell J I, Yang L, Marti G E, Moore T, Hudson J J, Lu L, Lewis D B, Tibshirani R, Sherlock G, Chan W C, Greiner T C, Weisenburger D D, Armitage J O, Warnke R, Staudt L M: Distinct types of diffuse large B-cell lymphoma identified by gene expression profiling. Nature 403:503 11, 2000

131. Diehn M, Eisen M B, Botstein D, Brown P O: Large-scale identification of secreted and membrane-associated gene products using DNA microarrays. Nat Biotech 25:58 62, 2000

132. Wang E, Miller L D, Ohnmacht G A, Liu E T, Marincola F M: High-fidelity mRNA amplification for gene profiling. Nat Biotechnol 18:457 9, 2000

133. Sornia N V, Schmitt M J, Vetter D E, Van Antwerp D, Heinemann S F, Verrna I M: LFG: an anti-apoptotic gene that provides protection from Fas-mediated cell death. Proc Natl Acad Sci USA 96:12667 72, 1999

134. Elefanty A G, Begley C G, Metcalf D, Barnett L, Kontgen F, Robb L: Characterization of hematopoietic progenitor cells that express the transcription factor SCL, using a lacZ "knock-in" strategy. Proc Natl Acad Sci USA 95:11897 902, 1998

135. Asahara T, Takahashi T, Masuda H, Kalka C, Chen D, Twaguro H, Inai Y, Silver M, Isner J: VEGF contributes to postnatal neovascularization by mobilizing bone marrow-derived endothelial progenitor cells. EMBO J. 18:3964 72, 1999

136. Robbins P, Skelton D, Yu X, Halene S, Leonard E, Kohn D: Consistent, persistent expression from modified retroviral vectors in murine hematopoietic stem cells. Proc Natl Acad Sci (USA) 95:10182 87, 1998

137. Case S, Price M, Jordan C, Yu X, Wang L, Bauer G, Haas D, Xu D, Stripecke R, Naldini L, Kohn D, Crooks G: Stable transduction of quiescent CD34(+)CD38(−) human hematopoietic cells by HIV-1-based lentiviral vectors. Proc Natl Acad Sci USA 96:2988 93, 1999

138. Uchida N, Sutton R, Friera A, He D, Reitsma M, Chang W, Veres G, Scollay R, EL. W: HBV, but not murine leukemia virus, vectors mediate high efficiency gene transfer into freshly isolated G0/G1 human hematopoietic stem cells. Proc Natl Acad Sci USA 95:11939 44, 1998

139. Takahashi T, Kalka C, Masuda H, Chen D, Silver M, Kearney M, Magner M, Isner J M, Asahara T: Ischemia- and cytokine-induced mobilization of bone marrow-derived endothelial progenitor cells for neovascularization. Nat Med 5:434 8, 1999

140. Phinney D G, Kopen G, Isaacson R L, Prockop D J: Plastic adherent stromal cells from the bone marrow of commonly used strains of inbred mice: variations in yield, growth, and differentiation. J Cell Biochem 72:570 85, 1999

141. Svendsen C N, Skepper J, Rosser A E, ter Borg M G, Tyres P, Ryken T: Restricted growth potential of rat neural precursors as compared to mouse. Brain Res Dev Brain Res 99:253 8, 1997

142. Cheshier S H, Morrison S J, Liao X, Weissman I L: In vivo proliferation and cell cycle kinetics of long-term self-renewing hematopoietic stem. Proc Natl Acad Sci USA 96:3120 5, 1999

143. Homer P J, Power A E, Kempermann G, Kuhn H G, Palmer T D, Winkler J, Thal L J, Gage F H: Proliferation and differentiation of progenitor cells throughout the intact adult rat spinal cord. J Neurosci 20:2218 28, 2000

144. Randall T D, Weissman I L: Phenotypic and functional changes induced at the clonal level in hematopoietic stem cells after 5-fluorouracil treatment. Blood 89:3596 606, 1997.

145. Caplan, A. I. (1991) Mesenchymal stem cells. J. Orthop Res 9: 641-650.

146. Caplan, A. I. (2000) Tissue engineering design for the future: new logics, old molecules. Tissue Eng 6: 1-8.

146. Caplan, A. I. (2003) Design parameters for function tissue engineering; in Guilak, F., D. L. Butler, S. A.

147. Goldstein, D. J. Mooney (eds): Functional Tissue Engineering. New York, Springer, pp 129-138.

148. Caplan, A. I. (2004) Mesenchymal stem cells; in Lanza, R. (ed): Handbook of Stem Cells. New York, Academic Press, vol 2, pp 299-308.

149. Caplan, A. I. (2005) Mesenchymal stem cells; cell-based reconstructive therapy in orthopedics. Tissue Eng 11: 1198-1211.

150. Caplan, A. I., S. P. Bruder (2001) Mesenchymal stem cells: building blocks for molecular medicine in the 21st century. Trends Mol Med 6: 259-264.

151. Kuehle I., M. A. Goodell (2002) The therapeutic potential of stem cells from adults. BMJ 325: 372-376.

152. Pittenger, M. F., B. J. Martin (2004) Mesenchymal stem cells and their potential as cardiac therapeutics. Circ Res 95: 9-20.

153. Jiang Y, B. N. Jahagirdar, R. L. Reinhardt, R. E. Schwartz, C. D. Keene, X. R. Ortiz-Gonzalez, M. Reyes, T. Lenvik. T. Lund, M Blackstad, J. Du, S. Aldrich, A. Lisberg, W. C. Low, D. A. Largaespada, C. M. Verfaillie (2002) Pluripotency of mesenchymal stem cells derived from adult marrow. Nature 418: 41-49.

154. Houghton J., C. Stoicov, S. Nomura, A. B. Rogers, J. Carlson, H. Li, X. Cai, J. G. Fox, J. R. Goldenring, T. C. Wang (2004) Gastric cancer originating from bone marrow-derived cells. Science 306: 1568-1571.

155. Zuk, P. A., M. Zhu, P. Ashjian, D. A. De Ugarte, J. I. Huang, H. Mizuno, Z. C. Alfonso, J. K. Fraser, P. Benhaim, M. H. Hedrick (2002). Human adipose tissue is a source of multipotent stem cells. Mol Biol Cell 13: 4279-4295.

156. Miki, T., T. Lehmann, H. Cai, D. B. Stolz, S. C. Strom (2005) Stem cell characteristics of amniotic epithelial cells. Stem Cells 23: 1549-1559.

157. Mann, L. M., D. P. Lennon, A. I. Caplan (1996) Cultured rat pulp cells have the potential to form bone, cartilage, and dentin in vivo; in Davidovitch, Z., L. A. Norton (eds): Biological Mechanisms of Tooth Movement and Craniofacial Adaptation. Boston, Harvard Society of the Advancement of Orthodontics, pp 7-10.

158. Miura M, S. Gronthos. M. Zhao, B. Lu, L. W. Fisher, P. G. Robey, S. Shi (2003) SHED: stem cells from human exfoliated deciduous teeth. Proc Nat Acad Sci USA 100: 5807-5812.

159. Chambers, I., D. Colby, M. Robertson, J. Nichol, S. Lee, S. Tweedie, A. Smith (2003) Functional expression cloning of Nanog, a pluripotency sustaining factor in embryonic stem cells. Cell 113: 643-655.

160. Constantinescu, S. (2003) Stemness, fusion and renewal of hematopoietic and embryonic stem cells. J Cell Mol Biol 7: 103-112.

161. Laslett, A. L., A. A. Filipczyk, M. F. Pera (2003) Characterization and culture of human embryonic stem cells. Trends Cardiovasc Med 13: 295-301.

162. Mitsui, K., Y. Tokuzawa, H. Itoh, K. Segawa, M. Murakami, K. Takahashi, M. Maruyama, M. Maeda, S. Yamanaka (2003) The homeoprotein Nanog is required for maintenance of pluripotency in mouse epiblast and ES cells. Cell 113: 631-642.

163. Pierdomenico, L., L. Bonsi, M. Calvitti, D. Rondelli, M. Arpinati, G. Chirumbolo, E. Becchetti, C. Marchionni, F. Alviano, V. Fossati, N. Staffolani, M. Franchina, A. Grossi, G. P. Bagnara (2005) Multipotent mesenchymal stem cells with immunosuppressive activity can be easily isolated from dental pulp. Transplantation 80: 836-842.

164. Laino, G., A. Graziano, R. d'Aquino, G. Pirozzi, V. Lanza, S. Valiante, A. De Rosa, F. Naro, E. Vivarelli, G. Papaccio (2006) An approachable human adult stem cell source for hard tissue engineering. J Cell Physiol 3: 693-701.

165. Bissell, M. J., M. A. Lafarge (2005) Context, tissue plasticity, and cancer: are tumor stem cells also regulated by the microenvironment? Cancer Cell 7: 17-23.

166. Schwartz, R. E., C. M. Verfaillie (2005) Adult stem cells plasticity; in J. Odorico, S. C. Zhang, R. Pedersen (eds): Human Embryonic Stem Cells. New York, Garland Science/BIOS Scientific Publisher, pp 45-60.

What is claimed is:

1. A method of obtaining a population of dental pulp marrow similar cells (DPMSCs) comprising:
    culturing a dental pulp source in media supplemented with human serum at a concentration of about 0.5-2.25% and growth factors selected from the group consisting of: platelet-derived growth factor, insulin, selenium, epidermal growth factor (EGF), insulin-like growth factor (IGF), dexamethasone, linoleic acid, and ascorbic acid to obtain the population of DPMSCs,
    wherein at least 90% of the cells in the population express the following markers: CDIO, CD13, CD29, CD44, CD49a, CD49d, CD59, CD73, CD90, CD105, Oct-4 Isoform A and B, Nanog, Sox-2, and SSEA-4.

2. The method of claim 1 wherein the DPMSCs are human DPMSCs and the dental pulp source is from a human.

3. The method of claim 1, wherein adherent cells and non-adherent cells are co-cultured without selection by immunodepletion, physical depletion, or chemical depletion.

4. The method of claim 3 wherein the method does not deplete the starting source of cells or the cell culture of mononuclear cells co-expressing CD3, CD 14, CD 19, CD38, CD66b, CD45+, and glycophorin A.

5. The method of claim 3, further comprising placing the cells in a cell culture container, wherein the cell culture container does not comprise an extracellular matrix (ECM) substrate.

6. The method of claim 1, wherein the insulin is present at a concentration of about 10 to about 50 µg/ml, transferrin at a concentration of greater than 0 but less than about 10 µg/ml, selenium at a concentration of about 0.1 to about 5 µg/ml, linoleic acid at a concentration of about 0 to about 1 µg/mL, dexamethasone at a concentration of about 0.005 to 0.15 µM, L-ascorbic acid at a concentration of about 10-50 mg/L, platelet-derived growth factor at a concentration of about 1 to about 50 ng/ml, epidermal growth factor at a concentration of about 1 to 50 ng/ml, insulin-like growth factor at a concentration of 1 to about 50 ng/ml, and fibroblast growth factor-b at a concentration of about 1 to 50 ng/ml.

7. The method of claim 1, wherein the cells are cultured for at least seven days.

8. The method of claim 7, wherein the cells are cultured for at least two weeks.

9. The method of claim 8, wherein the cells are cultured for two to three weeks.

\* \* \* \* \*